US012559551B2

(12) United States Patent
Liu et al.

(10) Patent No.: US 12,559,551 B2
(45) Date of Patent: Feb. 24, 2026

(54) STABILIZED FORMULATIONS CONTAINING ANTI-ANGPTL3 ANTIBODIES

(71) Applicant: Regeneron Pharmaceuticals, Inc., Tarrytown, NY (US)

(72) Inventors: Dingjiang Liu, Pleasantville, NY (US); Andria Skinner, Mohegan Lake, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 523 days.

(21) Appl. No.: 16/882,280

(22) Filed: May 22, 2020

(65) Prior Publication Data

US 2020/0369760 A1    Nov. 26, 2020

Related U.S. Application Data

(60) Provisional application No. 62/852,643, filed on May 24, 2019.

(51) Int. Cl.
*A61K 39/395* (2006.01)
*A61K 9/00* (2006.01)
*C07K 16/22* (2006.01)

(52) U.S. Cl.
CPC ............ *C07K 16/22* (2013.01); *A61K 9/0019* (2013.01); *C07K 2317/565* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,997,423 A | 3/1991 | Okunda et al. |
| 5,908,686 A | 6/1999 | Sudo et al. |
| 6,030,831 A | 2/2000 | Godowski |
| 6,286,699 B1 | 9/2001 | Sudo |
| 6,348,351 B1 | 2/2002 | Fong |
| 6,629,949 B1 | 10/2003 | Douglas |
| 6,645,635 B2 | 11/2003 | Muraki |
| 6,659,982 B2 | 12/2003 | Douglas et al. |
| 7,226,554 B2 | 6/2007 | Sudo et al. |
| 7,267,819 B2 | 9/2007 | Ferrara |
| 7,935,796 B2 | 5/2011 | Lee |
| 8,062,640 B2 | 11/2011 | Sleeman |
| 8,742,075 B2 | 6/2014 | Lee et al. |
| 9,018,356 B2 | 4/2015 | Sleeman et al. |
| 9,322,018 B2 | 4/2016 | Bettencourt |
| 9,951,127 B2 | 4/2018 | Sleeman et al. |
| 9,957,292 B2 | 5/2018 | Prakash et al. |
| 10,358,487 B2 | 7/2019 | Sleeman et al. |
| 2002/0035058 A1 | 3/2002 | Brown et al. |
| 2008/0177045 A1 | 7/2008 | Lee |
| 2009/0098117 A1 | 4/2009 | Ferrara |
| 2010/0166768 A1 | 7/2010 | Sleeman et al. |
| 2011/0243948 A1 | 10/2011 | Lee |

| | | | |
|---|---|---|---|
| 2011/0245096 A1 | 10/2011 | Aggarwal |
| 2012/0064160 A1 | 3/2012 | Guivarc'h et al. |
| 2012/0135976 A1 | 5/2012 | Kerc et al. |
| 2013/0064834 A1 | 3/2013 | Sleeman |
| 2013/0171149 A1 | 7/2013 | Sleeman et al. |
| 2014/0206845 A1 | 7/2014 | Kameoka et al. |
| 2015/0197564 A1 | 7/2015 | Sleeman et al. |
| 2016/0115246 A1 | 4/2016 | Sasiela et al. |
| 2017/0037124 A1 | 2/2017 | Gusarova et al. |
| 2017/0037409 A1 | 2/2017 | Freier et al. |
| 2017/0233466 A1 | 8/2017 | Gromada |
| 2017/0253666 A1 | 9/2017 | Gusarova |
| 2017/0291937 A1 | 10/2017 | Gromada |
| 2017/0312359 A1 | 11/2017 | Pordy |
| 2019/0092845 A1 | 3/2019 | Sleeman et al. |
| 2019/0315851 A1 | 10/2019 | Sleeman et al. |
| 2020/0061189 A1 | 2/2020 | Pordy |
| 2020/0079841 A1 | 3/2020 | Gromada |
| 2020/0199253 A1 | 6/2020 | Gusarova |
| 2020/0377583 A1 | 12/2020 | Gromada |
| 2022/0072127 A1 | 3/2022 | Pordy |
| 2022/0089711 A1 | 3/2022 | Gromada |

(Continued)

FOREIGN PATENT DOCUMENTS

| | | |
|---|---|---|
| CN | 101905024 | 12/2010 |
| CN | 107106678 A | 8/2017 |

(Continued)

OTHER PUBLICATIONS

Zhang, Bao-yu et al., "The correlation study on angiopoietin-like protein 3 and diabetic angiopathies, dyslipidemia", English abstract, Proceedings of Clinical Medicine, vol. 23, No. 8, Aug. 31, 2014, pp. 565-568.

Ando et al., (2003) J. Lipid. Res 44(6):1216-1223, "A decreased expression of angiopoietin-like 3 is protective against atherosclerosis in apoE-deficient mice".

Borodovsky et al., (2014) Alnylam Pharmaceuticals, "Developments of Monthly to Quarterly Subcutaneous Administration of RNAi Therapeutics Targeting the Metabolic Disease Genes PCSK9, ApoC3 and ANGPTL3 ALN-PCS Phase I Study Results" Website [Online] Available Website: www.alnylam.com/web/assets/Cardiometaboliclike_AHA_Poster_111714.pdf; Last Update: unknown; Accessed on: May 9, 2017.

Brandt, Teresa, et al., "ISIS-ANGPTL3RX, an antisense inhibitor to angiopoietin-like 3, reduces plasma lipid levels in mouse models and in healthy human volunteers", *Abstracts* EAS-0824/Atherosclerosis 241 (Jul. 2015) e1-e31.

(Continued)

*Primary Examiner* — Yunsoo Kim

(74) *Attorney, Agent, or Firm* — Merchant & Gould P.C.

(57) ABSTRACT

The present invention provides stable pharmaceutical formulations comprising a human antibody that specifically binds to human angiopoietin-like protein 3 (ANGPTL3). The formulations may contain, in addition to an anti-ANGPTL3 antibody, a buffer; an organic cosolvent; at least one viscosity modifier, and optionally at least one amino acid. The pharmaceutical formulations of the present invention can be administered via intravenous infusion or subcutaneously and exhibit a substantial degree of antibody stability after storage for several months.

29 Claims, 20 Drawing Sheets

Specification includes a Sequence Listing.

(56)                    References Cited

U.S. PATENT DOCUMENTS

| | | | |
|---|---|---|---|
| 2022/0127348 A1 | 4/2022 | Gromada |
| 2022/0153825 A1 | 5/2022 | Sleeman |
| 2022/0403016 A1 | 12/2022 | Sleeman |
| 2023/0000976 A1 | 1/2023 | Pordy |
| 2025/0332254 A1 | 10/2025 | Pordy |

FOREIGN PATENT DOCUMENTS

| | | | | |
|---|---|---|---|---|
| CN | 109069868 A | 12/2018 | | |
| EP | 1482041 | 12/2004 | | |
| EP | 2735315 | 5/2014 | | |
| JP | 2002-521475 | 7/2002 | | |
| JP | 2002-536459 | 10/2002 | | |
| JP | 2005080508 | 3/2005 | | |
| JP | 2010-512320 | 4/2010 | | |
| JP | 2012-511913 | 5/2012 | | |
| JP | 2012-518639 | 8/2012 | | |
| JP | 2015-536934 | 12/2015 | | |
| TW | 200846364 | 12/2008 | | |
| WO | 2003/044172 | 5/2003 | | |
| WO | 2006/098887 | 9/2006 | | |
| WO | 2008/073300 | 6/2008 | | |
| WO | WO-2009100318 A1 * | 8/2009 | ............ | C07K 16/40 |
| WO | 2010/111892 | 10/2010 | | |
| WO | 2011/008773 | 1/2011 | | |
| WO | 2011/085271 | 7/2011 | | |
| WO | 2012/174178 | 12/2012 | | |
| WO | 2014/152776 | 9/2014 | | |
| WO | 2014/194168 | 12/2014 | | |
| WO | 2015/077154 | 5/2015 | | |
| WO | 2015/100394 | 7/2015 | | |
| WO | 2016/011256 | 1/2016 | | |
| WO | 2016/054494 | 4/2016 | | |
| WO | 2017027316 | 2/2017 | | |
| WO | 2017177181 | 12/2017 | | |
| WO | 2018/187057 | 10/2018 | | |

OTHER PUBLICATIONS

Broxmeyer, H.E. et al., "Angiopoietin-like-2 and -3 act through their coiled-coil domains to enhance survival and replating capacity of human cord blood hematopoietic progenitors", Blood Cells, Molecules, and Diseases 48 (2012), Oct. 7, 2011, pp. 25-29, abstract.

Calandra et al., "Familial combined hypolipidemia due to mutations in the ANGPTL3 gene", Clinical Lipidology, 2013, 8: 1, 81-95.

Camenisch et al., (2002) J. Biol. Chem. 277(19):17281-17290, "ANGPTL3 Stimulates Endothelial Cell Adhesion and Migration via Integrin alpha v beta 3 and induces Blood Vessel Formation in Vivo".

Conklin et al. (1999) Genomics 62(3):477-482, "Identification of a Mammalian Angiopoietin-Related Protein Expressed Specifically in Liver".

Correia (2010) mAbs 2(3):221-232, "Stability of IgG isotypes in serum".

Ecuadorian English translation of the opposition brief dated Mar. 13, 2015 for corresponding Ecuadorian application No. SP 2013-13085.

Fenzl et al., "Circulating betatrophin correlates with atherogenic lipid profiles but not with glucose and insulin levels in insulin-resistant individuals", Diabetologia (2014), 57(6), 1204-1208.

Gaudet (2016) Journal of Clinical Lipidology 10(3):715 "Safety and Efficacy of Evinacumab, a monoclonal antibody to ANGPTL3, in Patients with Homozygous Familial Hypercholesterolemia Receiving Concomitant Lipid-Lowering Therapies".

Gaudet (2017) Journal of Clinical Lipidology 11(3): 837-838 "Safety and Efficacy of Evinacumab, A Monoclonal Antibody to ANGPTL3, in Homozygous Familial Hypercholesterolemia".

Gusarova, "ANGPTL3 Blockage with a Human Monoclonal Antibody Reduces Plasma Lipids in Dyslipidemic Mice and Monkeys", (2015), Journal of Lipid Research 56(7):1308-1317.

Haller, Jorge F., et al., "ANGPTL8 requires ANGPTL3 to inhibit lipoprotein lipase and plasma triglyceride clearance," Journal of Lipid Research, vol. 58, No. 6, Jun. 1, 2017, pp. 1166-1173, XP55387875.

Hanson, Robert L. et al., "The ARG59Trp Variant in ANGPTL8 (betatrophin) is Associated with Total and HDL-Cholesterol in American Indians and Mexican Americans and Differentially Affects Cleavage of ANGPTL3", Molecular Genetics and Metabolism Academic Press, Amsterdam, NL, 118(2):128-137.

Huijgen et al., "Genetic variation in APOB, PCSK9, and ANGPTL3 in carriers of pathogenic autosomal dominant hypercholesterolemic mutations with unexpected low LDL-C levels", Human Mutation 2012;33(2):448-455, 19 pages.

Karlsson, Robert, et al., "Affinity Measurement Using Surface Plasmon Resonance", Methods in Molecular Biology, (2004), vol. 248, pp. 389-415.

Koishi et al., (2002) Nat. Genet. 30(2):151-157, "Angptl3 regulates lipid metabolism in mice".

Kuhnast et al. (2014) J Lipid Res. 55(10):2103-2112 "Alirocumab inhibits atherosclerosis, improves the plaque morphology, and enhances the effects of a statin".

Labrijn, Aran F. et al., "Therapeutic IgG4 antibodies engage in Fab-arm exchange with endogenous human IgG4 in vivo", Nature Biotechnology, (Aug. 2009), vol. 27, No. 8, pp. 767-771.

Lee et al., "Identification of a New Functional Domain in Angiopoietin-like 3 (ANGPTL3) and Angiopoietin-like 4 (ANGPTL4) Involved in Binding and Inhibition of Lipoprotein Lipase (LPL)", Journal of Biological Chemistry (2009), 284(20), 13735-13745.

Liakos et al., "PCSK9-targeting monoclonal antibodies for the management of hypercholesterolemia: a systematic review and meta-analysis", Jun. 1, 2014, online at: http://www.crd.york.ac.uk/PROSPEROFILES/7051_PROTOCOL_20140008.pdf, 16 pages.

Lloyd et al., "Modelling the human immune response: performance of a $10^{11}$ human antibody repertoire against a broad panel of therapeutically relevant antigens", Protein Engineering, Design & Selection vol. 22, No. 3, 2009, pp. 159-168.

Montero-Julian, Felix A. et al., "Pharmacokinetic Study of Anti-Interleukin-6 (IL-6) Therapy With Monoclonal Antibodies: Enhancement of IL-6 Clearance by Cocktails of Anti-IL-6 Antibodies", Blood, vol. 85, No. 4, Feb. 15, 1995, pp. 917-924.

Musunuru et al., "Exome Sequencing, ANGPTL3 Mutations, and Familial Combined Hypolipidemia", The New England Journal of Medicine, 363;23:2220-2227, Dec. 2, 2010.

Oike, Y. et al., "Angiopoietin-like proteins: potential new targets for metabolic syndrome therapy", Trends in Molecular Medicine, Oct. 2005, vol. 11, No. 10, pp. 473-479.

Ono, Mitsuru et al., "Protein Region Important for Regulation of Lipid Metabolism in Angiopoietin-like 3 (ANGTPL3): ANGPTL3 Is Cleaved and Activated In Vivo", Oct. 24, 2003, Journal of Biological Chemistry, The American Society of Biological Chemists, Inc. 278(43):41804-41809.

O'Riordan, Mike, "Gene Mutations Linked With Low LDL-Cholesterol Levels: ANGPTL3. ANGPTL3 and LDL Cholesterol", Oct. 15, 2010, pp. 1-2, located online at: https://www.medscape.com/viewarticle/730654.

Pramfalk et al., "Effects of high-dose statin on the human hepatic expression of genes involved in carbohydrate and triglyceride metabolism", J Intern Med 2011 ;269: 333-339.

Rader et al. (2015) Cell Metabolism 23(3): 405-412 "New Therapeutic Approaches to the Treatment of Dyslipidemia".

Rossetti and Goldberg (2002) Nat. Med. 8(2):112-114, "A new piece in the diabetes puzzle".

Shimamura et al., "Leptin and insulin down-regulate angiopoietin-like protein 3, a plasma triglyceride-increasing factor", Biochemical and Biophysical Research Communications (2004), 322(3), 1080-1085.

Shimizugawa et al., (2002) J. Biol. Chem. 277(37):33742-33748, "ANGPTL3 Decreases Very Low Density Lipoprotein Triglyceride Clearance by Inhibition of Lipoprotein Lipase".

Sonnenburg et al. GPIHBP1 stabilizes lipoprotein lipase and prevents its inhibition by angiopoietin-like 3 and angiopoietin-like 4. Journal of Lipid Research (2009), 50(12), 2421-2429.

(56) References Cited

OTHER PUBLICATIONS

Tikka et al. (2016) Endocrine 52(2):187-193 "The Role of ANGPTL3 in Controlling Lipoprotein Metabolism".

Turner et al., "Non-statin Treatments for Managing LDL Cholesterol and Their Outcomes", Clinical Therapeutics/ vol. 37, No. 12:2751-2769, Dec. 1, 2015.

Wang (2015) Journal of Lipid Research 56(7):1296-1307 "Inactivation of ANGPTL3 Reduces Hepatic VLDL-Triglyceride Secretion".

Yau et al., "A Highly Conserved Motif within the NH2-terminal Coiled-coil Domain of Angiopoietin-like Protein 4 Confers Its Inhibitory Effects on Lipoprotein Lipase by Disrupting the Enzyme Dimerization", Journal of Biological Chemistry (2009), 284(18), 1942-11952.

Yeadon, J., "Which Jax Mouse Model is Best for Atherosclerosis Studies: Apoe or LDLR Knockout Mice?", The Jackson Laboratory, https://www.jax.org/news-and-insights/jax-blog/2013/november/which-jax-mouse-model-is-best-for-atherosclerosis-studies-apoe-or-ldlr-knoc, 1 page, 2018.

Zhang, Ren, "The ANGPTL3-4-8 model, a molecular mechanism for triglyceride trafficking," Open Biology, vol. 6, No. 4, Apr. 1, 2016, p. 150727, XP55387866.

Lyudmila Georgieva Vladimiriova-Kitova et al., "Resistance of Statin Therapy, and Methods for its Influence", In: "Hypercholesterolemia", Sep. 17, 2015, InTech, Chapter 10, 19 pages.

Farnier, M. et al., "Efficacy of alirocumab in heterozygous familial hypercholesterolemia or high cv risk populations: pooled analyses of eight phase 3 trials", Abstracts, EAS-0563, Atherosclerosis, vol. 241, No. 1, 2015, 2 pages.

Sirtori et al., "Microsomal transfer protein (MTP) inhibition—a novel approach to the treatment of homozygous hypercholesterolemia", Annals of Medicine, 46:7, 464-474, 2014.

Cuchel et al., Abstract 1077: A Phase III Study of Microsomal Triglyceride Transfer Protein Inhibitor Lomitapide (AEGR-733) in Patients With Homozygous Familial Hypercholesterolemia: Interim Results at 6 Months, Circulation, 2009, 120: S441.

DeGoma, E.M., "Lomitapide for the Management of Homozygous Familial Hypercholesterolemia", Rev. Cardiovasc Med., 2014;15(2), 109-118.

Masana, Luis et al., "Unmet Needs: Patients with Statin Intolerance or Familial Hypercholesterolemia", Clin Investig Arterioscler, May 28, 2016, Suppl 2:22-30, English abstract.

Bitzur, Rafael et al., "Intolerance to Statins: Mechanisms and Management", Diabetes Care, vol. 36, Supp. 2, Aug. 2013, S325-S330.

Arca, Marcello et al., "Treating statin-intolerant patients", Diabetes, Metabolic Syndrome and Obesity: Targets and Therapy, Dove Press, Apr. 27, 2011, pp. 155-166.

Mayo Clinic, "Niacin", dated Nov. 12, 2020, located online at: https://www.mayoclinic.org/drugs-supplements-niacin/art-20364984#:~:text=Prescription%20niacin%20might%20benefit%20people%20with%20high%20cholesterol,in%20appropriate%20amounts%2C%20niacin%20appears%20to%20be%20safe, 4 pages.

Mayo Clinic, "Niacin to improve cholesterol numbers", Jun. 7, 2022, located online at: https://www.mayoclinic.org/diseases-conditions/high-blood-cholesterol/in-depth/niacin/art-20046208, 3 pages.

Ahn, Chang Ho, et al., "New Drugs for Treating Dyslipidemia: Beyond Statins", Diabetes & Metabolism Journal, vol. 39, No. 2, Apr. 20, 2015, pp. 87-94.

Wang, Yan, et al., "Mice lacking ANGPTL8 (Betatrophin) manifest disrupted triglyceride metabolism without impaired glucose homeostasis", PNAS, Oct. 1, 2013, vol. 10, No. 40, pp. 16109-16114.

Carpenter, J.F. et al., "Rational Design of Stable Lyophilized Protein Formulations: Some Practical Advice", Pharmaceutical Research, vol. 14, No. 8, Jan. 1, 1997, pp. 969-975.

Wang, Wei Ed—Blanco-Prieto, Maria et al., "Instability, stabilization, and formulation of liquid protein pharmaceuticals", vol. 185, No. 2, Aug. 20, 1999, pp. 129-188.

Banerjee, Poulabi et al., "Functional Analysis of LDLR (Low-Density Lipoprotein Receptor) Variants in Patient Lymphocytes to Assess the Effect of Evinacumab in Homozygous Familial Hypercholesterolemia Patients With a Spectrum of LDLR Activity", Translational Sciences, vol. 39, No. 11, Nov. 1, 2019, pp. 2248-2260.

Rosenson, Robert S. et al., "Evinacumab in Patients with Refractory Hypercholesterolemia", The New England Journal of Medicine, vol. 383, No. 24, Dec. 10, 2020, pp. 2307-2319.

Raal, Frederick J., et al., "Evinacumab for Homozygous Familial Hypercholesterolemia", The New England Journal of Medicine, vol. 383, No. 8, Aug. 20, 2020, pp. 711-720.

Ito, Matthew K et al., "Challenges in the Diagnosis and Treatment of Homozygous Familial Hypercholesterolemia.", Drugs vol. 75, 15, 2015: 1715-24. doi:10.1007/s40265-015-0466-y (abstract, Table 1).

Nachtigal P et al., "Atorvastatin has hypolipidemic and anti-inflammatory effects in apoE/LDL receptor-double-knockout mice", Life Sci. Mar. 26, 2008; 82 (13-14):708-17.) doi: 10.1016/j.lfs.2008.01.006. Epub Jan. 26, 2008. PMID: 18289605 (abstract).

Quagliarini, Fabina et al., "Atypical angiopoietin-like protein that regulates ANGPTL3", Proc Natl Acad Sci USA, Nov. 27, 2012, pp. 19751-19756.

Brown et al., "Tolerance of single, but not multiple, amino acid replacements in antibody VH 2: a means of minimizing B cell wastage from somatic hypermutation?", J. Immuno May 1996, 3285-91.

Wardemann, Hedda et al., "Predominant Autoantibody Production by Early Human B Cell Precursors", Science 301, 1374-1377 (2003).

Singer, Maxine et al., "Genes and Genomes", in 2 volumes, Moscow, Mir, 1998, vol. 1, pp. 64, 67 (translated pages correspond to cited pages).

Myers, Calisha, "Aegerion Pharmaceuticals, Inc. Announces AEGR-733 Phase II Data Demonstrates Significant Lowering of LD Cholesterol, Nov. 6, 2008, online at https://www.fiercebiotech.com/biotech/aegerion-pharmaceuticals-inc-announces-aegr-733-phase-ii-data-demonstrates-significant", 5 pgs.

Wang, W, et al., "Antibody structure, instability, and formulation", Jan. 1, 2007, Journal of Pharmaceutical Sciences, vol. 96, No. 1, pp. 1-26. Published online in Wiley InterScience—DOI 10.1002/jps.20727.

Kang, Jichao et al., "Rapid Formulation Development for Monoclonal Antibodies", published Apr. 12, 2016, obtained online at BioProcess International on Jan. 30, 2023 at: http://www.bioprocessintl.com/manufacturing/formulation/rapid-formulation-development-for-monoclonal-antibodies/, 7 pages.

Wang, Wei, et al., "Antibody structure, instability, and formulation", J Pharm Sci. Jan. 2007;96(1): 1-26.

Rosenson, Robert S. et al., "Evinacumab in severe hypertriglyceridemia with or without lipoprotein lipase pathway mutations: a phase 2 randomized trial", Nature Medicine, vol. 29, Mar. 2023; 729-737.

Goldberg, Ronald et al., "A Comprehensive Update on the Chylomicronemia Syndrome", Frontiers in Endocrinology, Oct. 23, 2020, vol. 11, article 593931, 13 pages.

Gidding, Sam et al., "The Agenda for Familial Hypercholesterolemia: A Scientific Statement From the American Heart Association", Circulation, 2015; 132:2167-2192; downloaded from http://ahajournals.org on Dec. 15, 2023.

Oldoni et al., "ANGPTL8 has both endocrine and autocrine effects on substrate utilization", JCI Insight 2020; 5(17): e138777, 19 pages.

Hung, Jessica et al., "Improving Viscosity and Stability of a Highly Concentrated Monoclonal Antibody Solution with Concentrated Proline", Pharm Res (2018) 35: 133, 14 pages; https://doi.org/10.1007s/11095-018-2398-1.

Kolansky et al., "Longitudinal Evaluation and Assessment of Cardiovascular Disease in Patients with Homozygous Familial Hypercholesterolemia", 2008, The American Journal of Cardiology 102:1438-1443.

Santos et al., "Type of LDLR mutation and the pharmacogenetics of familial hypercholesterolemia treatment", 2015 Pharmacogenomics 16:1743-1750.

Rader, Daniel J. et al., "Lomitapide and Mipomersen: Two First-in-Class Drugs for Reducing Low-Density Lipoprotein Cholesterol

(56)　　　　　References Cited

OTHER PUBLICATIONS in Patients with Homozygous Familial Hypercholesterolemia", 2014 Circulation 129, Issue 9:1022-1032.

Immunology Illustrated, 5th Edition, pp. 71-82, Nankodo Corporation, 2000,(Original: Immunology Fifth Edition by Ivan Roitt, Jonathan Brostoff and David Male), with partial English translation, 23 pages with translation.

Daugherty, Ann et al., "Formulation and delivery issues for monoclonal antibody therapeutics", Advanced Drug Delivery Reviews 58 (2006) 686-706.

Merck Manual, 18th Edition, Japanese version, 2006, Item "72 Atherosclerosis", English translation precedes the Russian language article, 12 pages total.

Reeskamp, Laurens et al., "Marked plaque regression in homozygous familial hypercholesterolemia", Atherosclerosis, Elsevier, Amsterdam, NL, vol. 327, May 3, 2021, pp. 13-17.

Brown, Greg et al., "Does ENHANCE Diminish Confidence in Lowering LDL or in Ezetimibe?", The New England Journal of Medicine, vol. 358, No. 14, Apr. 3, 2008, pp. 1504-1507.

Kastelein, John et al., "Simvastatin with or without Ezetimibe in Familial Hypercholesterolemia", New England Journal of Medicine, vol. 358, No. 14, Apr. 3, 2008, pp. 1431-1443.

Rosenson, Robert et al., "Abstract 12054: Evinacumab Reduces Atherogenic Lipids and Apolipoprotein B in Patients with Severe Hypertriglyceridemia", Circulation, vol. 144, No. Suppl_1, Nov. 8, 2021, 2 pages.

Rosenson, Robert et al., P742/#696, E-Posters Topic, "A Phase 2 trial of the efficacy and safety of evinacumab in patients with severe hypertriglyceridemia" Atherosclerosis, Elsevier, vol. 331, Aug. 1, 2021, p. e293.

Shamsudeen, Isabel et al., "Safety and efficacy of therapies for chylomicronemia", Expert Review of Clinical Pharmacology Nov. 1, 2014 Expert Reviews Ltd, GBR, vol. 15, No. 4, Apr. 3, 2022, 12 pages.

Hato, Tai, et al., "The Role of Angiopoietin-Like Proteins in Angiogenesis and Metabolism", Trends in Cardiovascular Medicine, vol. 18, Issue 1, Jan. 2008, pp. 6-14.

Kotla, S. et al., "The Transcription Factor CREB Enhances Interleukin-17A Production and Inflammation in a Mouse Model of Atherosclerosis", Science Signaling, Sep. 17, 2013, vol. 6, No. 293, ra83, pp. 1-13.

Gitt, Anselm K. et al., "Prevalence and overlap of different lipid abnormalities in statin-treated patients at high cardiovascular risk in clinical practice in Germany", Clin Res Cardiol, 2010, vol. 99, No. 11, pp. 723-733.

* cited by examiner

FIGURE 2

Table 2:

| Formulation | | 150 mg/mL H4H1276S, 10 mM histidine, 75 mM arginine-HCl | | | | | | | | |
|---|---|---|---|---|---|---|---|---|---|---|
| Fill Volume | | 0.4 mL | | | | | | | | |
| Container/Closure | | 2 mL Type 1 clear glass vial with a FluroTec® coated 4432/50 chlorobutyl stopper | | | | | | | | |
| pH/Thermal Stabilizer (% w/v) | FDG Lot Number | Color and Appearance[a] | Turbidity (Increase in OD at 405 nm) | % Protein Recovered by RP-UPLC | Change in Purity by SE-UPLC[b] | | | Change in Charge Variants by CEX-UPLC[b] | | |
| | | | | | % HMW | % Monomer | % LMW | % Acidic | % Main | % Basic |
| 5.5/5% Sucrose | L12-673 | Pass | 0.03 | 100 | 7.6 | -7.4 | -0.2 | 10.7 | -12.2 | 1.5 |
| 5.8/5% Sucrose | L12-674 | Pass | 0.01 | 101 | 4.3 | -4.2 | -0.2 | 14.3 | -16.1 | 1.8 |
| 6.0/5% Sucrose | L12-675 | Pass | 0.03 | 102 | 3.7 | -3.5 | -0.2 | 16.4 | -16.6 | 0.2 |
| 6.2/5% Sucrose | L12-676 | Pass | 0.02 | 104 | 3.6 | -3.4 | -0.2 | 24.9 | -24.5 | -0.4 |
| 6.5/5% Sucrose | L12-677 | Pass | 0.02 | 100 | 3.9 | -3.7 | -0.2 | 31.3 | -26.0 | -5.3 |
| 5.5/2% Proline | L12-678 | Pass | 0.04 | 99 | 10.6 | -10.5 | -0.2 | 11.5 | -12.9 | 1.4 |
| 5.8/2% Proline | L12-679 | Pass | 0.02 | 100 | 5.8 | -5.6 | -0.2 | 14.4 | -13.2 | -1.2 |
| 6.0/2% Proline | L12-680 | Pass | 0.01 | 101 | 4.8 | -4.7 | -0.2 | 17.4 | -16.5 | -0.8 |
| 6.2/2% Proline | L12-681 | Pass | 0.02 | 104 | 3.9 | -3.7 | -0.2 | 26.8 | -26.0 | -0.8 |
| 6.5/2% Proline | L12-682 | Pass | 0.02 | 106 | 4.0 | -3.7 | -0.3 | 31.0 | -29.1 | -1.9 |

FIGURE 3

Table 3:

| Formulation | 150 mg/mL H4H1276S, 10 mM histidine, 70 mM arginine-HCl, pH 6.0 |
| --- | --- |
| Fill Volume | 2 mL |
| Container/Closure | 5 mL Type 1 clear glass vial with a FluroTec® coated 4432/50 chlorobutyl stopper |

| % w/v Sucrose or Proline | % w/v Polysorbate 80 | FDG Lot Number | Color and Appearance [a] | Turbidity (Increase in OD at 405 nm) | pH | % Protein Recovered by RP-UPLC | Change in Purity by SE-UPLC[b] | | | Change in Charge Variants by CEX-UPLC[b] | | |
| --- | --- | --- | --- | --- | --- | --- | --- | --- | --- | --- | --- | --- |
| | | | | | | | % HMW | % Monomer | % LMW | % Acidic | % Main | % Basic |
| 5% Sucrose | 0% | L12-908 | Pass | 0.02 | 6.0 | 95 | 4.8 | -4.8 | 0.0 | 0.4 | 0.3 | -0.7 |
| | 0.02% | L12-909 | Pass | 0.00 | 6.0 | 103 | 1.7 | -1.7 | 0.0 | 0.0 | -0.5 | 0.5 |
| | 0.05% | L12-910 | Pass | 0.00 | 6.0 | 99 | 0.1 | -0.1 | 0.0 | 0.4 | 0.4 | -0.9 |
| | 0.1% | L12-911 | Pass | 0.00 | 6.0 | 99 | 0.0 | 0.0 | 0.0 | -0.6 | 0.2 | 0.4 |
| 2% Sucrose/ 1.3% Proline | 0% | L12-912 | Pass | 0.02 | 6.0 | 97 | 6.3 | -6.3 | 0.0 | -0.3 | 3.8 | -3.5 |
| | 0.02% | L12-913 | Pass | 0.01 | 6.0 | 98 | 1.8 | -1.7 | 0.0 | 0.4 | -0.4 | 0.0 |
| | 0.05% | L12-914 | Pass | 0.00 | 6.0 | 97 | 0.1 | -0.1 | 0.0 | 0.4 | 0.1 | -0.4 |
| | 0.1% | L12-915 | Pass | 0.01 | 6.0 | 98 | 0.0 | 0.0 | 0.0 | 0.4 | -0.1 | -0.3 |
| 2% Proline | 0% | L12-916 | Pass | 0.00 | 6.0 | 98 | 4.8 | -4.8 | 0.0 | -0.6 | 1.7 | -1.1 |
| | 0.02% | L12-917 | Pass | 0.00 | 6.0 | 97 | 1.2 | -1.2 | 0.0 | 0.0 | 1.0 | -1.0 |
| | 0.05% | L12-918 | Pass | 0.01 | 6.0 | 94 | 0.1 | -0.1 | 0.0 | -0.3 | -0.6 | 0.9 |
| | 0.1% | L12-919 | Pass | 0.01 | 6.0 | 100 | 0.0 | 0.0 | 0.0 | -0.1 | 1.6 | -1.5 |

FIGURE 4

Table 4:

| Formulation | | | | 150 mg/mL H4H1276S, 10 mM histidine, 70 mM arginine-HCl, pH 6.0 | | | | | | | | | |
| Fill Volume | | | | 1.5 mL | | | | | | | | | |
| Container/Closure | | | | 5 mL Type 1 clear glass vial with a FluroTec® coated 4432/50 chlorobutyl stopper | | | | | | | | | |

| % w/v Sucrose or Proline | % w/v Polysorbate 80 | FDG Lot Number | Color and Appearance [a] | Turbidity (Increase in OD at 405 nm) | pH | % Protein Recovered by RP-UPLC | Change in Purity by SE-UPLC[b] | | | Change in Charge Variants by CEX-UPLC[b] | | |
|---|---|---|---|---|---|---|---|---|---|---|---|---|
| | | | | | | | % HMW | % Monomer | % LMW | % Acidic | % Main | % Basic |
| 5% Sucrose | 0% | L12-908 | Pass | 0.03 | 6.0 | 96 | 3.1 | -3.6 | 0.5 | 17.9 | -22.2 | 4.3 |
| | 0.02% | L12-909 | Pass | 0.02 | 6.0 | 98 | 3.2 | -3.7 | 0.5 | 15.3 | -18.0 | 2.6 |
| | 0.05% | L12-910 | Pass | 0.02 | 6.0 | 96 | 3.2 | -3.8 | 0.6 | 18.2 | -19.4 | 1.2 |
| | 0.1% | L12-911 | Pass | 0.01 | 6.0 | 98 | 3.2 | -3.8 | 0.5 | 21.1 | -24.2 | 3.1 |
| 2% Sucrose/ 1.3% Proline | 0% | L12-912 | Pass | 0.03 | 6.0 | 97 | 3.5 | -4.1 | 0.6 | 18.8 | -17.8 | -1.0 |
| | 0.02% | L12-913 | Pass | 0.03 | 6.0 | 95 | 3.6 | -4.2 | 0.6 | 15.4 | -16.0 | 0.6 |
| | 0.05% | L12-914 | Pass | 0.02 | 6.0 | 93 | 3.7 | -4.2 | 0.5 | 15.6 | -17.5 | 1.9 |
| | 0.1% | L12-915 | Pass | 0.02 | 6.0 | 97 | 3.8 | -4.4 | 0.6 | 17.5 | -18.1 | 0.6 |
| 2% Proline | 0% | L12-916 | Pass | 0.03 | 6.0 | 97 | 3.8 | -4.3 | 0.5 | 15.5 | -16.5 | 1.0 |
| | 0.02% | L12-917 | Pass | 0.02 | 6.0 | 99 | 3.9 | -4.4 | 0.5 | 18.0 | -18.0 | 0.0 |
| | 0.05% | L12-918 | Pass | 0.03 | 6.0 | 93 | 4.0 | -4.6 | 0.5 | 16.8 | -18.9 | 2.1 |
| | 0.1% | L12-919 | Pass | 0.02 | 6.0 | 99 | 4.1 | -4.6 | 0.5 | 16.5 | -17.7 | 1.2 |

FIGURE 5

Table 5:

| Formulation | 150 mg/mL H4H1276S, 10 mM histidine, 70 mM arginine-HCl, pH 6.0 | | | | | | | | |
|---|---|---|---|---|---|---|---|---|---|
| Fill Volume | 2 mL (Agitation), 1.5 mL (45°C) | | | | | | | | |
| Container/Closure | 5 mL Type 1 clear glass vial with a FluroTec® coated 4432/50 chlorobutyl stopper | | | | | | | | |
| % w/v Sucrose or Proline | % w/v Polysorbate 80 | FDG Lot Number | Agitation by Vortexing for 120 minutes Particle Analysis by MFT[a] (# per mL) | | | Incubation at 45°C for 28 days Particle Analysis by MFT[a] (# per mL) | | | |
| | | | 2-10 μm | ≥ 10 μm | ≥ 25 μm | 2-10 μm | ≥ 10 μm | ≥ 25 μm | |
| 5% Sucrose | 0% | L12-908 | 137 | 6 | 2 | 624 | 295 | 30 | |
| | 0.02% | L12-909 | 123 | 46 | 7 | 245 | 132 | 23 | |
| | 0.05% | L12-910 | 190 | 114 | 17 | 72 | 22 | 2 | |
| | 0.1% | L12-911 | 122 | 94 | 23 | 243 | 147 | 11 | |
| 2% Sucrose/ 1.3% Proline | 0% | L12-912 | 680 | 212 | 29 | 354 | 181 | 29 | |
| | 0.02% | L12-913 | Not Applicable (Data Saving Error) | | | 200 | 116 | 13 | |
| | 0.05% | L12-914 | 417 | 233 | 29 | 78 | 94 | 23 | |
| | 0.1% | L12-915 | 256 | 81 | 5 | 136 | 43 | 2 | |
| 2% Proline | 0% | L12-916 | 1672 | 268 | 26 | 27 | 4 | 0 | |
| | 0.02% | L12-917 | 508 | 286 | 39 | 99 | 27 | 0 | |
| | 0.05% | L12-918 | 594 | 144 | 18 | 656 | 511 | 92 | |
| | 0.1% | L12-919 | 413 | 144 | 11 | 809 | 307 | 56 | |

FIGURE 6

Table 7:

| Formulation | 150 mg/mL H4H1276S, 10 mM histidine, pH 6.0, 70 mM arginine-HCl, 0.1% polysorbate 80 or 175 mg/mL H4H1276S, 10 mM histidine, pH 6.0, 70 mM arginine-HCl[a] | | | | | | | | | | |
|---|---|---|---|---|---|---|---|---|---|---|---|
| Fill Volume | 0.4 mL | | | | | | | | | | |
| Container/Closure | 2 mL Type 1 clear glass vial with a FluroTec® coated 4432/50 chlorobutyl stopper | | | | | | | | | | |
| Sucrose/Proline Concentration (% w/v) | FDG Lot Number | Color and Appearance[b] | Turbidity (Increase in OD at 405 nm) | pH | % Protein Recovered by RP-UPLC | Change in Purity by SE-UPLC[c] | | | Change in Charge Variants by CEX-UPLC[c] | | |
| | | | | | | % HMW | % Monomer | % LMW | % Acidic | % Main | % Basic |
| 5%/0% | L12-741 | Pass | 0.00 | 6.1 | 102 | 0.1 | -0.2 | 0.0 | 0.9 | -0.7 | -0.3 |
| 3%/1% | L12-742 | Pass | 0.01 | 6.1 | 100 | 0.1 | -0.2 | 0.1 | 0.2 | -0.6 | 0.4 |
| 2%/1.3% | L12-743 | Pass | 0.01 | 6.1 | 101 | 0.2 | -0.2 | 0.1 | 0.6 | -0.7 | 0.1 |
| 0%/2% | L12-744 | Pass | 0.00 | 6.1 | 99 | 0.3 | -0.3 | -0.1 | 0.3 | -1.0 | 0.6 |
| 0%/0%[a] | L12-745 | Pass | 0.02 | 6.1 | 102 | 7.2 | -7.2 | 0.0 | 0.4 | -2.4 | 2.0 |

FIGURE 7

Table 8:

| Formulation | 150 mg/mL H4H1276S, 10 mM histidine, pH 6.0, 70 mM arginine-HCl, 0.1% polysorbate 80 or 175 mg/mL H4H1276S, 10 mM histidine, pH 6.0, 70 mM arginine-HCl[a] | | | | | | | | | | |
|---|---|---|---|---|---|---|---|---|---|---|---|
| Fill Volume | 0.4 mL | | | | | | | | | | |
| Container/Closure | 2 mL Type 1 clear glass vial with a FluorTec® coated 4432/50 chlorobutyl stopper | | | | | | | | | | |
| Sucrose/Proline Concentration (% w/v) | FDG Lot Number | Color and Appearance[b] | Turbidity (Increase in OD at 405 nm) | pH | % Protein Recovered by RP-UPLC | Change in Purity by SE-UPLC[c] | | | Change in Charge Variants by CEX-UPLC[c] | | |
| | | | | | | % HMW | % Monomer | % LMW | % Acidic | % Main | % Basic |
| 5%/0% | L12-741 | Pass | 0.00 | 6.1 | 108 | 0.1 | 0.0 | -0.1 | 0.6 | -0.1 | -0.6 |
| 3%/1% | L12-742 | Pass | 0.00 | 6.0 | 105 | 0.1 | 0.0 | 0.0 | 0.8 | -0.5 | -0.2 |
| 2%/1.3% | L12-743 | Pass | 0.01 | 6.0 | 105 | 0.1 | 0.0 | 0.0 | 0.6 | -0.6 | 0.0 |
| 0%/2% | L12-744 | Pass | 0.00 | 6.0 | 104 | 0.1 | -0.1 | 0.0 | 0.1 | -0.3 | 0.2 |
| 0%/0%[a] | L12-745 | Pass | 0.00 | 6.0 | 108 | 0.6 | -0.6 | -0.1 | 0.0 | 0.1 | -0.1 |

FIGURE 8

Table 9:

| Formulation | 150 mg/mL H4H1276S, 10 mM histidine, pH 6.0, 70 mM arginine-HCl, 0.1% polysorbate 80 or 175 mg/mL H4H1276S, 10 mM histidine, pH 6.0, 70 mM arginine-HCl[a] | | | | | | | | | | |
| Fill Volume | 0.4 mL | | | | | | | | | | |
| Container/Closure | 2 mL Type 1 clear glass vial with a FluorTec® coated 4432/50 chlorobutyl stopper | | | | | | | | | | |

| Sucrose/Proline Concentration (% w/v) | FDG Lot Number | Color and Appearance[b] | Turbidity (Increase in OD at 405 nm) | pH | % Protein Recovered by RP-UPLC | Change in Purity by SE-UPLC[c] | | | Change in Charge Variants by CEX-UPLC[c] | | |
|---|---|---|---|---|---|---|---|---|---|---|---|
| | | | | | | % HMW | % Monomer | % LMW | % Acidic | % Main | % Basic |
| 5%/0% | L12-741 | Pass | 0.01 | 6.1 | 103 | 2.7 | -2.7 | 0.0 | 16.0 | -17.2 | 1.2 |
| 3%/1% | L12-742 | Pass | 0.01 | 6.1 | 104 | 2.8 | -2.8 | 0.0 | 16.7 | -17.8 | 1.2 |
| 2%/1.3% | L12-743 | Pass | 0.02 | 6.1 | 99 | 2.9 | -2.9 | 0.0 | 16.6 | -18.0 | 1.4 |
| 0%/2% | L12-744 | Pass | 0.02 | 6.1 | 102 | 3.3 | -3.3 | 0.0 | 16.5 | -17.5 | 1.0 |
| 0%/0%[a] | L12-745 | Pass | 0.02 | 6.1 | 100 | 3.8 | -3.8 | 0.0 | 15.0 | -16.1 | 1.2 |

FIGURE 9

Table 10:

| Formulation | 150 mg/mL H4H1276S, 10 mM histidine, pH 6.0, 70 mM arginine-HCl, 0.1% (w/v) polysorbate 80 | | | | | | | | | | |
| --- | --- | --- | --- | --- | --- | --- | --- | --- | --- | --- | --- |
| Fill Volume | 1 mL | | | | | | | | | | |
| Container/Closure | 5 mL Nalge-Nunc gamma-irradiated polycarbonate vial with silicone lined closure | | | | | | | | | | |

| Sucrose/Proline Concentration (% w/v) | FDG Lot Number | Color and Appearance[a] | Turbidity (Increase in OD at 405 nm) | pH | % Protein Recovered by RP-UPLC | Change in Purity by SE-UPLC[b] | | | Change in Charge Variants by CEX-UPLC[b] | | |
| --- | --- | --- | --- | --- | --- | --- | --- | --- | --- | --- | --- |
| | | | | | | % HMW | % Monomer | % LMW | % Acidic | % Main | % Basic |
| 5% Sucrose | L12-967 | Pass | 0.00 | 6.0 | 105 | 0.0 | 0.1 | 0.0 | -0.1 | -2.7 | 2.8 |
| 3% Proline | L12-969 | Pass | 0.01 | 6.0 | 106 | 0.1 | -0.1 | 0.0 | -1.1 | -2.9 | 4.0 |

FIGURE 10

Table 11:

| Formulation | 150 mg/mL H4H1276S, 10 mM histidine, pH 6.0, 70 mM arginine-HCl, 0.1% (w/v) polysorbate 80 |
|---|---|
| Fill Volume | 1.1 mL |
| Container/Closure | 2 mL Type 1 clear glass vial with a FluroTec® coated 4432/50 chlorobutyl stopper |

| Sucrose/ Proline Concentration (% w/v) | FDG Lot Number | Color and Appearance[a] | Turbidity (Increase in OD at 405 nm) | pH | % Protein Recovered by RP-UPLC | Change in Purity by SE-UPLC[b] | | | Change in Charge Variants by CEX-UPLC[b] | | |
|---|---|---|---|---|---|---|---|---|---|---|---|
| | | | | | | % HMW | % Monomer | % LMW | % Acidic | % Main | % Basic |
| 5% Sucrose | L12-967 | Pass | 0.00 | 6.0 | 101 | 0.4 | -0.5 | 0.1 | 1.9 | -4.6 | 2.7 |
| 3% Proline | L12-969 | Pass | 0.00 | 6.0 | 100 | 0.4 | -0.5 | 0.1 | 2.2 | -5.3 | 3.1 |

Particle Analysis by MFI (# per mL)[c]

| | | t=0 | | | 5°C 36 months | | |
|---|---|---|---|---|---|---|---|
| | | 2-10 µm | ≥10 µm | ≥25 µm | 2-10 µm | ≥10 µm | ≥25 µm |
| 5% Sucrose | L12-967 | 599 | 62 | 18 | 1173 | 71 | 7 |
| 3% Proline | L12-969 | 405 | 14 | 2 | 1203 | 71 | 4 |

H4H1276S Concentration (mg/mL)

Viscosity at 20°C (cPoise)

— 10 mM histidine, 70 mM arginine-HCl, 5% sucrose, 0.1% polysorbate 80, pH 6

— 10 mM histidine, 70 mM arginine-HCl, 3% proline, 0.1% polysorbate 80, pH 6

H4H1276S Concentration (mg/mL)

H4H1276S Concentration (mg/mL)

FIGURE 16A
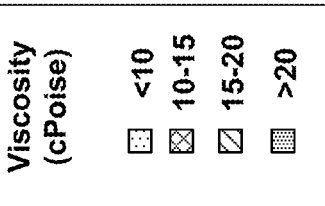
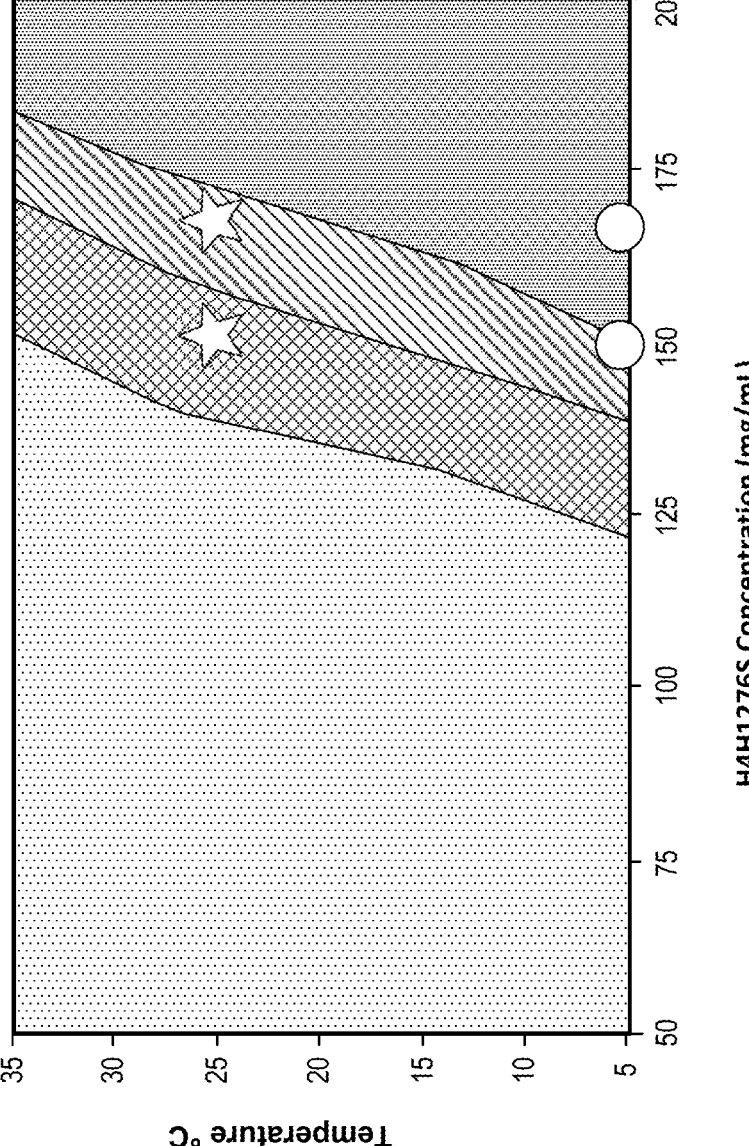

STABILIZED FORMULATIONS CONTAINING ANTI-ANGPTL3 ANTIBODIES

CROSS-REFERENCE TO RELATED APPLICATIONS

This application claims the benefit under 35 U.S.C. § 119(e) of U.S. provisional application No. 62/852,643 filed on May 24, 2019. The disclosure of the aforementioned application is herein incorporated by referenced in its entirety.

SEQUENCE LISTING

This application includes a Sequence Listing in electronic format entitled "40848-0092USU1-SeqList" which was created May 22, 2020 and which has a size of 107 kilobytes (KB) (107,000 bytes). The contents of the txt file "40848-0092USU1-SeqList" are incorporated by reference herein.

FIELD OF THE INVENTION

The present invention relates to the field of therapeutic antibody formulations. More specifically, the present invention relates to the field of pharmaceutical formulations comprising a human antibody that specifically binds to human angiopoietin-like (protein) 3 (ANGPTL3).

BACKGROUND OF THE INVENTION

Therapeutic macromolecules (e.g., antibodies) must be formulated in a manner that not only makes the molecules suitable for administration to patients, but also maintains their stability during storage and subsequent use. For example, therapeutic antibodies in liquid solution are prone to degradation, aggregation, or undesired chemical modifications, unless the solution is properly formulated. The stability of an antibody in liquid formulation depends not only on the kinds of excipients used in the formulation, but also on the amounts and proportions of the excipients relative to one another. Furthermore, other considerations aside from stability must be taken into account when preparing a liquid antibody formulation. Examples of such additional considerations include the viscosity of the solution and the concentration of antibody that can be accommodated by a given formulation, as well as the visual quality or appeal of the formulation. Thus, when formulating a therapeutic antibody, great care must be taken to arrive at a formulation that remains stable, contains an adequate concentration of antibody, and possesses a suitable viscosity, as well as other properties that enable the formulation to be conveniently administered to patients.

Antibodies to angiopoietin-like protein 3 (ANGPTL3) are one example of a therapeutically relevant macromolecule that requires proper formulation. Anti-ANGPTL3 antibodies are clinically useful for the treatment of diseases or disorders associated with lipid metabolism, cardiovascular diseases or disorders, and diseases or disorders associated with angiogenesis.

The amino acid and nucleotide sequences of human ANGPTL3 are shown in SEQ ID NOS:161 and 162, respectively. Exemplary anti-ANGPTL3 antibodies are described, for example, in U.S. Pat. No. 9,018,356B2, WO2008/073300, and U.S. Pat. No. 7,935,796.

Although anti-ANGPTL3 antibodies are known, there remains a need in the art for novel pharmaceutical formulations comprising such antibodies that are sufficiently stable and suitable for administration to patients.

BRIEF SUMMARY OF THE INVENTION

For many commercialized monoclonal antibodies, the final product presentation is dictated by the administration method. One such method is based on patients' preference for self-administration and less frequent dosing. Self-administration of a subcutaneous injection is one preferred means of administering parenteral products developed for the long-term treatment of many diseases. Subcutaneous (SC) injections necessitate dosing in $\leq 2$ mL total volume, preferably $\leq 1$ mL total volume. Less frequent dosing requires a higher concentration of drug per dose and, consequently, a higher protein concentration formulation. Thus, to enable less frequent dosing, high concentrations of drug ($>150$ mg per dose) that can be delivered in 1 mL are desired. High concentration formulations also enable smaller dosing volumes. For example, to deliver 15 mg/kg of drug to a 100 kg patient, i.e. 1500 mg of drug, 150 mL of a 10 mg/mL formulation is needed, whereas only 10 mL of a 150 mg/mL formulation is needed. Thus, high concentration formulations are preferred for the small injection volumes they enable.

It is important to consider both the stability and the viscosity of this higher protein concentration formulation. Because the relationship between protein concentration and viscosity is exponential, small differences in protein concentration may have large effects on viscosity and impact the ability of the patient to deliver the drug. The steepness of the curve depicting viscosity (y-axis) in relation to protein concentration (x-axis) can be affected by the addition of excipients, especially ones that increase (e.g., sugars) or decrease (e.g., salts) the viscosity and temperature. Furthermore, the viscosity is directly related to the ability to deliver the drug through a syringe. The sustaining force is the required force to continuously dispense the contents of a pre-filled syringe. It is measured using a Syringe Force Tester (Instron). The relationship between sustaining force and viscosity is linear.

Self-administration with a pre-filled syringe or auto injector necessitates a formulation with low viscosity (typically less than about 20 cPoise). There is, thus, a need to identify viscosity-reducing excipients and evaluate their effect on the rheological properties and stability of antibody (specifically, anti-ANGPTL3 antibody) formulations. This data can be used to enable development of an amino acid-based high-concentration liquid formulation with acceptable viscosity that can be used in pre-filled syringes and device development.

The present invention satisfies the afore-mentioned need by providing stable pharmaceutical formulations comprising a fully human monoclonal antibody that specifically binds to human angiopoietin-like protein 3 (ANGPTL3). H4H1276S is a fully human monoclonal antibody that targets ANGPTL3, an important protein that inhibits lipoprotein lipase (LPL) when active. The inhibition of ANGPTL3 by H4H1276S restores LPL activity and promotes processing of triglycerides and VLDL. H4H1276S is, thus, potentially indicated for several disease pathways, including severe hypertriglyceridemia and homozygous familial hypercholesterolemia.

In one aspect, a stable high-concentration liquid pharmaceutical formulation of low viscosity is provided, comprising: (i) a human antibody that specifically binds to human angiopoietin-like protein 3 (ANGPTL3); (ii) a buffer; (iii) an organic cosolvent; and (iv) at least one viscosity modifier. In one embodiment, the stable high-concentration liquid pharmaceutical formulation further comprises at least one amino acid. In another embodiment, the formulation comprises a stabilizer. In another aspect, a stable high-concentration liquid pharmaceutical formulation of low viscosity is provided, comprising: (i) a human antibody that specifically binds to human angiopoietin-like protein 3 (ANGPTL3); (ii) a buffer; (iii) an organic cosolvent; and (iv) at least two viscosity modifiers. In one embodiment, the stable high-concentration liquid pharmaceutical formulation further comprises at least one amino acid. In another embodiment, the formulation comprises a stabilizer. The term "viscosity modifier" includes viscosity-reducing agents or excipients.

In various embodiments, the antibody is provided at a concentration from about 5±0.75 mg/mL to about 250±37.5 mg/mL. In one embodiment, the antibody is provided at a concentration of 12.5 mg/mL±1.85 mg/mL, or about 12.5 mg/mL. In another embodiment, the antibody is provided at a concentration of 25 mg/mL±3.75 mg/mL, or about 25 mg/mL. In another embodiment, the antibody is provided at a concentration of 50 mg/mL±7.5 mg/mL, or about 50 mg/mL. In another embodiment, the antibody is provided at a concentration of 100 mg/mL±15 mg/mL, or about 100 mg/mL. In one embodiment, the antibody is provided at a concentration of 150 mg/mL±22.5 mg/mL, or about 150 mg/mL. In another embodiment, the antibody is provided at a concentration of 165 mg/mL±24.75 mg/mL, or about 165 mg/mL. In another embodiment, the antibody is provided at a concentration of 175 mg/mL±26.25 mg/mL, or about 175 mg/mL. In another embodiment, the antibody is provided at a concentration of 200 mg/mL±30 mg/mL, or about 200 mg/mL.

In certain embodiments, the formulation comprises any one of the anti-ANGPTL3 antibodies disclosed in U.S. Pat. No. 9,018,356B2, incorporated herein in its entirety. In certain embodiments, the anti-ANGPTL3 antibody comprises (a) a heavy chain variable region (HCVR) comprising heavy chain complementarity determining regions 1, 2 and 3 (HCDR1-HCDR2-HCDR3) each comprising a sequence of SEQ ID NO: 68, SEQ ID NO: 70 and SEQ ID NO: 72, respectively; and (b) a light chain variable region (LCVR) comprising light chain complementarity determining regions 1, 2 and 3 (LCDR1-LCDR2-LCDR3) each comprising a sequence of SEQ ID NO: 76, SEQ ID NO: 78 and SEQ ID NO: 80, respectively. In one embodiment, the antibody comprises a HCVR comprising the amino acid sequence of SEQ ID NO: 66 and a LCVR comprising the amino acid sequence of SEQ ID NO: 74. In another embodiment, the antibody comprises a HCVR having at least about 90% sequence identity to SEQ ID NO: 66 and a LCVR having at least about 90% sequence identity to SEQ ID NO: 74. In still another embodiment, the antibody comprises a HCVR having at least about 95% sequence identity to SEQ ID NO: 66 and a LCVR having at least about 95% sequence identity to SEQ ID NO: 74.

In one embodiment, the pH of the liquid formulation is pH 6.0±0.5, pH 6.0±0.4, pH 6.0±0.3, pH 6.0±0.2, pH 6.0±0.1, pH 6.0±0.05, pH 6.0±0.01, or pH 6.0. In one embodiment, the pH of the liquid formulation is about pH 6.0±0.3.

In one embodiment, the buffer is histidine. In certain embodiments, the histidine is at a concentration of from 5 mM±1 mM to 50 mM±10 mM, preferably from 5 mM±1 mM to 25 mM±5 mM. In one embodiment, the histidine is at a concentration of 10 mM±2 mM or 10 mM±1 mM or about 10 mM. In another embodiment, the histidine is at a concentration of 20 mM±4 mM or 20 mM±2 mM or about 20 mM. In still another embodiment, the histidine is at a concentration of 40 nM±8 mM or 40 nM±4 mM or about 40 nM.

In certain embodiments, the organic cosolvent is a non-ionic polymer containing a polyoxyethylene moiety. In one embodiment, the organic solvent is a surfactant. In some embodiments, the organic cosolvent is any one or more of polysorbate, poloxamer 188 and polyethylene glycol 3350. In one embodiment, the organic cosolvent is polysorbate 80. In one embodiment, the organic cosolvent is polysorbate 20. In one embodiment, the organic cosolvent is at a concentration of from about 0.01%±0.005% to about 1%±0.5% "weight to volume" or "w/v", wherein, e.g., 0.1 g/ml=10% and 0.01 g/ml=1%. In certain embodiments, the organic solvent is polysorbate at a concentration of from 0.05%±0.025% to 0.5%±0.25% (w/v). In one embodiment, the organic cosolvent is polysorbate 80, which is at a concentration of 0.2%±0.1% w/v, or about 0.2%. In another embodiment, the organic cosolvent is polysorbate 80, which is at a concentration of 0.1%±0.05% w/v or about 0.1% w/v. In one embodiment, the organic cosolvent is polysorbate 20, which is at a concentration of 0.2%±0.1% w/v, or about 0.2%. In another embodiment, the organic cosolvent is polysorbate 20, which is at a concentration of 0.1%±0.05% w/v or about 0.1% w/v.

In certain embodiments, a stabilizer is included in the formulation. In one embodiment, the stabilizer is a sugar. In another embodiment, the sugar is sucrose. In various embodiments, the stabilizer is at a concentration of from 1%±0.2% w/v to 20%±4% w/v, from 5%±1% w/v to 15%±3% w/v, or from 1%±0.2% to 10%±2% w/v. In one embodiment, the stabilizer is sucrose at a concentration of 5%±1% w/v or about 5% w/v. In another embodiment, the stabilizer is sucrose at a concentration of 9%±1.8% w/v or about 9% w/v. In another embodiment, the stabilizer is sucrose at a concentration of 10%±2% w/v or about 10% w/v.

In one embodiment, at least one amino acid is included in the formulation. In one embodiment, the amino acid is L-proline. In certain embodiments, the amino acid is at a concentration of from 1%±0.2% to 5%±1% w/v. In one embodiment, the amino acid is proline at a concentration of 1.5%±0.3% or about 1.5%. In one embodiment, the amino acid is proline at a concentration of 3%±0.6%, or about 3%.

In one embodiment, the at least one viscosity modifier is an excipient selected from the group consisting of: Arginine-HCl, Sodium Chloride, Histidine-HCl, Sodium Acetate, Calcium Chloride, Magnesium Chloride, Calcium Acetate, and Magnesium Acetate. In one embodiment, the viscosity modifier is Arginine-HCl. In certain embodiments, the viscosity modifier is at a concentration of from 25 mM to about 75 mM. In one embodiment, the viscosity modifier is Arginine-HCl at a concentration of 50 mM to about 75 mM.

In certain embodiments, the viscosity of the liquid pharmaceutical formulation at 25° C. is less than or equal to about 20 cPoise±10%. In certain embodiments, the viscosity at 25° C. is between 1.0 cPoise±10% and 20 cPoise±10%. In certain embodiments, the viscosity of the liquid pharmaceutical formulation is ≤15 cPoise. In certain embodiments, the viscosity of the liquid pharmaceutical formulation is ≤20 cPoise. In certain embodiments, the viscosity of the liquid pharmaceutical formulation is ≤10 cPoise. In certain embodiments, the viscosity at 25° C. is 5 cPoise±10%, 6.0 cPoise±10%, 7.0 cPoise±10%, 7.1 cPoise±10%, 7.2 cPoise±10%, 7.9 cPoise±10%, 8.3 cPoise±10%, 9.0 cPoise±10%, 9.6 cPoise±10%, 10.0 cPoise±10%, 10.6 cPoise±10%, 11.4 cPoise±10%, 11.6 cPoise±10%, 11.8 cPoise±10%, 12.0 cPoise±10%, 13.0 cPoise±10%, 14.0 cPoise±10%, 15.0 cPoise±10%, or 16 cPoise±10%.

In one aspect, a stable liquid pharmaceutical formulation of low-viscosity is provided, comprising: (i) from 5±0.75 mg/ml to 250±37.5 mg/ml of a human antibody that specifically binds to human ANGPTL3; (ii) from 0 mM to 40±8 mM histidine; (iii) from 0% to 0.5%±0.25% (w/v) polysorbate 80; (iv) from 50±10 mM to 75±15 mM Arginine-HCl; and (v) from 0 to 5%±1% proline, at a pH of from about 5.3 to about 6.7; wherein the anti-ANGPTL3 antibody comprises a heavy chain variable region (HCVR) and a light chain variable region (LCVR) such that the HCVR/LCVR combination comprises heavy and light chain complementarity determining regions (HCDR1-HCDR2-HCDR3/LCDR1-LCDR2-LCDR3), which comprise the amino acid sequences of SEQ ID NOs: 68-70-72/SEQ ID NOs: 76-78-80, respectively. In one embodiment, the anti-ANGPTL3 antibody comprises a heavy chain variable region (HCVR) and light chain variable region (LCVR) comprising an amino acid sequence of SEQ ID NO: 66 and SEQ ID NO: 74, respectively. In certain embodiments, the anti-PD1 antibody comprises a Fc region elected from the group consisting of human IgG1, IgG2, IgG3, and IgG4 isotypes. In one embodiment, the antibody comprises a human IgG4 isotype.

In certain embodiments, a stable, low-viscosity liquid pharmaceutical formulation is provided, comprising: (i) from 5±0.75 mg/ml to 250±37.5 mg/ml of a human antibody that specifically binds to human ANGPTL3; (ii) from 0 mM to 40±8 mM histidine; (iii) from 0% to 0.5%±0.25% (w/v) polysorbate 80; (iv) from 50±10 mM to 75±15 mM Arginine-HCl; and (v) from 0 to 5%±1% proline, at a pH of from about 5.3 to about 6.7; wherein the anti-ANGPTL3 antibody comprises a HCVR and a LCVR, wherein the HCVR has at least about 90% sequence identity to SEQ ID NO: 66 and/or the LCVR has at least about 90% sequence identity to SEQ ID NO: 74.

In certain embodiments, a stable, low-viscosity liquid pharmaceutical formulation is provided, comprising: (i) from 5±0.75 mg/ml to 250±37.5 mg/ml of a human antibody that specifically binds to human ANGPTL3; (ii) from 0 mM to 40±8 mM histidine; (iii) from 0% to 0.5%±0.25% (w/v) polysorbate 80; (iv) from 50±10 mM to 75±15 mM Arginine-HCl; and (v) from 0 to 5%±1% proline, at a pH of from about 5.3 to about 6.7; wherein the anti-ANGPTL3 antibody comprises a HCVR and a LCVR, wherein the HCVR comprises an amino acid sequence of SEQ ID NO: 66 having no more than five amino acid substitutions, and wherein the LCVR comprises an amino acid sequence of SEQ ID NO: 74 having no more than two amino acid substitutions.

In certain embodiments, the formulations of any of the preceding aspects has an attribute selected from the group consisting of: (i) the formulation is stable to long-term storage at 25° C., 5° C., −20° C., −30° C. and −80° C., as described herein; (ii) the formulation is stable to agitation stress as described herein; (iii) the formulation is low-viscosity (viscosity less than about 20 cPoise, preferably less than about 15 cPoise); (iii) the formulation is stable even with up to ±50% variation in the formulation excipient concentrations, as described herein; (iv) the formulation is iso-osmolar to physiologic conditions; (iv) the formulation is stable to and compatible with subcutaneous delivery devices and procedures; and (v) the formulation is stable to long-term storage in a prefilled syringe.

In certain embodiments of this aspect, a stable liquid formulation is provided, comprising: (i) from 5±0.75 mg/ml to 250±37.5 mg/ml of a human antibody that specifically binds to human ANGPTL3; (ii) from 5 mM±1 mM to 20±4 mM histidine; (iii) from 0.05%±0.025% to 0.3%±0.15% (w/v) polysorbate 80; (iv) from 50±5 mM to 75±7.5 mM Arginine-HCl; and (v) from 1%±0.2% to 5%±1% proline, at a pH of about 6.0, wherein the antibody comprises a HCVR/LCVR comprising an amino acid sequence pair of SEQ ID NOs: 66/74. In one embodiment, the stable liquid formulation of this aspect has a viscosity less than about 20 cP. In another embodiment, the stable liquid formulation of this aspect has a viscosity less than about 15 cP.

In one embodiment of this aspect, the stable liquid formulation comprises (i) 50±7.5 mg/mL of an anti-ANGPTL3 antibody; (ii) 10±2 mM histidine; (iii) 0.1%±0.05% (w/v) polysorbate 80; (iv) 3%±0.6% proline; and (v) 70±5 mM Arginine-HCl, at a pH of 6.0±0.3, wherein the antibody comprises a HCVR/LCVR comprising an amino acid sequence pair of SEQ ID NOs: 66/74.

In another embodiment, the stable liquid formulation comprises (i) 100±15 mg/mL of an anti-ANGPTL3 antibody; (ii) 10±2 mM histidine; (iii) 0.1%±0.05% (w/v) (w/v) polysorbate 80; (iv) 3%±0.6% proline; and (v) 70±5 mM Arginine-HCl, at a pH of 6.0±0.3, wherein the antibody comprises a HCVR/LCVR comprising an amino acid sequence pair of SEQ ID NOs: 66/74.

In another embodiment, the stable liquid formulation comprises (i) 150±22.5 mg/mL of an anti-ANGPTL3 antibody; (ii) 10±2 mM histidine; (iii) 0.1%±0.05% (w/v) polysorbate 80; (iv) 70±5 mM Arginine-HCl; and (v) 3%±0.6% proline, at a pH of 6.0±0.3, wherein the antibody comprises a HCVR/LCVR comprising an amino acid sequence pair of SEQ ID NOs: 66/74. In one embodiment of the formulations disclosed herein, the viscosity is less than about 20 cPoise, in another embodiment, less than about 15 cPoise.

In another embodiment of this aspect, the stable liquid formulation comprises (i) 175±26.25 mg/mL of an anti-ANGPTL3 antibody; (ii) 10±2 mM histidine; (iii) 0.1%±0.05% (w/v) polysorbate 80; (iv) 70±5 mM Arginine-HCl; and (v) 3%±0.6% proline, at a pH of 6.0±0.3, wherein the antibody comprises a HCVR/LCVR comprising an amino acid sequence pair of SEQ ID NOs: 66/74.

In another embodiment of this aspect, the stable liquid formulation comprises (i) 200±30.00 mg/mL of an anti-ANGPTL3 antibody; (ii) 10±2 mM histidine; (iii) 0.1%±0.05% (w/v) polysorbate 80; (iv) 70±5 mM Arginine-HCl; and (v) 3%±0.6% proline, at a pH of 6.0±0.3, wherein the antibody comprises a HCVR/LCVR comprising an amino acid sequence pair of SEQ ID NOs: 66/74.

In one embodiment of the formulations disclosed herein, the formulation additionally comprises 5%±1% (w/v) sucrose.

In one embodiment, after storage of the formulation at 45° for 21 days, ≤about 95% of the antibody is native, and about 45% of the antibody is of the main charge form. In one embodiment, after storage of the formulation at 5° for 36 months, >about 98% of the antibody is native, and >about 55% of the antibody is of the main charge form. In one embodiment, after storage of the formulation at −20° for 9 months, >about 98% of the antibody is native, and >about 61% of the antibody is of the main charge form. In one embodiment, after storage of the formulation at −30° for 36 months, >about 98% of the antibody is native, and >about 56% of the antibody is of the main charge form.

The cation exchange chromatography elution profile of a monoclonal antibody generally includes three peaks: the early- and late-eluting peaks (the so-called acidic and basic variants, respectively), and the most abundant peak (in the middle) is called the main peak (or main charge form or variant).

In one aspect, a liquid pharmaceutical formulation of any of the preceding aspects is provided in a container. In one embodiment, the container is a polycarbonate vial. In another embodiment, the container is a glass vial. In one embodiment, the glass vial is a type 1 borosilicate glass vial with a fluorocarbon-coated butyl rubber stopper. In another embodiment, the container is a microinfuser. In another embodiment, the container is a syringe. In another embodiment, the container is a prefilled syringe. In one embodiment, the syringe comprises a fluorocarbon-coated plunger. In certain embodiments, the syringe is a 1 mL or 2.25 mL long glass syringe containing less than about 500 parts per billion of tungsten equipped with a 27-G needle, a fluorocarbon-coated butyl rubber stopper, and a latex-free, non-cytotoxic rubber tip cap. In one specific embodiment, the syringe is a 1 mL long glass syringe equipped with a 27-G thin wall needle, a FLUROTEC-coated 4023/50 rubber stopper, and a FM 27 rubber tip cap. In another specific embodiment, the syringe is a 1 mL or 3 mL plastic syringe fitted with a 27-G needle. In one embodiment, the plastic syringe is distributed by BECTON DICKINSON. In another embodiment, the container is a Type 1 clear glass with FluroTecr® coated 4432/50 chlorobutyl stopper.

In one aspect, a kit comprising a pharmaceutical composition of any one of the preceding aspects, a container, and instructions for use is provided. In one embodiment, the container is a prefilled syringe. In one embodiment, the syringe is a NUOVA OMPI 1 mL or 2.25 mL long glass syringe equipped with a 27-G thin wall needle, a FLURO-TEC-coated 4023/50 rubber stopper, and a FM 27 rubber tip cap.

In certain embodiments, the present invention provides a prefilled syringe comprising a stable liquid pharmaceutical formulation comprising: (i) from 5±0.75 mg/ml to 250±37.5 mg/ml of a human antibody that specifically binds to human ANGPTL3; (ii) from 5 mM±1 mM to 20±4 mM histidine; (iii) from 0.05%±0.025% to 0.3%±0.15% (w/v) polysorbate 80; (iv) from 50±10 mM to 75±15 mM Arginine-HCl; and (v) from 1%±0.2% to 5%±1% proline, at a pH of 6.0±0.3, wherein the antibody comprises a HCVR/LCVR comprising an amino acid sequence pair of SEQ ID NOs: 66/74; wherein the formulation has an attribute selected from the group consisting of: (i) ≥about 98% of the antibody is in native form after storage at 5° C. for 36 months; (ii) ≥about 55% of the antibody is the main charge variant after storage at 5° C. for 36 months; (iii) the formulation is stable to agitation stress wherein ≥98% of the antibody is in native form after 120 minutes of agitation stress in a clear glass vial.

In certain embodiments the present invention provides a stable liquid pharmaceutical formulation comprising: (i) from 5±0.75 mg/ml to 250±37.5 mg/ml of a human antibody that specifically binds to human ANGPTL3; (ii) from 5 mM±1 mM to 20±4 mM histidine; (iii) from 0.05%±0.025% to 0.3%±0.15% (w/v) polysorbate 80; (iv) from 50±10 mM to 75±15 mM Arginine-HCl; and (v) from 1%±0.2% to 5%±1% proline, at a pH of 6.0±0.3, wherein the antibody comprises a HCVR/LCVR comprising an amino acid sequence pair of SEQ ID NOs: 66/74; wherein the formulation has an attribute selected from the group consisting of: (i) the formulation is stable to and compatible for use in subcutaneous and/or intravenous delivery devices; (ii) the formulation is chemically and physically stable to dilution with standard diluents known in the art (e.g., 0.9% sodium chloride or 5% dextrose); (iii) the formulation is stable to prefilled syringe or auto-injector format; and (iv) the formulation is compatible with standard infusion pumps (e.g., peristaltic pump, fluid displacement pump).

Other embodiments will become apparent from a review of the ensuing detailed description.

BRIEF DESCRIPTION OF FIGURES

FIG. 2 shows a table summarizing the effect of pH on the stability of 150 mg/mL H4H1276S incubated at 45° for 28 days. [a.] A sample passes color and visual appearance if it is clear to slightly opalescent, essentially free from visible particulates, colorless to pale yellow. [b.] Reported as a change in purity relative to the starting material. The starting material (no incubation) contains ≥98.4% native peak by SE-UPLC and ≥62.7% main peak by CEX-UPLC in all 5 formulations. CEX-UPLC, cation exchange ultra performance liquid chromatography; FDG, Formulation Development Group; HMW, high molecular weight; LMW, low molecular weight; OD, optical density; RP-UPLC, reversed phase ultra performance liquid chromatography; SE-UPLC, size exclusion ultra performance liquid chromatography.

FIG. 3 shows a table summarizing the effect of polysorbate 80 concentration on the stability of 150 mg/mL H4H1276S following agitation (120 minutes of vortexing). [a.] Sample passes color and visual appearance if it is clear to slightly opalescent, essentially free from visible particulates, colorless to pale yellow. [b.] Reported as a change in purity relative to the starting material. The starting material (no incubation) contains ≥98.4% native peak by SE-UPLC and ≥62.7% main peak by CEX-UPLC in all 12 formulations. CEX-UPLC, cation exchange ultra performance liquid chromatography; FDG, Formulation Development Group; HMW, high molecular weight; LMW, low molecular weight; OD, optical density; RP-UPLC, reversed phase ultra performance liquid chromatography; SE-UPLC, size exclusion ultra performance liquid chromatography.

FIG. 4 shows a table summarizing the effect of polysorbate 80 concentration on the stability of 150 mg/mL H4H1276S following incubation at 45° for 28 days. [a.] Sample passes color and visual appearance if it is clear to slightly opalescent, essentially free from visible particulates, colorless to pale yellow. [b.] Reported as a change in purity relative to the starting material. The starting material (no incubation) contains ≥98.4% native peak by SE-UPLC and ≥62.7% main peak by CEX-UPLC in all 5 formulations. CEX-UPLC, cation exchange ultra performance liquid chromatography; FDG, Formulation Development Group; HMW, high molecular weight; LMW, low molecular weight; OD, optical density; RP-UPLC, reversed phase ultra performance liquid chromatography; SE-UPLC, size exclusion ultra performance liquid chromatography.

FIG. 5 shows a table summarizing the effect of polysorbate 80 concentration on subvisible particle formation for 150 mg/mL H4H1276S following agitation (120 minutes of vortexing) or incubation at 45° for 28 days. [a.] Data were filtered using an ECD (μm) ≥5.00, Aspect Ratio <0.85 and Ignore Edge Particle filter. CEX-UPLC, cation exchange ultra performance liquid chromatography; FDG, Formulation Development Group; HMW, high molecular weight; LMW, low molecular weight; OD, optical density; RP-UPLC, reversed phase ultra performance liquid chromatography; SE-UPLC, size exclusion ultra performance liquid chromatography.

FIG. 6 shows a table summarizing the effect of sucrose and proline on the stability of H4H1276S following incubation at −20° C. for nine months. [a.] Corresponds to 175 mg/mL H4H1276S, 10 mM histidine, pH 6.0, 70 mM arginine-HCl formulation. [b.] Sample passes color and visual appearance if it is clear to slightly opalescent, essentially free from visible particulates, colorless to pale yellow. [c.] Reported as a change in purity relative to the starting material. The starting material (no incubation) contains ≥98.4% native peak by SE-UPLC and ≥62.7% main peak by CEX-UPLC in all 5 formulations. CEX-UPLC, cation exchange ultra performance liquid chromatography; FDG, Formulation Development Group; HMW, high molecular weight; LMW, low molecular weight; OD, optical density; RP-UPLC, reversed phase ultra performance liquid chromatography; SE-UPLC, size exclusion ultra performance liquid chromatography.

FIG. 7 shows a table summarizing the effect of sucrose and proline on the stability of H4H1276S following eight freeze/thaw cycles. [a.] Corresponds to 175 mg/mL H4H1276S, 10 mM histidine, pH 6.0, 70 mM arginine-HCl formulation. [b.] Sample passes color and visual appearance if it is clear to slightly opalescent, essentially free from visible particulates, colorless to pale yellow. [c.] Reported as a change in purity relative to the starting material. The starting material (no incubation) contains ≥98.4% native peak by SE-UPLC and ≥62.7% main peak by CEX-UPLC in all 5 formulations. CEX-UPLC, cation exchange ultra performance liquid chromatography; FDG, Formulation Development Group; HMW, high molecular weight; LMW, low molecular weight; OD, optical density; RP-UPLC, reversed phase ultra performance liquid chromatography; SE-UPLC, size exclusion ultra performance liquid chromatography.

FIG. 8 shows a table summarizing the effect of sucrose and proline on the stability of H4H1276S following incubation at 45° for 21 days. [a.] Corresponds to 175 mg/mL H4H1276S, 10 mM histidine, pH 6.0, 70 mM arginine-HCl formulation. [b.] Sample passes color and visual appearance if it is clear to slightly opalescent, essentially free from visible particulates, colorless to pale yellow. [c.] Reported as a change in purity relative to the starting material. The starting material (no incubation) contains ≥98.4% native peak by SE-UPLC and ≥62.7% main peak by CEX-UPLC in all 5 formulations. CEX-UPLC, cation exchange ultra performance liquid chromatography; FDG, Formulation Development Group; HMW, high molecular weight; LMW, low molecular weight; OD, optical density; RP-UPLC, reversed phase ultra performance liquid chromatography; SE-UPLC, size exclusion ultra performance liquid chromatography.

FIG. 9 shows a table summarizing the effect of sucrose and proline on the stability of H4H1276S following incubation at −30° C. for 36 months. [a.] Sample passes color and visual appearance if it is clear to slightly opalescent, essentially free from visible particulates, colorless to pale yellow. [b.] Reported as a change in purity relative to the starting material. The starting material (no incubation) contains 98.8% native peak by SE-UPLC for both formulations and 59.2% main peak for the sucrose formulation and 60.0% main peak for the proline formulation, as determined by CEX-UPLC. CEX-UPLC, cation exchange ultra performance liquid chromatography; FDG, Formulation Development Group; HMW, high molecular weight; LMW, low molecular weight; OD, optical density; RP-UPLC, reversed phase ultra performance liquid chromatography; SE-UPLC, size exclusion ultra performance liquid chromatography.

FIG. 10 shows a table summarizing the effect of sucrose and proline on the stability of H4H1276S following incubation at 5° C. for 36 months. [a.] Sample passes color and visual appearance if it is clear to slightly opalescent, essentially free from visible particulates, colorless to pale yellow. [b.] Reported as a change in purity relative to the starting material. The starting material (no incubation) contains 98.8% native peak by SE-UPLC for both formulations and 59.2% main peak for the sucrose formulation and 60.0% main peak for the proline formulation, as determined by CEX-U PLC. [c.] The average of three independent samples is reported. CEX-UPLC, cation exchange ultra performance liquid chromatography; FDG, Formulation Development Group; HMW, high molecular weight; LMW, low molecular weight; OD, optical density; RP-UPLC, reversed phase ultra performance liquid chromatography; SE-U PLC, size exclusion ultra performance liquid chromatography.

In FIG. 13A, viscosity is measured for various excipients added to a base formulation, and the pH was adjusted for a few of the options. In FIG. 13B, viscosity is measured for various excipients added to a different base formulation.

In FIG. 15A, the relative increases in HMW and acidic species and viscosity are measured for formulations containing 70 mM Arg-HCl vs 25 mM Mg(OAc)$_2$ for various concentrations of sucrose and/or L-proline. In FIG. 15B, the frozen storage stability (−20° C.) is measured in terms of % HMW species over time.

FIGS. 16A and 16B are contour plots showing the temperature, H4H1276S concentration, and viscosity, as they relate to one another, for a formulation containing 10 mM histidine, pH 6, 70 mM Arg-HCl, and 3% (w/v) proline (FIG. 16A); and for a formulation containing 10 mM histidine, pH 6, 70 mM Arg-HCl, and 5% (w/v) sucrose (FIG. 16B).

DETAILED DESCRIPTION

Figure 1:
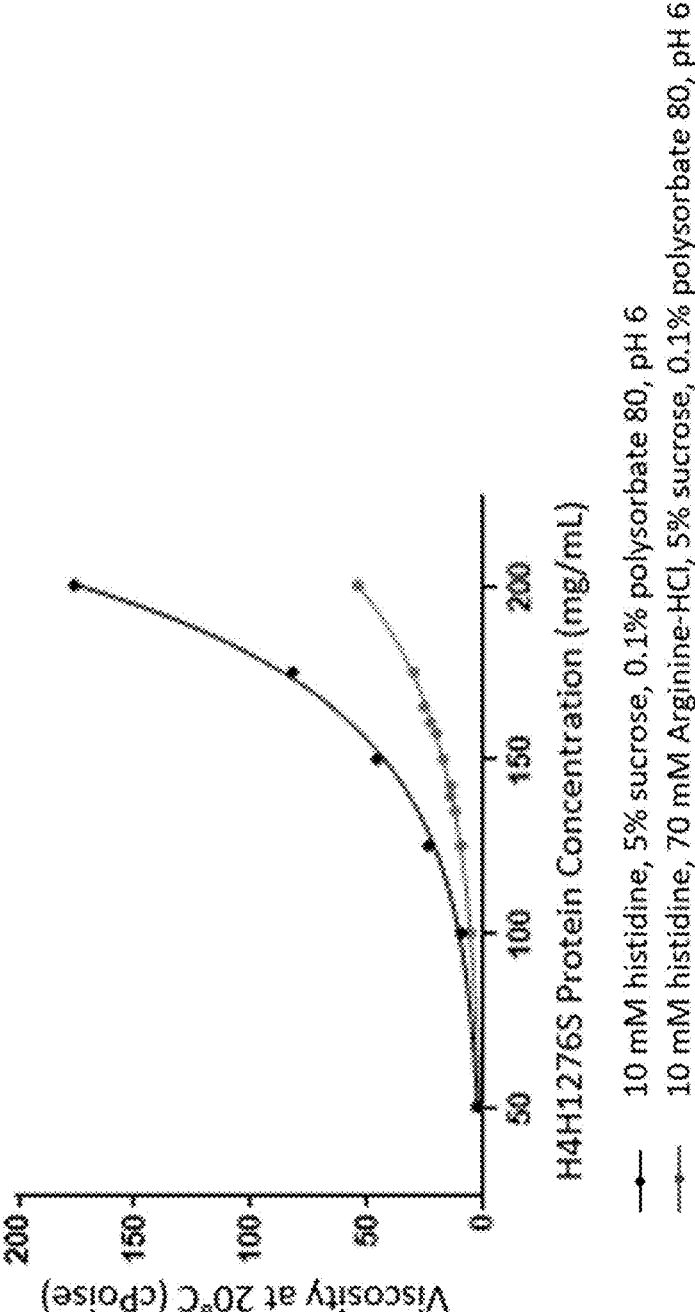
FIG. 1 graphically depicts the effect of H4H1276S concentration on viscosity.

Before the present formulations and methods are described, it is to be understood that this invention is not limited to particular formulations and methods, and experimental conditions described, as such formulations and methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about", when used in reference to a particular recited numerical value or range of values, means that the value may vary from the recited value by no more than 1%. For example, as used herein, the expression "about 100" includes 99 and 101 and all values in between (e.g., 99.1, 99.2, 99.3, 99.4, etc.). Although any methods and materials similar or equivalent to those described herein can be used in the practice or testing of the present invention, preferred methods and materials are now described. All publications mentioned herein are incorporated herein by reference in their entirety.

Definitions

As used herein, the expression "pharmaceutical formulation" means a combination of at least one active ingredient (e.g., a small molecule, macromolecule, compound, etc. which is capable of exerting a biological effect in a human or non-human animal), and at least one inactive ingredient, which, when combined with the active ingredient or one or more additional inactive ingredients, is suitable for therapeutic administration to a human or non-human animal. The term "formulation", as used herein, means "pharmaceutical formulation", unless specifically indicated otherwise. The present invention provides pharmaceutical formulations comprising at least one therapeutic polypeptide. According to certain embodiments of the present invention, the therapeutic polypeptide is an antibody, or an antigen-binding fragment thereof, which binds specifically to human angiopoietin-like protein 3 (ANGPTL3).

The term "human angiopoietin-like protein 3" or "hANGPTL3", as used herein, refers to ANGPTL3 having the nucleic acid sequence shown in SEQ ID NO:162 and the amino acid sequence of SEQ ID NO:161, or a biologically active fragment thereof.

The term "antibody", as used herein, is intended to refer to immunoglobulin molecules comprised of four polypeptide chains, two heavy (H) chains and two light (L) chains inter-connected by disulfide bonds. Each heavy chain is comprised of a heavy chain variable region (HCVR) and a heavy chain constant region ($C_H$; comprised of domains $C_H1$, $C_H2$ and $C_H3$). Each light chain is comprised of a light chain variable region (LCVR) and a light chain constant region (CO. The HCVR and LCVR can be further subdivided into regions of hypervariability, termed complementarity determining regions (CDR), interspersed with regions that are more conserved, termed framework regions (FR). Each HCVR and LCVR is composed of three CDRs and four FRs, arranged from amino-terminus to carboxy-terminus in the following order: FR1, CDR1, FR2, CDR2, FR3, CDR3, and FR4.

Substitution of one or more CDR residues or omission of one or more CDRs is also possible. Antibodies have been described in the scientific literature in which one or two CDRs can be dispensed with for binding. Padlan, et al. (1995 *FASEB J.* 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos, et al. 2002 *J Mol Biol* 320:415-428).

CDR residues not contacting antigen can be identified from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The term "human antibody", as used herein, is intended to include antibodies having variable and constant regions derived from human germline immunoglobulin sequences. The human mAbs of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include mAbs in which CDR sequences derived from the germline of another mammalian species (e.g., mouse), have been grafted onto human FR sequences.

The fully-human anti-hANGPTL3 antibodies disclosed herein may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The antibodies and antigen-binding fragments thereof described herein are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residues(s) (such sequence changes are referred to herein collectively as "germline mutations").

A person of ordinary skill in the art, starting with the heavy and light chain variable region sequences disclosed herein, can easily produce numerous antibodies and antigen-binding fragments that comprise one or more individual germline back-mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived).

Furthermore, the antibodies described herein may contain any combination of two or more germline mutations within the framework and/or CDR regions, e.g., wherein certain individual residues are mutated to the corresponding residues of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-ANGPTL3 antibodies comprising variants of any of the HCVR, LCVR, and/or CDR amino acid sequences disclosed herein having one or more conservative substitutions. For example, the present invention includes anti-ANGPTL3 antibodies having HCVR, LCVR, and/or CDR amino acid sequences with, e.g., 10 or fewer, 8 or fewer, 6 or fewer, 4 or fewer, 2 or 1, conservative amino acid substitution(s) relative to any of the HCVR, LCVR, and/or CDR amino acid sequences disclosed herein. In one embodiment, a HCVR comprises the amino acid sequence of SEQ ID NO:66 with 10 or fewer conservative amino acid substitutions therein. In another embodiment, a HCVR comprises the amino acid sequence of SEQ ID NO:66 with 8 or fewer conservative amino acid substitutions therein. In another embodiment, a HCVR comprises the amino acid sequence of SEQ ID NO:66 with 6 or fewer conservative amino acid substitutions therein. In another embodiment, a HCVR comprises the amino acid sequence of SEQ ID NO:66 with 4 or fewer conservative amino acid substitutions therein. In yet another embodiment, a HCVR comprises the amino acid sequence of SEQ ID NO:66 with 2 or 1 conservative amino acid substitution(s) therein. In one embodiment, a LCVR comprises the amino acid sequence of SEQ ID NO:74 with 10 or fewer conservative amino acid substitutions therein. In another embodiment, a LCVR comprises the amino acid sequence of SEQ ID NO:74 with 8 or fewer conservative amino acid substitutions therein. In another embodiment, a LCVR comprises the amino acid sequence of SEQ ID NO:74 with 6 or fewer conservative amino acid substitutions therein. In another embodiment, a LCVR comprises the amino acid sequence of SEQ ID NO:74 with 4 or fewer conservative amino acid substitutions therein. In yet another embodiment, a LCVR comprises the amino acid sequence of SEQ ID NO:74 with 2 or 1 conservative amino acid substitution(s) therein.

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-display antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR that is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or heterodimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

In certain embodiments, antibody or antibody fragments described herein may be conjugated to a therapeutic moiety ("immunoconjugate"), such as a cytotoxin, a chemotherapeutic drug, an immunosuppressant or a radioisotope.

The term "specifically binds," or the like, means that an antibody or antigen-binding fragment thereof forms a complex with an antigen that is relatively stable under physiological conditions. Specific binding can be characterized by an equilibrium dissociation constant ($K_D$) of about $1\times10^{-6}$ M or less (i.e., a smaller $K_D$ denotes a tighter binding). Methods for determining whether two molecules specifically bind are well known in the art and include, for example, equilibrium dialysis, surface plasmon resonance, and the like. An isolated antibody that specifically binds hANGPTL3 may, however, exhibit cross-reactivity to other antigens, such as ANGPTL3 molecules from other species, for example, cynomolgus monkey ANGPTL3, mouse ANGPTL3, rat ANGPTL3, and/or hANGPTL4. Moreover, multi-specific antibodies (e.g., bispecifics) that bind to hANGPTL3 and one or more additional antigens are nonetheless considered antibodies that "specifically bind" hANGPTL3, as used herein.

The term "$K_D$", as used herein, is intended to refer to the equilibrium dissociation constant of a particular antibody-antigen interaction.

An "isolated antibody", as used herein, is intended to refer to an antibody that is substantially free of other mAbs having different antigenic specificities (e.g., an isolated antibody that specifically binds hANGPTL3 is substantially free of mAbs that specifically bind antigens other than hANGPTL3). An isolated antibody that specifically binds hANGPTL3 may, however, have cross-reactivity to other antigens, such as ANGPTL3 molecules from other species, such as cynomolgus monkey, mouse, rat, and/or other related proteins, such as human ANGPTL4.

A "neutralizing", "blocking" or "abrogating" antibody, as used herein (or an antibody that "neutralizes", "blocks" or "abrogates" ANGPTL3 activity), is intended to refer to an antibody whose binding to ANGPTL3 results in direct inhibition of at least one biological activity of ANGPTL3, as assessed by standard in vitro assays known in the art. The terms, "neutralize", "inhibit", "block" and "abrogate", may be used herein interchangeably. A "non-blocking" antibody refers to an antibody whose binding to ANGPTL3 does not directly block a targeted activity of ANGPTL3 as assessed by standard in vitro assays, but yet may be an "interfering" antibody whose binding to ANGPTL3 results in indirect inhibition, reduction, attenuation, or other interference, of at least one biological activity of ANGPTL3 in vivo, e.g., by enhancing the clearance of ANGPTL3 from the circulation. Clearance of ANGPTL3 from the circulation can be particularly enhanced by a combination of at least two non-blocking antibodies. The neutralization, inhibition, abrogation, reduction, attenuation or interference, of a biological activity of ANGPTL3 can be assessed by measuring one or more indicators of ANGPTL3 biological activity by one or more of several standard in vitro or in vivo assays known in the art.

The term "surface plasmon resonance", as used herein, refers to an optical phenomenon that allows for the analysis of real-time biospecific interactions by detection of alterations in protein concentrations within a biosensor matrix, for example using the BIACORE™ system (Pharmacia Biosensor AB, Uppsala, Sweden and Piscataway, N.J.).

The term "epitope" is a region of an antigen that is bound by an antibody. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions that are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. See, e.g., Pearson (1994) Methods Mol. Biol. 24: 307-331. Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443 45. A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT, which can be used with default parameters to determine sequence homology or sequence identity between closely related polypeptides, such as homologous polypeptides from different species of organisms or between a wild type protein and a mutein thereof.

See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215: 403 410 and (1997) Nucleic Acids Res. 25:3389 402.

By the phrase "therapeutically effective amount" is meant an amount that produces the desired effect for which it is administered. The exact amount will depend on the purpose of the treatment, the age and the size of a subject treated, the route of administration, and the like, and will be ascertainable by one skilled in the art using known techniques (see, for example, Lloyd (1999) The Art, Science and Technology of Pharmaceutical Compounding).

Bioequivalents

The anti-hANGPTL3 antibodies and antibody fragments described herein encompass proteins having amino acid sequences that vary from those of the described mAbs, but that retain the ability to bind human ANGPTL3. Such variant mAbs and antibody fragments comprise one or more additions, deletions, or substitutions of amino acids when compared to parent sequence, but exhibit biological activity that is essentially equivalent to that of the described mAbs. Likewise, the anti-hANGPTL3 antibody-encoding DNA sequences described herein encompass sequences that comprise one or more additions, deletions, or substitutions of nucleotides when compared to the disclosed sequence, but that encode an anti-hANGPTL3 antibody or antibody fragment that is essentially bioequivalent to an anti-hANGPTL3 antibody or antibody fragment described herein. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives, if they are equivalent in the extent of their absorption but not in their rate of absorption and yet may be considered bioequivalent, because such differences in the rate of absorption are intentional and are reflected in the labeling, are not essential to the attainment of effective body drug concentrations on, e.g., chronic use, and are considered medically insignificant for the particular drug product studied. In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-hANGPTL3 antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation.

Antibodies that Bind Specifically to ANGPTL3

The pharmaceutical formulations of the present invention may comprise a human antibody, or an antigen-binding fragment thereof, that binds specifically to human angiopoietin-like protein 3 (ANGPTL3). Exemplary anti-human ANGPTL3 antibodies that may be included in the pharmaceutical formulations of the present invention are set forth in patent application publications U.S. Pat. No. 9,018,356B2, WO2008/073300, and U.S. Pat. No. 7,935,796, the disclosures of which are incorporated by reference in their entirety.

In certain embodiments, the anti-ANGPTL3 antibodies comprise HCVR/LCVR amino acid sequence pairs having SEQ ID NOs selected from the group consisting of 2/10 ("H4H1248P"), 18/26 ("H4H1250P"), 34/42 ("H4H1263S"), 50/58 ("H4H1268S"), 66/74 ("H4H1276S"), 82/90 ("H4H1279P"), 98/106 ("H4H1282P"), 114/122 ("H4H1292P"), 130/138 ("H4H1295P"), 146/154 ("H4H1296P"), and 180/188 ("H1M896N").

According to certain embodiments of the present invention, the anti-human ANGPTL3 antibody, or antigen-binding fragment thereof, comprises a heavy chain complementary determining region (HCDR) 1 of SEQ ID NO: 68, an HCDR2 of SEQ ID NO: 70, and an HCDR3 of SEQ ID NO: 72. In certain embodiments, the anti-human ANGPTL3 antibody, or antigen-binding fragment thereof, comprises an HCVR of SEQ ID NO:66.

According to certain embodiments of the present invention, the anti-human ANGPTL3 antibody, or antigen-binding fragment thereof, comprises a light chain complementary determining region (LCDR) 1 of SEQ ID NO: 76, an LCDR2 of SEQ ID NO: 78, and an LCDR3 of SEQ ID NO: 80. In certain embodiments, the anti-human ANGPTL3 antibody, or antigen-binding fragment thereof, comprises an LCVR of SEQ ID NO: 74.

According to certain embodiments of the present invention, the anti-human ANGPTL3 antibody, or antigen-binding fragment thereof, comprises a HCVR having 90%, 95%, 98% or 99% sequence identity to SEQ ID NO: 66.

According to certain embodiments of the present invention, the anti-human ANGPTL3 antibody, or antigen-binding fragment thereof, comprises a LCVR having 90%, 95%, 98% or 99% sequence identity to SEQ ID NO: 74.

According to certain embodiments of the present invention, the anti-human ANGPTL3 antibody, or antigen-binding fragment thereof, comprises a HCVR comprising an amino acid sequence of SEQ ID NO: 66 having no more than 5 amino acid substitutions.

According to certain embodiments of the present invention, the anti-ANGPTL3 antibody, or antigen-binding fragment thereof, comprises a LCVR comprising an amino acid sequence of SEQ ID NO: 74 having no more than 2 amino acid substitutions.

Sequence identity may be measured by any method known in the art (e.g., GAP, BESTFIT, and BLAST).

The present invention also includes formulations comprising anti-ANGPTL3 antibodies, wherein the anti-ANGPTL3 antibodies comprise variants of any of the HCVR, LCVR and/or CDR amino acid sequences disclosed herein having one or more conservative amino acid substitutions. For example, the present invention includes formulations comprising anti-ANGPTL3 antibodies having HCVR, LCVR and/or CDR amino acid sequences with, e.g., 10 or fewer, 8 or fewer, 6 or fewer, 4 or fewer, etc. conservative amino acid substitutions relative to any of the HCVR, LCVR and/or CDR amino acid sequences disclosed herein.

In certain embodiments, the anti-ANGPTL3 antibody comprises a Fc region elected from the group consisting of human IgG1, IgG2, IgG3, and IgG4 isotypes.

The non-limiting, exemplary antibody used in the Examples herein is referred to as "H4H1276S" or "mAb1". This antibody is also referred to in U.S. Pat. No. 9,018, 356B2 as H4H1276S. mAb1 (H4H1276S) comprises an HCVR/LCVR amino acid sequence pair having SEQ ID NOs: 66/74, and HCDR1-HCDR2-HCDR3/LCDR1-LCDR2-LCDR3 domains represented by SEQ ID NOs: 68-70-72/SEQ ID NOs: 76-78-80.

The full length sequences of H4H1276S are the following:

```
Heavy chain sequence
                                  (SEQ ID NO: 195)
EVQLVESGGGVIQPGGSLRLSCAASGFTFDDYAMNWVRQGPGKGLEWVSA

ISGDGGSTYYADSVKGRFTISRDNSKNSLYLQMNSLRAEDTAFFYCAKDL

RNTIFGVVIPDAFDIWGQGTMVTVSSASTKGPSVFPLAPCSRSTSESTAA

LGCLVKDYFPEPVTVSWNSGALTSGVHTFPAVLQSSGLYSLSSVVTVPSS

SLGTKTYTCNVDHKPSNTKVDKRVESKYGPPCPPCPAPEFLGGPSVFLFP

PKPKDTLMISRTPEVTCVVVDVSQEDPEVQFNWYVDGVEVHNAKTKPREE

QFNSTYRVVSVLTVLHQDWLNGKEYKCKVSNKGLPSSIEKTISKAKGQPR

EPQVYTLPPSQEEMTKNQVSLTCLVKGFYPSDIAVEWESNGQPENNYKTT

PPVLDSDGSFFLYSRLTVDKSRWQEGNVFSCSVMHEALHNHYTQKSLSLS

LGK

Light chain sequence
                                  (SEQ ID NO: 196)
DIQMTQSPSTLSASVGDRVTITCRASQSIRSWLAWYQQKPGKAPKLLIYK

ASSLESGVPSRFSGSGSGTEFTLTISSLQPDDFATYYCQQYNSYSYTFGQ

GTKLEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

The amount of antibody, or antigen-binding fragment thereof, contained within the pharmaceutical formulations of the present invention may vary depending on the specific properties desired of the formulations, as well as the particular circumstances and purposes for which the formulations are intended to be used. In certain embodiments, the pharmaceutical formulations are liquid formulations that may contain 5±0.75 mg/mL to 250±37.5 mg/mL of antibody; 10±1.5 mg/mL to 240±36 mg/mL of antibody; 20±3.0 mg/mL to 230±34.5 mg/mL of antibody; 25±3.75 mg/mL to 240±36 mg/mL of antibody; 50±7.5 mg/mL to 230±34.5 mg/mL of antibody; 60±9 mg/mL to 240±36 mg/mL of antibody; 70±10.5 mg/mL to 230±34.5 mg/mL of antibody; 80±12 mg/mL to 220±33 mg/mL of antibody; 90±13.5 mg/mL to 210±31.5 mg/mL of antibody; 100±15 mg/mL to 200±30 mg/mL of antibody; 110±16.5 mg/mL to 190±28.5 mg/mL of antibody; 120±18 mg/mL to 180±27 mg/mL of antibody; 130±19.5 mg/mL to 170±25.5 mg/mL of antibody; 140±21 mg/mL to 160±24 mg/mL of antibody; 150±22.5 mg/mL of antibody; or 175±26.25 mg/ml. For example, the formulations of the present invention may comprise about 5 mg/mL; about 10 mg/mL; about 15 mg/mL; about 20 mg/mL; about 25 mg/mL; about 30 mg/mL; about 35 mg/mL; about 40 mg/mL; about 45 mg/mL; about 50 mg/mL; about 55 mg/mL; about 60 mg/mL; about 65 mg/mL; about 70 mg/mL; about 75 mg/mL; about 80 mg/mL; about 85 mg/mL; about 90 mg/mL; about 95 mg/mL; about 100 mg/mL; about 105 mg/mL; about 110 mg/mL; about 115 mg/mL; about 120 mg/mL; about 125 mg/mL; about 130 mg/mL; about 135 mg/mL; about 140 mg/mL; about 145 mg/mL; about 150 mg/mL; about 155 mg/mL; about 160 mg/mL; about 165 mg/mL; about 170 mg/mL; about 175 mg/mL; about 180 mg/mL; about 185 mg/mL; about 190 mg/mL; about 195 mg/mL; about 200 mg/mL; about 205 mg/mL; about 210 mg/mL; about 215 mg/mL; about 220 mg/mL; about 225 mg/mL; about 230 mg/mL; about 235 mg/mL; about 240 mg/mL; about 245 mg/mL; or about 250 mg/mL of an antibody or an antigen-binding fragment thereof, that binds specifically to human ANGPTL3. In one embodiment, the formulation of the invention comprises about 150 mg/mL anti-human ANPTL3 antibody or antigen-binding fragment thereof.

Excipients and pH

The pharmaceutical formulations of the present invention comprise one or more excipients. The term "excipient", as used herein, means any non-therapeutic agent added to the formulation to provide a desired consistency, viscosity, or stabilizing effect.

In certain embodiments, the pharmaceutical formulation of the invention comprises at least one organic cosolvent in a type and in an amount that stabilizes the anti-hANGPTL3 antibody under conditions of rough handling or agitation, such as, e.g., vortexing. In some embodiments, what is meant by "stabilizes" is the prevention of the formation of more than 3% aggregated antibody of the total amount of antibody (on a molar basis) over the course of rough handling. In some embodiments, rough handling is vortexing a solution containing the antibody and the organic cosolvent for about 60 minutes or about 120 minutes.

In certain embodiments, the organic cosolvent is a non-ionic surfactant, such as an alkyl poly(ethylene oxide). Specific non-ionic surfactants that can be included in the formulations of the present invention include, e.g., polysorbates such as polysorbate 20, polysorbate 28, polysorbate 40, polysorbate 60, polysorbate 65, polysorbate 80, polysorbate 81, and polysorbate 85; poloxamers such as poloxamer 181, poloxamer 188, poloxamer 407; or polyethylene glycol (PEG). Polysorbate 20 is also known as TWEEN 20, sorbitan monolaurate and polyoxyethylenesorbitan monolaurate. Poloxamer 188 is also known as PLURONIC F68.

In certain embodiments, the organic cosolvent comprised in the formulation of the invention is polysorbate 80.

The amount of non-ionic surfactant contained within the pharmaceutical formulations of the present invention may vary depending on the specific properties desired of the formulations, as well as the particular circumstances and purposes for which the formulations are intended to be used. In certain embodiments, the formulations may contain 0.01%±0.005% to 0.5%±0.25% surfactant. For example, the formulations of the present invention may comprise about 0.005%; about 0.01%; about 0.02%; about 0.03%; about 0.04%; about 0.05%; about 0.06%; about 0.07%; about 0.08%; about 0.09%; about 0.1%; about 0.11%; about 0.12%; about 0.13%; about 0.14%; about 0.15%; about 0.16%; about 0.17%; about 0.18%; about 0.19%; about 0.20%; about 0.21%; about 0.22%; about 0.23%; about 0.24%; about 0.25%; about 0.26%; about 0.27%; about 0.28%; about 0.29%; about 0.30%; about 0.35%; about 0.40%; about 0.45%; about 0.46%; about 0.47%; about 0.48%; about 0.49%; about 0.50%; about 0.55%; or about 0.575% polysorbate 20 or polysorbate 80. In certain embodiments, the formulation of the invention comprises about 0.1% (w/v) polysorbate 80.

The pharmaceutical formulations of the present invention may also comprise one or more stabilizers in a type and in an amount that stabilizes the anti-hANGPTL3 antibody under conditions of thermal stress. In some embodiments, what is meant by "stabilizes" is that some significant % of the antibody in a native conformation when the solution containing the antibody and the thermal stabilizer is kept at about 45° C. for up to about 28 days. In some embodiments, what is meant by "stabilizes" is wherein some insignificant % of the antibody is aggregated when the solution containing the antibody and the thermal stabilizer is kept at about 45° C. for up to about 28 days. As used herein, "native" means the major form of the antibody by size exclusion, which is generally an intact monomer of the antibody. The term "native" also refers to non-aggregated and non-degraded form of the antibody.

In certain embodiments, the thermal stabilizer is a sugar such as sucrose, the amount of which contained within the formulation can vary depending on the specific circumstances and intended purposes for which the formulation is used. In certain embodiments, the formulations may contain about 1% to about 15% sugar; about 2% to about 14% sugar; about 3% to about 13% sugar; about 4% to about 12% sugar; about 5% to about 12% sugar; about 6% to about 11% sugar; about 7% to about 10% sugar; about 8% to about 11% sugar; or about 9% to about 11% sugar. For example, the pharmaceutical formulations of the present invention may comprise 4%±0.8%; 5%±1%; 6%±1.2%; 7%±1.4%; 8%±1.6%; 9%±1.8%; 10%±2%; 11%±2.2%; 12%±2.4%; 13%±2.6%; or about 14%±2.8% sugar (e.g., sucrose). In certain embodiments, the formulation of the invention does not comprise sugar.

The pharmaceutical formulations of the present invention may also comprise a buffer or buffer system, which serves to maintain a stable pH and to help stabilize the anti-hANGPTL3 antibody. In some embodiments, what is meant by "stabilizes" is minimizing the amount of the antibody aggregated when the solution containing the antibody and the buffer is kept at about 45° C. for up to about 28 days. In some embodiments, what is meant by "stabilizes" is maximizing the amount of antibody is in its native conformation as determined by size exclusion chromatography when the solution containing the antibody and the buffer is kept at about 45° C. for up to about 28 days. By "native" or "native conformation", what is meant is the antibody fraction that is not aggregated or degraded. This is generally determined by an assay that measures the relative size of the antibody entity, such as a size exclusion chromatographic assay. The non-aggregated and non-degraded antibody elutes at a fraction that equates to the native antibody, and is generally the main elution fraction. Aggregated antibody elutes at a fraction that indicates a size greater than the native antibody. Degraded antibody elutes at a fraction that indicates a size less than the native antibody.

In some embodiments, what is meant by "stabilizes" is wherein at least about 46% of the antibody is in its main charge form as determined by cation exchange chromatography when the solution containing the antibody and the buffer is kept at about 45° C. for up to about 28 days. By "main charge" or "main charge form", what is meant is the fraction of antibody that elutes from an ion exchange resin in the main peak, which is generally flanked by more "basic" peaks on one side and more "acidic" peaks on the other side.

The pharmaceutical formulations of the present invention may have a pH of from about 5.2 to about 6.4. For example, the formulations of the present invention may have a pH of about 5.5; about 5.6; about 5.7; about 5.8; about 5.9; about 6.0; about 6.1; about 6.2; about 6.3; about 6.4; or about 6.5. In some embodiments, the pH is 6.0±0.4; 6.0±0.3; 6.0±0.2; 6.0±0.1; about 6.0; or 6.0.

In some embodiments, the buffer or buffer system comprises at least one buffer that has a buffering range that overlaps fully or in part the range of pH 5.5-7.4. In certain embodiments, the buffer comprises a histidine buffer. In certain embodiments, the histidine is present at a concentration of 5 mM±1 mM to 15 mM±3 mM; 6 mM±1.2 mM to 14 mM±2.8 mM; 7 mM±1.4 mM to 13 mM±2.6 mM; 8 mM±1.6 mM to 12 mM±2.4 mM; 9 mM±1.8 mM to 11 mM±2.2 mM; 10 mM±2 mM; or about 10 mM. In certain embodiments, the buffer system comprises histidine at 10 mM±2 mM, at a pH of 6.0±0.3.

The pharmaceutical formulations of the present invention may also comprise one or more excipients that serve to maintain a reduced viscosity or to lower the viscosity of formulations containing a high concentration of anti-ANGPTL3 antibody drug substance (e.g., generally about 150 mg/ml of antibody). In certain embodiments, the at least one viscosity modifier is selected from the group consisting of: Arginine-HCl, Sodium Chloride, Histidine-HCl, Sodium Acetate (pH 5), Calcium Chloride, Magnesium Chloride, Calcium Acetate, and Magnesium Acetate. In certain embodiments, the formulations of the invention comprise Arginine HCl.

In certain embodiments, the pharmaceutical formulation includes at least one amino acid. In certain embodiments, the amino acid is proline, and the pharmaceutical formulation of the present invention contains proline, preferably as L-proline, at a concentration of 1%, 1.5%, 2%, 2.5%, 3%, 3.5%, 4%, 4.5% or 5%. In some embodiments, the formulation comprises proline in an amount sufficient to maintain the viscosity of the liquid formulation at less than 20±3 cPoise, less than 15±2.25 cPoise, or less than 11±1.65 cPoise. In some embodiments, the formulation comprises proline in an amount sufficient to maintain the viscosity at or below 15±2.25 cPoise. In certain embodiments, formulations may contain about 1% to about 5% proline; about 2% to about 4% proline; or about 3% proline. For example, the pharmaceutical formulations of the present invention may comprise 1%±0.2%; 1.5%±0.3%; 2%±0.4%; 2.5%±0.5%; 3%±0.6%; 3.5%±0.7%; 4%±0.8%; 4.5%±0.9%; or about 5%±1% proline.

During the antibody purification process it may be desired or necessary to exchange one buffer for another to achieve appropriate excipient concentrations, antibody concentration, pH, etc. Buffer exchange can be accomplished, e.g., by ultrafiltration/diafiltration (UF/DF) using, e.g., a semi-permeable tangential flow filtration membrane. Use of such techniques, however, has the potential to cause the Gibbs-Donnan effect [Bolton et al., 2011, Biotechnol. Prog. 27(1): 140-152]. The buildup of positive charge on the product side of the membrane during protein concentration is counter-balanced electrically by the preferential movement of positive ions to the opposite side of the membrane. The potential consequence of this phenomenon is that the final concentrations of certain components (e.g., histidine, L-proline, etc.) may be lower than the intended target concentrations of these components due to the electrostatic repulsion of positively charged diafiltration buffer excipients to the positively charged antibody protein during the UF/DF step. Thus, the present invention includes formulations in which the concentration of, e.g., histidine and/or L-proline vary from the recited amounts or ranges herein due to the Gibbs-Donnan effect.

Volume exclusion describes the behavior of highly concentrated samples in which a significant portion of the total volume of the solution is taken up by the solute, especially large molecules such as proteins, excluding the solvent from this space. This then decreases the total volume of solvent available for other solutes to be dissolved in, which may result in unequal partition across the ultrafiltration membrane. Thus, the present invention includes formulations in which the concentration of, e.g., histidine and/or L-proline may vary from the recited amounts or ranges herein due to the volume exclusion effect.

During the manufacture of the formulations of the present invention, variations in the composition of the formulation may occur. These variations may include the concentration of the active ingredient, the concentration of the excipients, and/or the pH of the formulation. Because changes in any of these parameters could potentially impact the stability or potency of the drug product, proven acceptable range (PAR) studies were conducted to assess whether variations in the composition, within the defined ranges, would impact the stability or potency of the antibody. Accordingly, the present invention includes formulations comprising anti-ANGPTL3 antibodies that are stable and retain potency with up to 50% variation in the excipient concentration. For example, included herein are anti-ANGPTL3 antibody formulations, wherein stability and potency of said formulations is unaffected by ±10%, ±20%, ±30%, ±40% or ±50% variation in the concentration of antibody, histidine, Arginine-HCl, and/or polysorbate.

Stability and Viscosity of the Pharmaceutical Formulations

The pharmaceutical formulations of the present invention typically exhibit high levels of stability. The term "stable", as used herein in reference to the pharmaceutical formulations, means that the antibodies within the pharmaceutical formulations retain an acceptable degree of chemical structure or biological function after storage under defined conditions. A formulation may be stable even though the antibody contained therein does not maintain 100% of its chemical structure or biological function after storage for a defined amount of time. Under certain circumstances, maintenance of about 90%, about 95%, about 96%, about 97%, about 98% or about 99% of an antibody's structure or function after storage for a defined amount of time may be regarded as "stable".

Stability can be measured, inter alia, by determining the percentage of native antibody that remains in the formulation after storage for a defined amount of time at a defined temperature. The percentage of native antibody can be determined by, inter alia, size exclusion chromatography (e.g., size exclusion ultra performance liquid chromatography [SE-UPLC]), such that native means non-aggregated and non-degraded. An "acceptable degree of stability", as that phrase is used herein, means that at least 90% of the native form of the antibody can be detected in the formulation after storage for a defined amount of time at a given temperature. In certain embodiments, at least about 90%, 91%, 92%, 93%, 94%, 95%, 96%, 97%, 98%, 99% or 100% of the native form of the antibody can be detected in the formulation after storage for a defined amount of time at a defined temperature. The defined amount of time after which stability is measured can be at least 14 days, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The defined temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., about 35° C., about 37° C., or about 45° C. For example, a pharmaceutical formulation may be deemed stable if after 6 months of storage at 5° C., greater than about 95%, 96%, 97% or 98% of native antibody is detected by SE-UPLC. A pharmaceutical formulation may also be deemed stable if after 6 months of storage at 25° C., greater than about 95%, 96%, 97% or 98% of native antibody is detected by SE-UPLC. A pharmaceutical formulation may also be deemed stable if after 28 days of storage at 45° C., greater than about 89%, 90%, 91%, 92%, 93%, 94%, 95% or 96% of native antibody is detected by SE-UPLC. A pharmaceutical formulation may also be deemed stable if after 12 months of storage at −20° C., greater than about 96%, 97%, or 98% of native antibody is detected by SE-UPLC. A pharmaceutical formulation may also be deemed stable if after 12 months of storage at −30° C., greater than about 96%, 97% or 98% of native antibody is detected by SE-UPLC. A pharmaceutical formulation may also be deemed stable if after 12 months of storage at −80° C., greater than about 96%, 97% or 98% of native antibody is detected by SE-UPLC.

Stability can be measured, inter alia, by determining the percentage of antibody that forms in an aggregate within the formulation after storage for a defined amount of time at a defined temperature, wherein stability is inversely proportional to the percent aggregate that is formed. The percentage of aggregated antibody can be determined by, inter alia, size exclusion chromatography (e.g., size exclusion ultra performance liquid chromatography [SE-UPLC]). An "acceptable degree of stability", as that phrase is used herein, means that at most 5% of the antibody is in an aggregated form (also denoted as the high molecular weight—HMW—form) detected in the formulation after storage for a defined amount of time at a given temperature. In certain embodiments an acceptable degree of stability means that at most about 5%, 4%, 3%, 2%, 1%, 0.5%, or 0.1% of the antibody can be detected in an aggregate in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., about 35° C., about 37° C. or about 45° C. For example, a pharmaceutical formulation may be deemed stable if after 12 months of storage at 5° C., less than about 2%, 1%, 0.5%, or 0.1% of the antibody is detected in an aggregated form. A pharmaceutical formulation may also be deemed stable if after three months of storage at 25° C., less than about 4%, 3%, 2%, 1%, 0.5%, or 0.1% of the antibody is detected in an aggregated form. A pharmaceutical formulation may also be deemed stable if after 28 days of storage at 45° C., less than about 10%, 9%, 8%, 7%, 6%, 5%, 4%, 3%, 2%, 1%, or 0.5%, of the antibody is detected in an aggregated form. A pharmaceutical formulation may also be deemed stable if after three months of storage at −20° C., −30° C., or −80° C. less than about 3%, 2%, 1%, 0.5%, or 0.1% of the antibody is detected in an aggregated form.

Stability can be measured, inter alia, by determining percentage of antibody that migrates in a more acidic fraction during ion exchange ("acidic form") than in the main fraction of antibody ("main charge form"), wherein stability is inversely proportional to the fraction of antibody in the acidic form. While not wishing to be bound by theory, deamidation of the antibody may cause the antibody to become more negatively charged and thus more acidic relative to the non-deamidated antibody (see, e.g., Robinson, N., Protein Deamidation, *PNAS*, Apr. 16, 2002, 99(8):5283-5288). The percentage of "acidified" antibody can be determined by, inter alia, ion exchange chromatography (e.g., cation exchange ultra performance liquid chromatography [CEX-UPLC]). An "acceptable degree of stability", as that phrase is used herein, means that at most 45% of the antibody is in a more acidic form detected in the formulation after storage for a defined amount of time at a defined temperature. In certain embodiments an acceptable degree of stability means that at most about 40%, 35%, 30%, 25%, 20%, 15%, 10%, 5%, 4%, 3%, 2%, 1%, 0.5%, or 0.1% of the antibody can be detected in an acidic form in the formulation after storage for a defined amount of time at a given temperature. In one embodiment, an acceptable degree of stability means that less than 30%, 25%, 20%, 15%, 10%, 5%, 4%, 3%, 2%, 1%, 0.5%, or 0.1% of the antibody can be detected in an acidic form in the formulation after storage for a defined amount of time at a given temperature. The defined amount of time after which stability is measured can be at least 2 weeks, at least 28 days, at least 1 month, at least 2 months, at least 3 months, at least 4 months, at least 5 months, at least 6 months, at least 7 months, at least 8 months, at least 9 months, at least 10 months, at least 11 months, at least 12 months, at least 18 months, at least 24 months, or more. The temperature at which the pharmaceutical formulation may be stored when assessing stability can be any temperature from about −80° C. to about 45° C., e.g., storage at about −80° C., about −30° C., about −20° C., about 0° C., about 4°-8° C., about 5° C., about 25° C., or about 45° C. For example, a pharmaceutical formulation may be deemed stable if after three months of storage at −80° C., −30° C., or −20° C. less than about 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after six months of storage at 5° C., less than about 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after six months of storage at 25° C., less than about 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody is in a more acidic form. A pharmaceutical formulation may also be deemed stable if after 28 days of storage at 45° C., less than about 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 10%, 9%, 8%, 7%, 6%, 5%, 4%, 3%, 2%, 1%, 0.5% or 0.1% of the antibody can be detected in a more acidic form.

Other methods may be used to assess the stability of the formulations of the present invention such as, e.g., differential scanning calorimetry (DSC) to determine thermal stability, controlled agitation to determine mechanical stability, and absorbance at about 350 nm or about 405 nm to determine solution turbidities. For example, a formulation of the present invention may be considered stable if, after 6 or more months of storage at about 5° C. to about 25° C., the change in $OD_{405}$ of the formulation is less than about 0.05 (e.g., 0.04, 0.03, 0.02, 0.01, or less) from the $OD_{405}$ of the formulation at time zero.

Measuring the biological activity or binding affinity of the antibody to its target may also be used to assess stability. For example, a formulation of the present invention may be regarded as stable if, after storage at e.g., 5° C., 25° C., 45° C., etc. for a defined amount of time (e.g., 1 to 12 months), the anti-ANGPTL3 antibody contained within the formulation binds to ANGPTL3 with an affinity that is at least 90%, 95%, or more of the binding affinity of the antibody prior to said storage. Binding affinity may be determined by e.g., ELISA or surface plasmon resonance. Biological activity may be determined by an ANGPTL3 activity assay, such as e.g., contacting a cell that expresses ANGPTL3 with the formulation comprising the anti-ANGPTL3 antibody. The binding of the antibody to such a cell may be measured directly, such as e.g., via FACS analysis. Alternatively, the downstream activity of the ANGPTL3 system may be measured in the presence of the antibody, and compared to the activity of the ANGPTL3 system in the absence of antibody. In some embodiments, the ANGPTL3 may be endogenous to the cell. In other embodiments, the ANGPTL3 may be ectopically expressed in the cell.

Additional methods for assessing the stability of an antibody in formulation are demonstrated in the Examples presented below.

The liquid pharmaceutical formulations of the present invention may, in certain embodiments, exhibit low to moderate levels of viscosity. "Viscosity" as used herein may be "kinematic viscosity" or "absolute viscosity". "Kinematic viscosity" is a measure of the resistive flow of a fluid under the influence of gravity. When two fluids of equal volume are placed in identical capillary viscometers and allowed to flow by gravity, a viscous fluid takes longer than a less viscous fluid to flow through the capillary. For example, if one fluid takes 200 seconds to complete its flow and another fluid takes 400 seconds, the second fluid is twice as viscous as the first on a kinematic viscosity scale. "Absolute viscosity", sometimes called dynamic or simple viscosity, is the product of kinematic viscosity and fluid density (Absolute Viscosity=Kinematic Viscosity×Density). The dimension of kinematic viscosity is $L^2/T$ where L is a length and T is a time. Commonly, kinematic viscosity is expressed in centistokes (cSt). The SI unit of kinematic viscosity is $mm^2/s$, which is 1 cSt. Absolute viscosity is expressed in units of centipoise (cP). The SI unit of absolute viscosity is the milliPascal-second (mPa-s), where 1 cP=1 mPa-s.

As used herein, a low level of viscosity, in reference to a fluid formulation of the present invention, will exhibit an absolute viscosity of less than about 20 cPoise (cP). For example, a fluid formulation of the invention will be deemed to have "low viscosity", if, when measured using standard viscosity measurement techniques, the formulation exhibits an absolute viscosity of about 20 cP, about 19 cP, about 18 cP, about 15 cP, about 12 cP, about 10 cP, about 9 cP, about 8 cP, or less. As used herein, a moderate level of viscosity, in reference to a fluid formulation of the present invention, will exhibit an absolute viscosity of between about 35 cP and about 20 cP. For example, a fluid formulation of the invention will be deemed to have "moderate viscosity", if when measured using standard viscosity measurement techniques, the formulation exhibits an absolute viscosity of about 34 cP, about 33 cP, about 32 cP, about 31 cP, about 30 cP, about 29 cP, about 28 cP, about 27 cP, about 26 cP, about 25 cP, about 24 cP, about 23 cP, about 22 cP, about 21 cP, about 20 cP, about 19 cP, 18 cP, about 17 cP, about 16 cP, or about 15.1 cP.

As illustrated in the examples below, the present inventors have made the surprising discovery that low viscosity liquid formulations comprising high concentrations of an anti-human ANGPTL3 antibody (e.g., from about 50 mg/ml up to at least 250 mg/mL) can be obtained by formulating the antibody with proline from about 1% to about 5% and without the need for a stabilizer like sucrose. Such formulations are stable to stress during handling and to storage at temperatures ranging from 45° C. to −80° C. (shown herein) and show viscosity below about 15 cP.

Exemplary Formulations

According to one aspect of the present invention, the pharmaceutical formulation is a stable, low viscosity, generally physiologically isotonic liquid formulation, which comprises: (i) a human antibody or antigen-binding fragment thereof that specifically binds to human ANGPTL3 (e.g., H4H1276S), at a concentration of about 25 to about 250 mg/mL; (ii) a buffer system that provides sufficient buffering at about pH 6.0±0.3; (iii) an organic cosolvent, which protects the structural integrity of the antibody; and (iv) a viscosity modifier that is a viscosity-reducing excipient. According to another aspect of the present invention, the pharmaceutical formulation is a stable, low viscosity, generally physiologically isotonic liquid formulation, which comprises: (i) a human antibody or antigen-binding fragment thereof that specifically binds to human ANGPTL3 (e.g., H4H1276S), at a concentration of about 25 to about 250 mg/mL; (ii) a buffer system that provides sufficient buffering at about pH 6.0±0.3; (iii) an organic cosolvent, which protects the structural integrity of the antibody; (iv) a viscosity modifier that is a viscosity-reducing excipient; and (iv) an amino acid, which serves to keep the viscosity manageable for injection in a convenient volume for subcutaneous administration.

According to one embodiment, the stable, low-viscosity pharmaceutical formulation comprises: (i) a human IgG4 antibody that specifically binds to human ANGPTL3, and which comprises an HCDR1 of SEQ ID NO: 68, an HCDR2 of SEQ ID NO: 70, an HCDR3 of SEQ ID NO: 72, an LCDR1 of SEQ ID NO: 76, an LCDR2 of SEQ ID NO: 78, and an LCDR3 of SEQ ID NO: 80, at a concentration of 25 mg/ml±7.5 mg/mL; (ii) histidine at 10 mM±2 mM, which buffers at pH 6.0±0.3; (iii) polysorbate 80 at 0.1% w/v±0.05% w/v; (iv) 70±5 mM Arginine-HCl; and (v) L-proline at about 3% (w/v)±0.6%. In another embodiment, the antibody comprises a HCVR/LCVR comprising an amino acid sequence pair of SEQ ID NOs: 66/74.

According to another embodiment, the stable, low-viscosity pharmaceutical formulation comprises (i) a human IgG4 antibody that specifically binds to human ANGPTL3, and which comprises an HCDR1 of SEQ ID NO: 68, an HCDR2 of SEQ ID NO: 70, an HCDR3 of SEQ ID NO: 72, an LCDR1 of SEQ ID NO: 76, an LCDR2 of SEQ ID NO: 78, and an LCDR3 of SEQ ID NO: 80, at a concentration of 50 mg/ml±7.5 mg/mL; (ii) 10±2 mM histidine; (iii) 0.1%±0.05% (w/v) polysorbate 80; (iv) 3%±0.6% proline; and (v) 70±5 mM Arginine-HCl, at a pH of 6.0±0.3. In another embodiment, the antibody comprises a HCVR/LCVR comprising an amino acid sequence pair of SEQ ID NOs: 66/74.

According to another embodiment, the stable, low-viscosity pharmaceutical formulation comprises (i) a human IgG4 antibody that specifically binds to human ANGPTL3, and which comprises an HCDR1 of SEQ ID NO: 68, an HCDR2 of SEQ ID NO: 70, an HCDR3 of SEQ ID NO: 72, an LCDR1 of SEQ ID NO: 76, an LCDR2 of SEQ ID NO: 78, and an LCDR3 of SEQ ID NO: 80, at a concentration of 100±15 mg/mL; (ii) 10±2 mM histidine; (iii) 0.1%±0.05% (w/v) (w/v) polysorbate 80; (iv) 3%±0.6% proline; and (v) 70±5 mM Arginine-HCl, at a pH of 6.0±0.3. In another embodiment, the antibody comprises a HCVR/LCVR comprising an amino acid sequence pair of SEQ ID NOs: 66/74.

According to another embodiment, the stable, low-viscosity pharmaceutical formulation comprises (i) a human IgG4 antibody that specifically binds to human ANGPTL3, and which comprises an HCDR1 of SEQ ID NO: 68, an HCDR2 of SEQ ID NO: 70, an HCDR3 of SEQ ID NO: 72, an LCDR1 of SEQ ID NO: 76, an LCDR2 of SEQ ID NO: 78, and an LCDR3 of SEQ ID NO: 80, at a concentration of 150±22.5 mg/mL; (ii) 10±2 mM histidine; (iii) 0.1%±0.05% (w/v) polysorbate 80; (iv) 70±5 mM Arginine-HCl; and (v) 3%±0.6% proline, at a pH of 6.0±0.3. In another embodiment, the antibody comprises a HCVR/LCVR comprising an amino acid sequence pair of SEQ ID NOs: 66/74. In certain embodiments of the formulations disclosed herein, the viscosity is less than about 20 cPoise; in further embodiments, the viscosity of the formulation is less than about 15 cPoise.

According to another embodiment, the stable, low-viscosity pharmaceutical formulation comprises (i) a human IgG4 antibody that specifically binds to human ANGPTL3, and which comprises an HCDR1 of SEQ ID NO: 68, an HCDR2 of SEQ ID NO: 70, an HCDR3 of SEQ ID NO: 72, an LCDR1 of SEQ ID NO: 76, an LCDR2 of SEQ ID NO: 78, and an LCDR3 of SEQ ID NO: 80, at a concentration of 175±26.25 mg/mL; (ii) 10±2 mM histidine; (iii) 0.1%±0.05% (w/v) polysorbate 80; (iv) 70±5 mM Arginine-HCl; and (v) 3%±0.6% proline, at a pH of 6.0±0.3. In another embodiment, the antibody comprises a HCVR/LCVR comprising an amino acid sequence pair of SEQ ID NOs: 66/74.

According to another embodiment, the stable, low-viscosity pharmaceutical formulation comprises (i) a human IgG4 antibody that specifically binds to human ANGPTL3, and which comprises an HCDR1 of SEQ ID NO: 68, an HCDR2 of SEQ ID NO: 70, an HCDR3 of SEQ ID NO: 72, an LCDR1 of SEQ ID NO: 76, an LCDR2 of SEQ ID NO: 78, and an LCDR3 of SEQ ID NO: 80, at a concentration of 200±30.00 mg/mL; (ii) 10±2 mM histidine; (iii) 0.1%±0.05% (w/v) polysorbate 80; (iv) 70±5 mM Arginine-HCl; and (v) 3%±0.6% proline, at a pH of 6.0±0.3. In another embodiment, the antibody comprises a HCVR/LCVR comprising an amino acid sequence pair of SEQ ID NOs: 66/74.

Additional non-limiting examples of pharmaceutical formulations encompassed by the present invention are set forth elsewhere herein, including the working Examples presented below.

Containers and Methods of Administration

The pharmaceutical formulations of the present invention may be contained within any container suitable for storage of medicines and other therapeutic compositions. For example, the pharmaceutical formulations may be contained within a sealed and sterilized plastic or glass container having a defined volume such as a vial, ampule, syringe, cartridge, or bottle. Different types of vials can be used to contain the formulations of the present invention including, e.g., clear and opaque (e.g., amber) glass or plastic vials. Likewise, any type of syringe can be used to contain or administer the pharmaceutical formulations of the present invention.

The pharmaceutical formulations of the present invention may be contained within "normal tungsten" syringes or "low tungsten" syringes. As will be appreciated by persons of ordinary skill in the art, the process of making glass syringes generally involves the use of a hot tungsten rod that functions to pierce the glass thereby creating a hole from which liquids can be drawn and expelled from the syringe. This process results in the deposition of trace amounts of tungsten on the interior surface of the syringe. Subsequent washing and other processing steps can be used to reduce the amount of tungsten in the syringe. As used herein, the term "normal tungsten" means that the syringe contains greater than or equal to 500 parts per billion (ppb) of tungsten. The term "low tungsten" means that the syringe contains less than 500 ppb of tungsten. For example, a low tungsten syringe, according to the present invention, can contain less than about 490, 480, 470, 460, 450, 440, 430, 420, 410, 390, 350, 300, 250, 200, 150, 100, 90, 80, 70, 60, 50, 40, 30, 20, 10 or fewer ppb of tungsten.

The rubber plungers used in syringes, and the rubber stoppers used to close the openings of vials, may be coated to prevent contamination of the medicinal contents of the syringe or vial, or to preserve their stability. Thus, pharmaceutical formulations of the present invention, according to certain embodiments, may be contained within a syringe that comprises a coated plunger, or within a vial that is sealed with a coated rubber stopper. For example, the plunger or stopper may be coated with a fluorocarbon film. Examples of coated stoppers or plungers suitable for use with vials and syringes containing the pharmaceutical formulations of the present invention are mentioned in, e.g., U.S. Pat. Nos. 4,997,423; 5,908,686; 6,286,699; 6,645,635; and 7,226,554, the contents of which are incorporated by reference herein in their entireties. Particular exemplary coated rubber stoppers and plungers that can be used in the context of the present invention are commercially available under the tradename "FluroTec®", available from West Pharmaceutical Services, Inc. (Lionville, PA). FluroTec® is an example of a fluorocarbon coating used to minimize or prevent drug product from adhering to the rubber surfaces.

According to certain embodiments of the present invention, the pharmaceutical formulations may be contained within a low tungsten syringe that comprises a fluorocarbon-coated plunger.

The pharmaceutical formulations can be administered to a patient by parenteral routes such as injection (e.g., subcutaneous, intravenous, intramuscular, intraperitoneal, etc.) or percutaneous, mucosal, nasal, pulmonary or oral administration. Numerous reusable pen or autoinjector delivery devices can be used to subcutaneously deliver the pharmaceutical formulations of the present invention. Examples include, but are not limited to AUTOPEN™ (Owen Mumford, Inc., Woodstock, UK), DISETRONIC™ pen (Disetronic Medical Systems, Bergdorf, Switzerland), HUMA-LOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (sanofi-aventis, Frankfurt, Germany). Examples of disposable pen or autoinjector delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), and the HUMIRA™ Pen (Abbott Labs, Abbott Park, IL).

The use of a microinfusor to deliver the pharmaceutical formulations of the present invention is also contemplated herein. As used herein, the term "microinfusor" means a subcutaneous delivery device designed to slowly administer large volumes (e.g., up to about 2.5 mL or more) of a therapeutic formulation over a prolonged period of time (e.g., about 10, 15, 20, 25, 30 or more minutes). See, e.g., U.S. Pat. Nos. 6,629,949; 6,659,982; and Meehan et al., *J. Controlled Release* 46:107-116 (1996). Microinfusors are particularly useful for the delivery of large doses of therapeutic proteins contained within high concentration (e.g., about 100, 125, 150, 175, 200 or more mg/mL) or viscous solutions.

In certain embodiments, the stable liquid pharmaceutical formulation of any of the preceding aspects is contained in a sterile glass vial and is administered as an IV infusion.

In one embodiment, the container is a 20 mL type 1 clear borosilicate glass vial. In certain embodiments, the container is a 2 mL or a 3 mL type 1 borosilicate glass vial with a FluroTec® coated 4432/50 butyl rubber stopper.

In one embodiment, the liquid pharmaceutical formulation of the present invention comprising about 25 mg/mL or 50 mg/mL of mAb1 is administered intravenously and may be contained in a glass vial.

In certain embodiments, the present invention provides an autoinjector comprising any of the liquid formulations described herein. In some embodiments, the present invention provides an autoinjector comprising a stable liquid formulation comprising about 50 mg/mL, about 100 mg/mL, about 150 mg/mL or about 175 mg/mL of mAb1, about 10 mM of histidine, at pH of about 6.0, about 70 mM Arginine-HCl, about 3% proline and about 0.1% polysorbate 80.

In certain embodiments, the present invention provides a pre-filled syringe comprising any of the liquid formulations described herein. In some embodiments, the present invention provides a prefilled syringe comprising a stable liquid formulation comprising about 50 mg/mL, about 100 mg/mL, about 150 mg/mL or about 175 mg/mL of mAb1, about 10 mM of histidine, at pH of about 6.0, about 70 mM Arginine-HCl, about 3% proline and about 0.1% polysorbate 80. In certain embodiments, the syringe is a 1 mL or 2.25 mL long glass syringe filled with a 27-gauge thin wall needle, a fluorocarbon coated rubber plunger and a rubber needle shield.

In one embodiment, a liquid pharmaceutical formulation containing about 175 mg/mL±26.25 mg/mL mAb1 is administered subcutaneously in a volume of approximately up to 2 mL in a prefilled syringe. In certain embodiments, the syringe is a 1 mL or 2.25 mL long glass syringe filled with a 27-gauge thin wall needle, a fluorocarbon coated rubber plunger and a rubber needle shield. In one embodiment, the syringe is an OMPI 1 mL long glass syringe fitted with a 27-gauge needle, a FM27 rubber needle shield, and a FLUROTEC® coated 4023/50 rubber plunger.

In one embodiment, the liquid pharmaceutical formulation containing about 150 mg/mL±22.5 mg/mL mAb1 is administered subcutaneously in a volume of about 1 to about 2 mL in a pre-filled syringe. In one embodiment, the syringe is a 1 mL or 2.25 mL long glass syringe filled with a 27-gauge thin wall needle, a fluorocarbon coated rubber plunger and a rubber needle shield. In one embodiment, the syringe is an OMPI 1 mL long glass syringe fitted with a 27-gauge needle, a FM27 rubber needle shield, and a FLUROTEC® coated 4023/50 rubber plunger.

Therapeutic Uses of the Pharmaceutical Formulations

The pharmaceutical formulations of the present invention are useful, inter alia, for the treatment, prevention, or amelioration of any disease or disorder associated with ANGPTL3 activity, including diseases or disorders mediated by ANGPTL3. The disease or disorder treatable using the formulations of the invention is any disease or condition which is improved, ameliorated, inhibited, or prevented, or its occurrence rate reduced, compared to that without anti-hANGPTL3 antibody treatment (e.g., ANGPTL3-mediated diseases or disorders), by removing, inhibiting, reducing, or otherwise interfering with, ANGPTL3 activity.

Examples of diseases or disorders treatable using the formulations of the invention include, but are not limited to, those involving lipid metabolism, such as hyperlipidemia, hyperlipoproteinemia and dyslipidemia, including atherogenic dyslipidemia, diabetic dyslipidemia, hypertriglyceridemia, including severe hypertriglyceridemia with TG >1000 mg/dL, hypercholesterolemia, chylomicronemia, mixed dyslipidemia (obesity, metabolic syndrome, diabetes, etc.), lipodystrophy, lipoatrophy, and the like, which are caused by, for example, decreased LPL activity and/or LPL deficiency, decreased LDL receptor (LDLR) activity and/or LDL receptor deficiency (e.g., homozygous familial hypercholesterolemia with LDLR$^{-/-}$), altered ApoC2, ApoE deficiency, increased ApoB, increased production and/or decreased elimination of very low-density lipoprotein (VLDL), certain drug treatment (e.g., glucocorticoid treatment-induced dyslipidemia), any genetic predisposition, diet, lifestyle, and the like. The formulations of the invention can also prevent or treat diseases or disorders associated with or resulting from hyperlipidemia, hyper-lipoproteinemia, and/or dyslipidemia, including, but not limited to, cardiovascular diseases or disorders, such as atherosclerosis, aneurysm, hypertension, angina, stroke, cerebrovascular diseases, congestive heart failure, coronary artery diseases, myocardial infarction, peripheral vascular diseases, and the like; acute pancreatitis; nonalcoholic steatohepatitis (NASH); blood sugar disorders, such as diabetes; obesity, and the like.

Other examples of diseases or disorders treatable using the formulations of the invention include cancer/tumor as well as non-neoplastic angiogenesis-associated diseases or disorders, including ocular angiogenic diseases or disorders, such as age-related macular degeneration, central retinal vein occlusion or branch retinal vein occlusion, diabetic retinopathy, retinopathy of prematurity, and the like, inflammatory diseases or disorders, such as arthritis, rheumatoid arthritis (RA), psoriasis, and the like.

EXAMPLES

The following examples are presented so as to provide those of ordinary skill in the art with a complete disclosure and description of how to make and use the methods and compositions of the invention and are not intended to limit the scope of what the inventors regard as their invention. Efforts have been made to ensure accuracy with respect to numbers used (e.g., amounts, temperature, etc.), but some experimental errors and deviations should be accounted for. Unless indicated otherwise, parts are parts by mole, molecular weight is average molecular weight, temperature is in degrees Centigrade, and pressure is at or near atmospheric pressure.

Example 1

Development of an Anti-ANGPTL3 Antibody Formulation

For later stage clinical development, both IV and SC administrations of higher doses were planned. Therefore, formulation development studies were conducted with the goal of developing a 150 mg/mL liquid formulation that can be used for either IV or SC injection. A high concentration liquid formulation is required for delivering doses of H4H1276S, up to 450 mg, with one or two SC injections. For IV administration, a high concentration liquid formulation is also advantageous, because it permits addition of a smaller volume of DP to the IV infusion bag. This supports the use of doses as high as 15 mg of H4H1276S per kg patient weight.

Initial formulation development activities for the lyophilized H4H1276S formulation were conducted at a low protein concentration (5-50 mg/mL H4H1276S) and included an assessment of buffers, pH, organic co-solvents, surfactants, and sucrose to identify excipients that enhance protein stability. With the knowledge gained from the initial formulation development, formulation development activities for the 150 mg/mL liquid formulation involved assessment of viscosity-reducing excipients, pH, surfactant, and thermal stabilizers to identify excipients that enhance protein stability at higher protein concentrations of between 150 and 200 mg/mL H4H1276S, while maintaining a solution with acceptable viscosity Throughout formulation development, three primary protein stress conditions (representing extreme handling conditions beyond which the antibody drug product would not be subjected during handling, manufacturing, shipping, storing, and labeling) were employed to develop and optimize the antibody formulations and to evaluate the effects of potential real-world stresses on the stability of the drug product. These stress conditions included:

Agitation (vortexing) of the protein solution at room temperature. Vortexing in glass vials exceeds the agitation that occurs during the handling and manufacturing of the protein.

Incubating the protein solution at elevated temperature (37° C., 40° C. or 45° C.) relative to the proposed DP storage condition (2° C.-8° C.).

Subjecting the protein to multiple freeze thaw cycles. Since the protein will undergo at least one freeze thaw cycle during the manufacture of DP, multiple freeze thaw cycles simulate and exceed the actual stress the protein is expected to experience.

Anti-ANGPTL3 antibodies: Anti-ANGPTL3 antibodies are described in U.S. Pat. No. 9,018,356 B2, incorporated herein in its entirety. The exemplary antibody used in the Examples below is a fully human anti-ANGPTL3 antibody H4H1276S (as disclosed in '356) comprising a heavy chain variable region/light chain variable region HCVR/LCVR amino acid sequence pair comprising SEQ ID NOs: 66/74; and heavy and light chain complementarity determining region CDR sequences comprising SEQ ID NOs: 68/70/72/76/78/80; and herein also referred to as "mAb1".

Example 2

Exemplary Formulations

In certain embodiments, mAb1 is formulated as an aqueous buffered formulation containing from 5 mg/ml±0.75 mg/ml to 250 mg/ml±45.0 mg/ml mAb1, 10 mM±2 mM histidine, 0.1%±0.05% w/v polysorbate, 50 to 75 mM Arginine-HCl, and 1%±0.02% to 5%±1% w/v proline, at pH 6.0±0.3. Exemplary formulations include: 150 mg/mL H4H1276S, 10 mM histidine, pH 6.0, 70 mM Arginine-HCl, 0.1% (w/v) polysorbate 80, and 3% (w/v) proline.

Example 3

Methods Used to Assess Formulation Stability

The physical stability of a formulation refers to properties such as color, appearance, pH, turbidity, and protein concentration. The chemical stability refers to the formation of high molecular weight (HMW) species, low molecular weight (LMW) species, charge variants, and other chemical modifications of the protein. The physical and chemical stabilities of antibody drug product (for example, H4H1276S) were assessed using the following assays:

Color and appearance by visual inspection (presence of visible particulates in solution can be detected)

pH

Turbidity measured by increase in optical density (OD) at 405 nm

Subvisible particulate analysis by Micro-Flow Imaging™ (MFI)

Protein concentration by reversed-phase ultra performance liquid chromatography (RP-UPLC), reported as percent protein recovery relative to the starting material Purity by the following assays:
Size exclusion ultra performance liquid chromatography (SE-UPLC)
Reduced and non-reduced microchip capillary electrophoresis sodium dodecyl sulfate (MCE-SDS)

Charge variant analysis:
Cation exchange UPLC (CEX-UPLC)
Imaged capillary isoelectric focusing (iCIEF)

Potency by Bioassay:
The relative potency of each sample is determined by a bioassay and is defined as: (IC50 Reference Sample/IC50 Sample)*100%. The measured potency of storage stability samples must be within 50% and 150% of the measured potency of the reference standard.

For the chemical stability of a formulation, the formation of covalently modified forms (e.g. covalent aggregates, cleavage products, or charge variant forms) and non-covalently modified forms (e.g. non-covalent aggregates) of protein is evaluated. Higher and lower molecular weight degradation products can be separated from native antibody by SE-UPLC and MCE-SDS methods.

Example 4

Selection of Viscosity-Reducing Agent

To understand how viscosity is affected by increasing concentrations of H4H1276S, formulations were prepared with different protein concentrations in 10 mM histidine, pH 6.0, 5% sucrose and 0.1% polysorbate 80. This formulation is equivalent to the first-in-human (FIH) formulation used for IV administration in initial clinical studies. The viscosity of each sample was measured at 20° C. and the results are shown in FIG. 1 (top curve). The measured viscosity at 150 mg/mL was greater than 40 centipoise (cP), which is significantly higher that the targeted acceptable viscosity of 20 cP. It was, thus, surmised that use of a viscosity-reducing excipient is required to achieve a formulation with a target protein concentration of 150 mg/mL and acceptable viscosity.

In order to identify a suitable viscosity-reducing excipient, the effect of selected excipients on the H4H1276S formulation viscosity was examined. The excipients included were arginine-HCl, sodium chloride, histidine-HCl, sodium acetate, calcium chloride, magnesium chloride, calcium acetate, and magnesium acetate. The addition of 70 mM arginine-HCl decreased the viscosity at all protein concentrations tested (FIG. 1, bottom curve). Arginine-HCl was found to be the most effective at reducing viscosity compared to the other excipients. Additionally, it had a minimal impact on stability. A summary of excipients tested for viscosity reduction is provided in Table 1, below. Arginine-HCl was selected for additional development studies, because it provided adequate reductions in viscosity. Subsequent formulation development studies included 70-75 mM arginine-HCl to determine the optimal pH, surfactant concentration, and thermal stabilizer.

TABLE 1

| Summary of Excipients Tested for Viscosity Reduction | | | |
| --- | --- | --- | --- |
| Excipient | Concentration Range | Effect on Viscosity | Effect on Stability |
| Arginine-HCl | 50-75 mM | Significant Reduction | Minimal |
| Sodium Chloride | 50-75 mM | Significant Reduction | Minimal |
| Histidine-HCl | 40-65 mM | Reduction | Not Tested |
| Sodium Acetate, pH 5 | 40-60 mM | Significant Reduction | Decreased Stability |
| Calcium Chloride | 25 mM | Significant Reduction | Minimal |
| Magnesium Chloride | 25 mM | Significant Reduction | Minimal |
| Calcium Acetate | 25 mM | Significant Reduction | Minimal |
| Magnesium Acetate | 25 mM | Significant Reduction | Minimal |

Example 5 pH Selection

The effect of pH on the thermal stability of H4H1276S was examined in liquid formulations by incubating 150 mg/mL H4H1276S at 45° C. for 28 days at varying pH ranges in 10 mM histidine with either 5% (w/v) sucrose or 2% (w/v) proline. Sucrose and proline were considered as the potential thermal stabilizer and were included, so that the effect of buffer and pH could be studied with a formulation composition that is more representative of the final formulation. Based on results from SE-UPLC and CEX-UPLC analysis (Table 2, as shown in FIG. 2), higher pH minimizes HMW species formation, while lower pH minimizes charge variant formation. Histidine buffer at a pH of 6.0 was selected as the formulation buffer, because it provided the best balance between HMW species formation and charge variant formation.

Example 6

Surfactant Concentration Optimization

Surfactants are often added to antibody formulations to protect the protein from agitation-induced aggregation. When developing the initial lyophilizable formulation, HMW species formation was observed when 50 mg/mL H4H1276S was agitated. Addition of 0.1% (w/v) polysorbate 80 protected H4H1276S from agitation-induced instability. However, protein concentration, thermal stabilizer content, and the presence of other excipients can affect a protein's susceptibility to agitation stress. Therefore, the minimum amount of polysorbate 80 needed to protect 150 mg/mL H4H1276S from agitation stress was evaluated. Polysorbate 80 concentrations of 0.0%, 0.02%, 0.05%, and 0.1% (% w/v) were examined in the presence of 5% sucrose, 2% sucrose and 1.3% proline, or 2% proline (% w/v). The samples were formulated in 10 mM histidine, pH 6, with 70 mM arginine to be more representative of the final formulation. The results are summarized in Tables 3, 4, and 5 (as shown in FIGS. 3, 4, and 5, respectively).

When agitated for 120 minutes (Table 3, as shown in FIG. 3), a significant increase in HMW species (4.8-6.3%) was observed for formulations without surfactant. Addition of 0.02% (w/v) polysorbate 80 was not sufficient to protect impacted by choice of thermal stabilizer. The addition of polysorbate 80 does not impact the formation of HMW species of H4H1276S when incubated at 45° C., regardless of thermal stabilizer included in the formation (Table 4, as shown in FIG. 4). The relative change in HMW species from t=0 for the formulations without thermal stabilizer was comparable to those with polysorbate. The increase in HMW species ranged from 3.1-3.2%, 3.5-3.8% and 3.8-4.1% for the sucrose only, sucrose and proline, or proline only formulations, respectively.

When comparing across thermal stabilizer groups, H4H1276S exhibited modestly improved stability when formulated with sucrose (compared to proline) and incubated under stress conditions. The difference, however, was not considered to be meaningful. The differences in total relative change in charge variant distribution from t=0 for all formulations evaluated is considered to be within assay variability. The impact of agitation and 45° C. incubation on particulate formation was evaluated using MFI, and the results are shown in Table 5 (as shown in FIG. 5). There was no discernable trend in particulate formation, suggesting that particulate formation is not impacted by the concentration of polysorbate 80 or thermal stabilizer included in the formulation. Although stabilization was achieved at 0.05% (w/v) polysorbate concentration, 0.1% (w/v) polysorbate 80 was selected as the surfactant concentration. The higher concentration of polysorbate ensures the robustness of the formulation, has equivalent stability as 0.05% (w/v) polysorbate formulation, and provides additional stabilization upon dilution into an IV bag.

Example 7

Effect of Thermal Stabilizer

Stabilizers can be added to antibody formulations to increase the stability of the protein in liquid formulations and during frozen storage. Sucrose was included as a thermal stabilizer in previous formulations. However, sucrose can also increase the viscosity of the solution. Therefore, proline was evaluated as a thermal stabilizer, in the hopes that it could influence the solubility and colloidal stability of protein to improve the storage stability of monoclonal antibody product formulation, without increasing the viscosity of the final formulation (Table 6, below).

TABLE 6

| | | | Viscosity at 20° C. for H4H1276S Formulations with Different Concentrations of Sucrose and Proline | | | | |
|---|---|---|---|---|---|---|---|
| | | | Formulation Composition | | | | |
| H4H1276S (mg/mL) | Histidine (mM) | pH | Polysorbate 80 (% w/v) | Arginine-HCl (mM) | Sucrose (% w/v) | Proline (% w/v) | Viscosity at 20° C. |
| 150 | 10 | 6 | 0.1 | 70 | 5 | 0 | 15.3 |
| 150 | 10 | 6 | 0.1 | 70 | 3 | 1 | 14.8 |
| 150 | 10 | 6 | 0.1 | 70 | 2 | 1.5 | 14.0 |
| 150 | 10 | 6 | 0.1 | 70 | 0 | 2 | 13.1 |

H4H1276S against agitation-induced instability, while 0.05% (w/v) polysorbate 80 and above provided adequate stabilization, regardless of thermal stabilizer included in the formulation. The data demonstrate that at least 0.05% (w/v) polysorbate 80 is required to protect H4H1276S from agitation-induced instability, and that with at least 0.05% (w/v) polysorbate 80, the agitation-induced instability is not To support selection of the components for the bulk formulated drug substance composition and to assess the need for the presence of a thermal stabilizer in the formulation, the stability of 175 mg/mL H4H1276S in 10 mM histidine, pH 6.0 and 70 mM arginine-HCl (no sucrose or proline) was evaluated by assessing frozen storage stability at −20° C. and freeze/thaw stability (frozen at −30° C. and thawed at room temperature) (Tables 7 and 8 (shown in FIGS. 6 and 7, respectively)). Although −30° C. is the intended long-term storage condition for formulated drug substance, frozen storage stability at −20° C. was evaluated as an accelerated frozen storage condition for development. A 7.2% increase in HMW species was observed following incubation at −20° C. for 9 months (Table 7, shown in FIG. 6). While a small increase in HMW species was observed for this formulation following 8 freeze/thaw cycles (Table 8, shown in FIG. 7), the −20° C. frozen storage stability data indicate the need for a thermal stabilizer to support long-term bulk drug substance frozen storage.

To identify and optimize the concentration of thermal stabilizer(s) in the liquid formulation, 150 mg/mL H4H1276S was formulated in 10 mM histidine, pH 6, 70 mM arginine-HCl, and 0.1% (w/v) polysorbate 80 and incubated at 45° C. with different concentrations of sucrose and proline to assess protein stability. The formulations were also incubated at −20° C. and subjected to freeze/thaw cycles (−30° C. freeze; room temperature thaw) to compare frozen storage stability, which is needed to support storage of the bulk formulated drug substance. Polysorbate 80 was included in these formulations to be more representative of the final product formulation. Viscosity at 20° C. was measured for all samples at t=0 and is summarized in Table 6, above. Table 6 illustrates that replacement of sucrose with proline decreases the viscosity in a concentration-dependent manner, indicating that formulations with proline may be advantageous for the final product, if there is no negative impact on stability.

H4H1276S exhibited modestly improved stability when formulated with sucrose compared to proline and incubated at 45° C. for 21 days (Table 9, shown in FIG. 8). The total relative change from t=0 for the formation of HMW species for the 5% sucrose formulation was 2.7%, whereas the total relative change from t=0 in HMW species for the 2% proline formulation was 3.3%. This difference is not considered to be meaningful. The differences in total relative change from t=0 for charge variants are considered to be within assay variability across the different formulations that were evaluated.

No meaningful change in any quality attribute was observed for all formulations containing sucrose and/or proline when incubated at −20° C. or subjected to 8 freeze/thaw cycles (−30° C. freeze; room temperature thaw) (Tables 7 and 8, shown in FIGS. 6 and 7). In summary, the proline-containing formulation exhibited a lower viscosity and comparable stability relative to the sucrose-containing formulation when stored under accelerated or stress storage conditions. Two lead formulations were selected based on these results: 1) 150 mg/mL H4H1276S, 10 mM histidine, pH 6.0, 70 mM arginine-HCl, 0.1% (w/v) polysorbate 80, and 5% (w/v) sucrose; and 2) 150 mg/mL H4H1276S, 10 mM histidine, pH 6.0, 70 mM arginine-HCl, 0.1% (w/v) polysorbate 80, and 3% (w/v) proline. The proline concentration was increased slightly to ensure adequate protein stability under representative long-term storage conditions.

Example 8

Formulation Selection

Long-term stability was examined to compare stability profiles for the two lead formulations (see Example 7, above). Stability data at −30° C. were collected to evaluate the long-term storage of bulk formulated drug substance (Table 10, shown in FIG. 9). Stability data at 5° C. were collected to evaluate the long-term storage of drug product (Table 11, shown in FIG. 10). The data indicate that equivalent stability profiles are obtained with both lead formulations.

The relationship between viscosity, protein concentration, and temperature was used to facilitate the selection of a formulation that would be deliverable at a range of protein concentrations and temperatures. The impact of protein concentration on the viscosity of the final formulation, and how excipients affect that relationship, were considered. Likewise, the temperature was considered, with a view to a) withdrawal and/or administration of the drug (about room temperature); b) bulk manufacturing process steps (typically about 15-25° C.); and c) storage.

Figure 11:
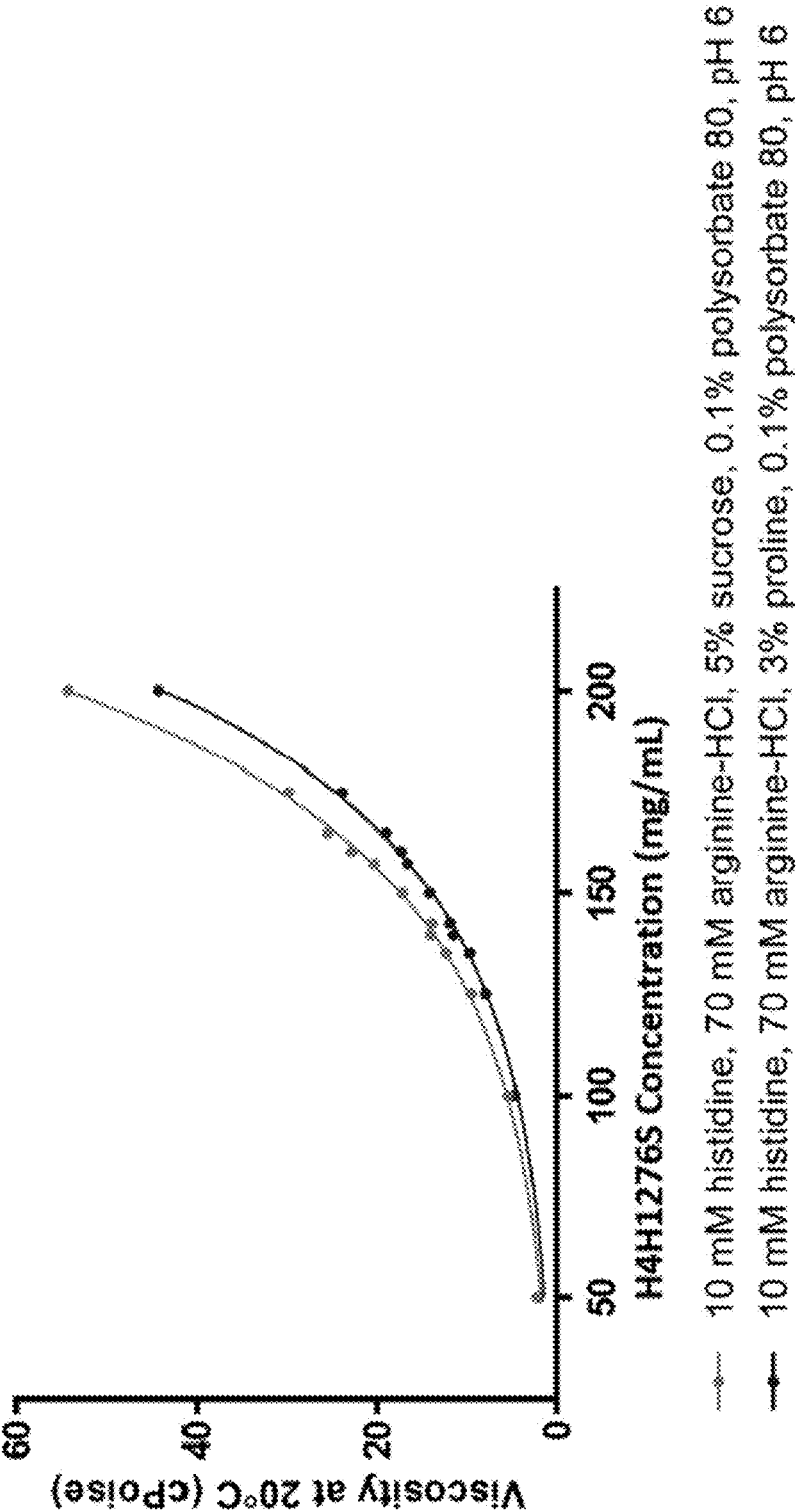
FIG. 11 graphically depicts the viscosity vs. H4H1276S concentration for the lead formulations.

To guide selection of the final formulation and better characterize the impact of thermal stabilizers on viscosity, formulations were prepared with different H4H1276S concentrations in the two lead formulations (10 mM histidine, pH 6.0, 70 mM arginine-HCl, 0.1% (w/v) polysorbate 80, and 5% (w/v) sucrose; and 10 mM histidine, pH 6, 70 mM arginine-HCl, 0.1% (w/v) polysorbate 80, and 3% (w/v) proline). The viscosity was measured at temperatures ranging from 5° C. to 35° C. FIG. 11 illustrates the viscosity versus H4H1276S concentration relationship for both formulations at 20° C. The proline-containing formulation (bottom curve of FIG. 11) had consistently lower viscosities at multiple H4H1276S concentrations when compared to the sucrose-containing formulation (top curve of FIG. 11).

Figures 12A, 12B:
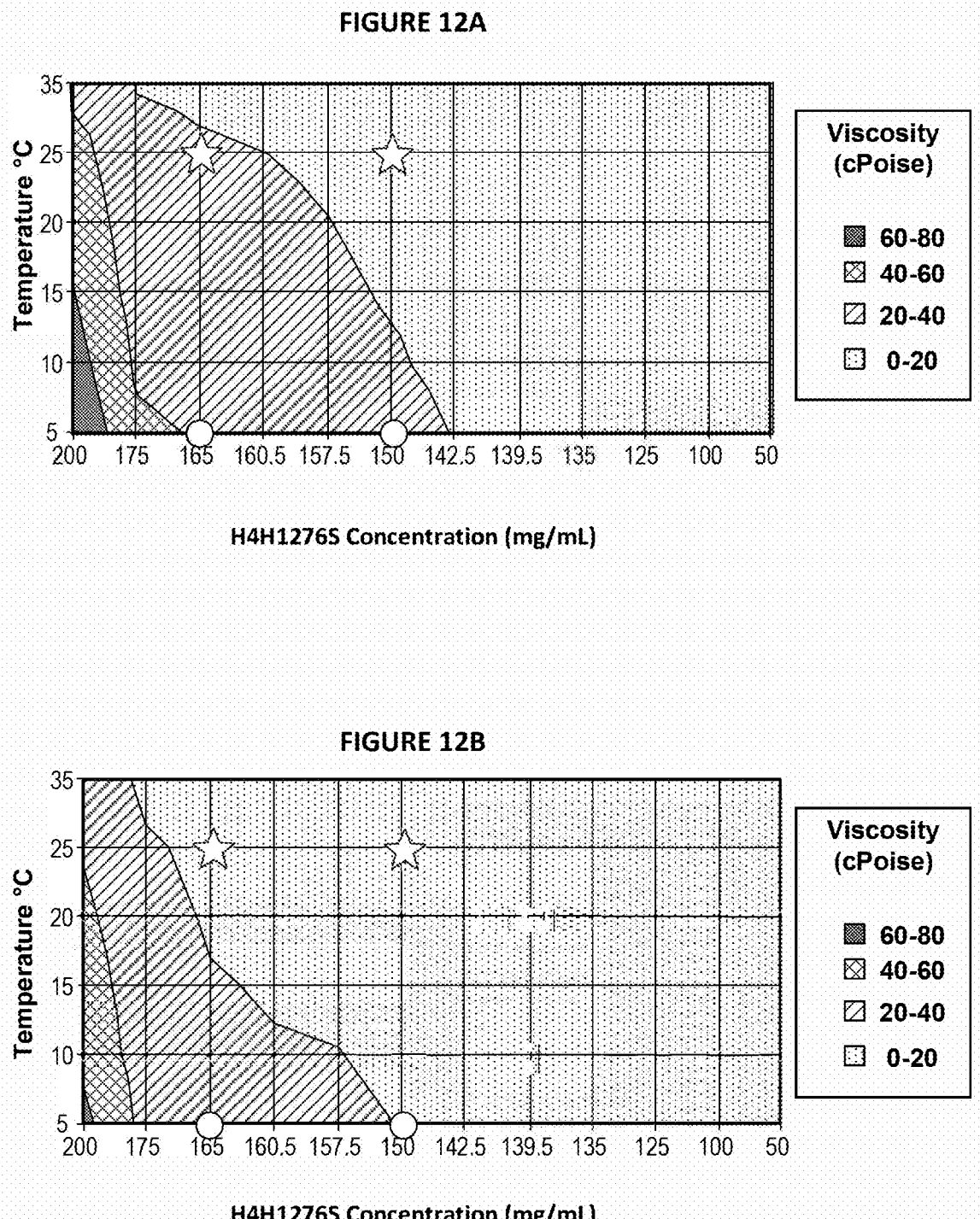
FIGS. 12A and 12B graphically depict the relationship between H4H1276S concentration, temperature, and viscosity. The star and circle points at 150 mg/mL H4H1276S also correspond to the recommended storage temperature of 5° C. (circle) or recommended administration temperature of 25° C. (star). The star and circle points at 165 mg/mL H4H1276S correspond to a formulation at a +10% manufacturing specification. The formulation of FIG. 12A is 10 mM histidine, 70 mM arginine-HCl, 5% sucrose, and 0.1% polysorbate 80, pH 6. The formulation of FIG. 12B is 10 mM histidine, 70 mM arginine-HCl, 3% proline, and 0.1% polysorbate 80, pH 6.

This trend was even more apparent at lower temperatures (FIGS. 12A and 12B). The data indicate that the formulation containing 3% (w/v) proline (FIG. 12B) offers a wider operational space of viscosity values that are considered to be acceptable. Because the stabilities of the two lead formulations are equivalent, and the proline-containing formulation has an advantageous viscosity profile, the formulation containing 3% (w/v) proline was selected for the final drug product formulation.

The final H4H1276S liquid drug product formulation contains 150 mg/mL H4H1276S, 10 mM histidine, 70 mM arginine-HCl, 3% (w/v) proline, and 0.1% (w/v) polysorbate 80 at pH 6.0. The main degradation pathways identified during development were high molecular weight species and charge variants. The final osmolality of the formulation is approximately 480 mOsm/kg, and the viscosity is approximately 15 cPoise (20° C.), which is suitable for clinical use.

A summary of the H4H1276S formulations developed for preclinical (GLP Toxicology) and clinical use are outlined in Table 12, below.

TABLE 12

Composition of H4H1276S Formulations used in GLP toxicology studies and
H4H1276S clinical DP Formulations

| Formulation Component | Frozen Liquid (GLP Toxicology Use) | Lyophilized DP (Clinical Use) | | Liquid DP (Clinical Use) for IV or SC |
| --- | --- | --- | --- | --- |
| | | Reconstituted for IV Administration | Reconstituted for SC Administration | |
| H4H1276S | 50 mg/mL | 50 mg/mL | 100 mg/mL | 150 mg/mL |
| Histidine | 10 mM | 10 mM | 20 mM | 10 mM |
| Arginine-HCl | Not applicable | Not applicable | Not applicable | 70 mM |
| Sucrose | 5% (w/v) | 5% (w/v) | 10% (w/v) | Not applicable |
| Proline | Not applicable | Not applicable | Not applicable | 3% (w/v) |
| Polysorbate 80 | 0.1% (w/v) | 0.1% (w/v) | 0.2% (w/v) | 0.1% (w/v) |
| pH | 6 | 6 | 6 | 6 |

Example 9

Summary of Stability Studies for H4H1276S Drug Product

Studies were carried out to evaluate the storage and accelerated stability of H4H1276S 150 mg/mL drug product (DP) (data not shown). Stability was assessed in terms of color and appearance, turbidity (increase in OD at 405 nm), pH, particulate matter by MFI, % total protein recovered by RP-UPLC (reversed phase ultra performance liquid chromatography), % purity by non-reduced and reduced MCE-SDS (microchip capillary electrophoresis-sodium dodecyl sulfate), % purity by SE-UPLC (size exclusion ultra performance liquid chromatography), charge variant analysis by CEX-UPLC (cation exchange ultra performance liquid chromatography), charge variant analysis by iCIEF (imaged capillary isoelectric focusing), and % relative potency by bioassay.

The DP used for the storage and accelerated stability study was manufactured by incubating 5.0 mL of formulated drug substance (FDS) into a 20 mL Type 1 clear glass vial. H4H1276S DP was physically and chemically stable when stored at 5° C. for at least 12 months. No appreciable change in the physical or chemical stability was detected in any of the monitored attributes.

Incubation followed at either 25° C./60% Relative Humidity (accelerated stability) or 45° C. (stress stability). These accelerated and stress conditions were selected to elucidate the degradation pathways for H4H1276S. As to the accelerated stability studies, after 3 months at 25° C./60% RH, appreciable formation of HMW species and charge variants were detected. No appreciable formation of HMW species or charge variant formation was observed after incubation for 1 month at 25° C./60% RH, indicating that H4H1276S DP can be exposed to room temperature for short periods of time. H4H1276S maintained potency, as determined by bioassay analysis, after incubation under the accelerated condition.

Incubation at 45° C. resulted in significant formation of HMW species and charge variants, in as little as 7 days, demonstrating that the increase in HMW species and the formation of charge variants are the main degradation pathways for H4H1276S DP. H4H1276S DP was found to be physically and chemically stable when agitated (vortexed at ambient temperature) for 120 minutes or when subjected to 8 freeze/thaw cycles (freezing at −30° C. and thawing at room temperature). No appreciable change in the physical or chemical stability was detected in any of the monitored attributes.

The results from the DP storage accelerated and stress stability studies indicate that H4H1276S 150 mg/mL DP will be stable during manufacture and storage. Furthermore, H4H1276S formulation can withstand short exposures to room temperature without compromising physical or chemical stability. H4H1276S 150 mg/mL DP will preferably be stored at 2° C. to 8° C., with exposure to temperatures greater than 2° C. to 8° C. limited.

Example 10

Development of an Amino Acid Based High Concentration Liquid Drug Product for H4H1276S, from Excipient Screening to Characterization of Rheological Properties H4H1276S was lyophilized and then reconstituted to higher protein concentrations with solutions containing the desired excipients. The pre-lyophilized formulation contained 4 mL of 87.5 mg/mL H4H1276S, with 10 mM Histidine, pH 6 and 2.5% (w/v) Sucrose. The lyophilized cake contained 350 mg of solid H4H1276S. The lyophilized cake was reconstituted with 2-2.4 mL solution to yield a final H4H1276S concentration of 160-175 mg/mL (nominal). The reconstitution solution was adjusted such that the final sample contained 20 mM Histidine, pH 6, with 5% (w/v) sucrose and the test excipient. To adjust the pH from 6 to 5, acetate buffer was added to the reconstitution solution, such that the final acetate concentration was 40 mM.

To investigate the accelerated and frozen storage stability of H4H1276S formulations containing viscosity-reducing excipients, the viscosity of the test formulations was measured at 20° C. using the Rheosense Viscometer. The test formulations were incubated in 2 mL glass vials at the following conditions: (i) 45° C. for 0, 7, 14 and 21 days; (ii) −20° C. for 0, 1, 2, 3, 6, and 9 months; and (iii) 5° C., −30° C. and −80° C. for 0 and 3 months. The resulting material was assayed for aggregate content by SEC and for charge variant formation by CEX.

To understand the relationship between protein concentration, temperature, and viscosity for H4H1276S formulations with reduced viscosity, 200 mg/mL H4H1276S formulations containing the following combinations of excipients were prepared. All formulations contained 10 mM histidine at pH 6 with 0.1% (w/v) polysorbate 80:

5% (w/v) Sucrose

5% (w/v) Sucrose, 70 mM L-Arg-HCl

3% (w/v) Sucrose, 1.3% (w/v) Proline, 70 mM L-Arg-HCl

3% (w/v) Proline

3% (w/v) Proline, 70 mM L-Arg-HCl.

The 200 mg/mL formulation was diluted with the respective formulation buffer to protein concentrations ranging from 50-200 mg/mL. Viscosity measurements of each formulation were performed on the Rheosense Viscometer at temperatures ranging from 5-35° C. Finally, data analysis was performed in GraphPad Prism and MiniTab.

Figure 13A:
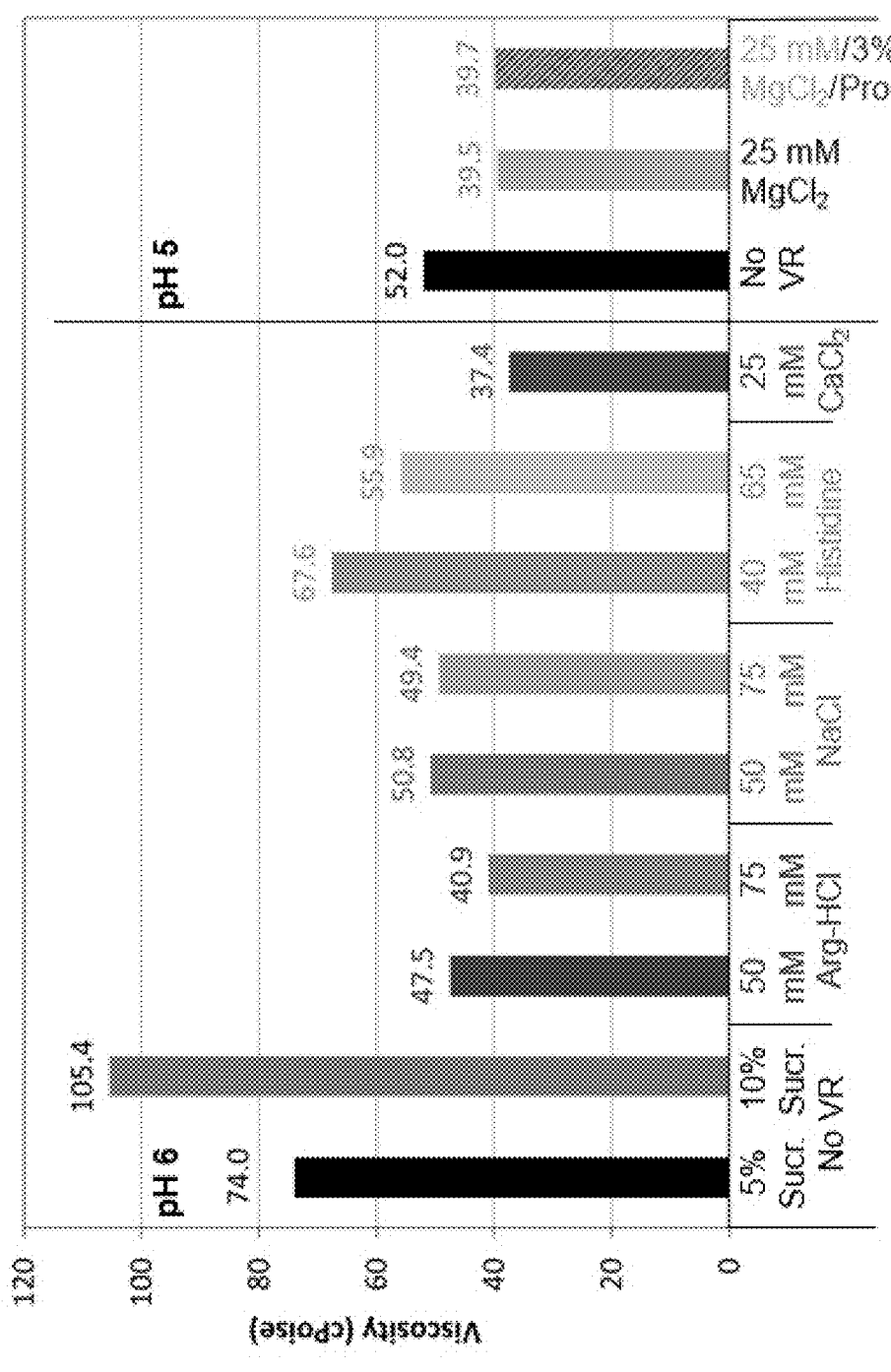
FIGS. 13A and 13B are bar graphs showing the results of screening for viscosity-reducing excipients.
Figure 13B:
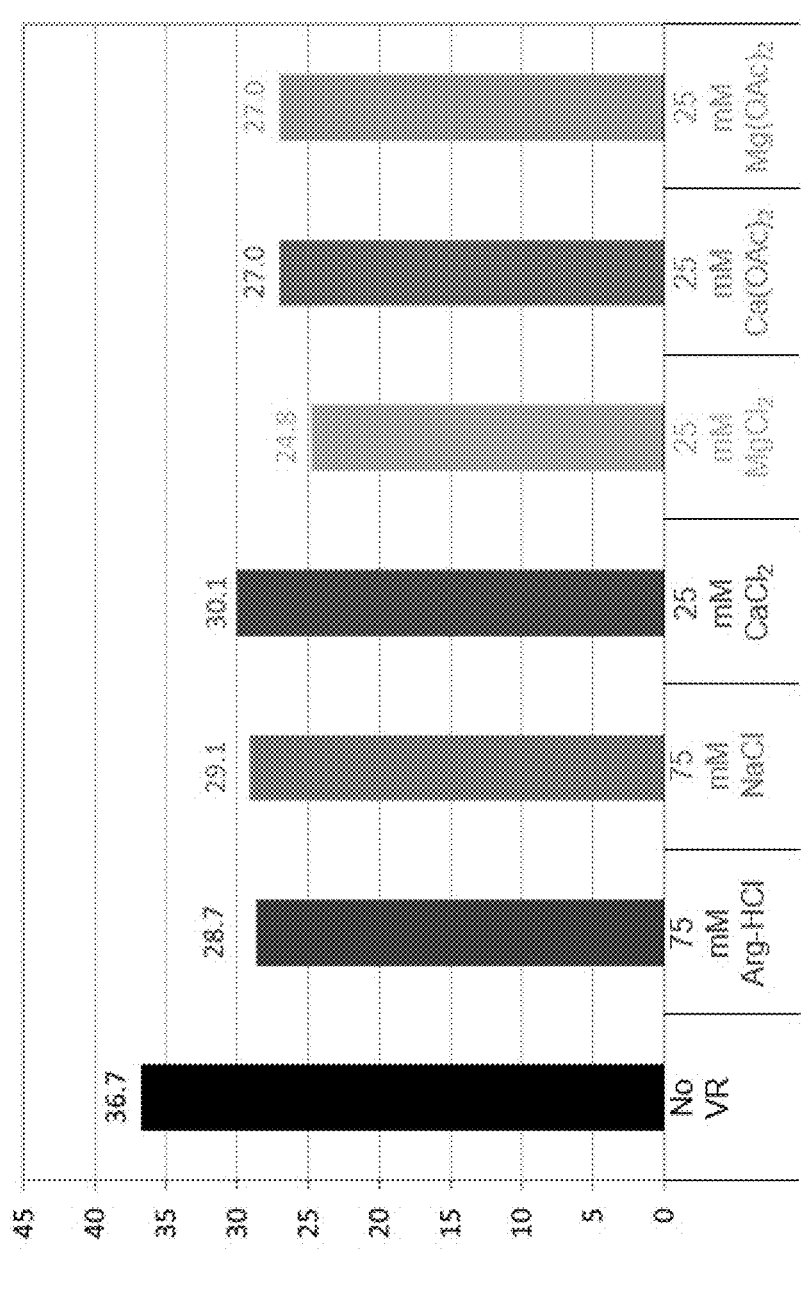

The results of the screening for viscosity-reducing excipients are shown in FIGS. 13A and 13B. For FIG. 13A, upon reconstitution, the base formulation contained 175 mg/mL H4H1276S, 20 mM Histidine, pH 6, 0.1% (w/v) polysorbate 80, 5% (w/v) sucrose. To achieve a pH 5 solution, acetate was added at a final concentration of 40 mM. An equivalent formulation containing 40 mM acetate, pH 6.0, had a viscosity of 64.1 cPoise, indicating that both addition of acetate and pH adjustment to 5.0 reduce the viscosity of H4H1276S formulations. For FIG. 13B, upon reconstitution, the base formulation contained 165 mg/mL H4H1276S, 20 mM Histidine/40 mM Acetate, pH 5.0, 0.1% (w/v) polysorbate 80 and 5% (w/v) sucrose.

The addition of monovalent and divalent salts (L-Arg-HCl, NaCl, $CaCl_2$, $MgCl_2$, $Ca(OAc)_2$, $Mg(OAc)_2$) reduced the viscosity of H4H1276S formulations. The viscosity of H4H1276S formulations was also reduced by adjusting the pH from 6 to 5. Finally, sucrose increased the viscosity, while L-proline did not affect the viscosity, of H4H1276S formulations.

Figure 14:
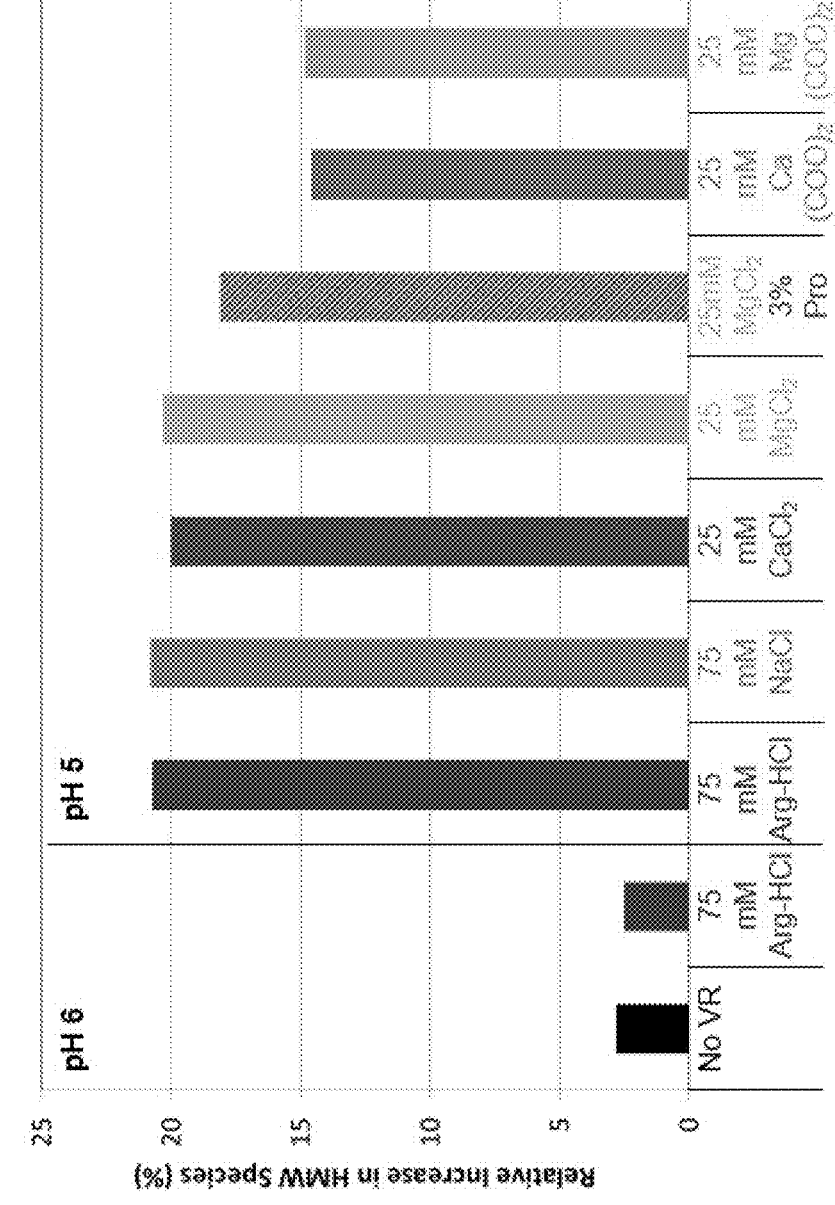
FIG. 14 shows a bar graph, in which the relative increase in HMW species (quantified as a percent) is provided for various excipients, following 21 days incubation at 45° C.

The formation of high molecular weight (HMW) species following 21 days incubation at 45° C. is shown in FIG. 14. Select H4H1276S formulations containing various VR (viscosity-reducing) excipients were incubated at 45° C. and analyzed by SEC for aggregate content. The relative increase in HMW species from the t=0 sample is plotted as a function of formulation. Under accelerated conditions (45° C. for 21 days), the following was observed:

L-Arg-HCl had little impact on the formation of HMW species;

Reducing the pH of H4H1276S formulations led to increased formation of HMW species;

The relative increase in HMW species was similar for the CaCl2- and MgCl2-containing formulations compared to the L-Arg-HCl- and NaCl-containing formulations;

L-proline acted as a thermal stabilizer and reduced the formation of HMW species; and Compared to the L-Arg-HCl formulation, Ca(OAc)2- and Mg(OAc)2-containing formulations had reduced HMW species formation.

Thus, L-Arg-HCl or $Mg(OAc)_2$ (substantial viscosity reduction) in pH 6 buffer (better accelerated stability) were chosen as the lead viscosity reducers for further development.

Figure 15A:
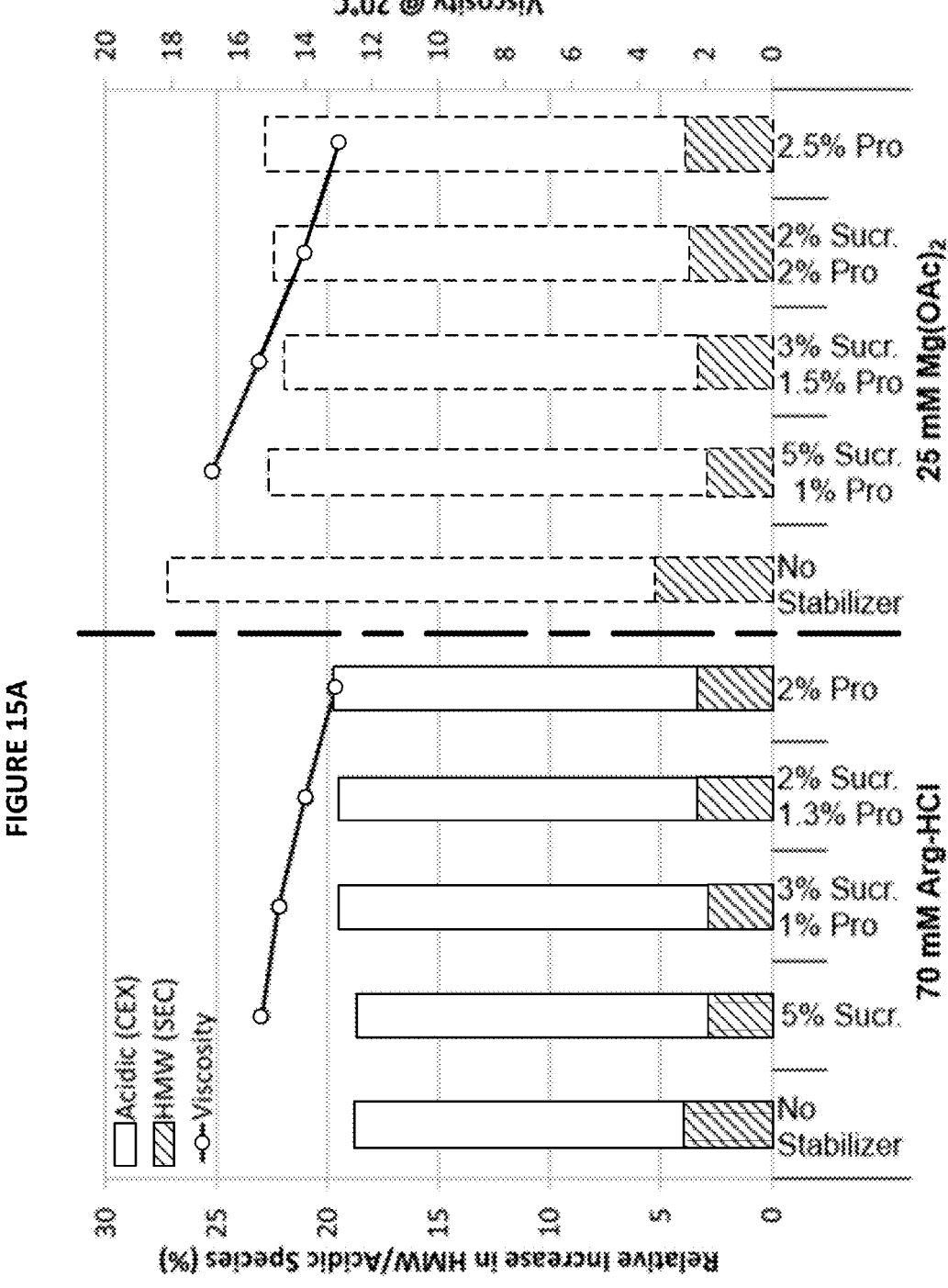
FIGS. 15A and 15B depict the stability of H4H1276S formulations containing viscosity-reducing excipients in bar graph (FIG. 15A) and line graph (FIG. 15B) forms.
Figure 15B:
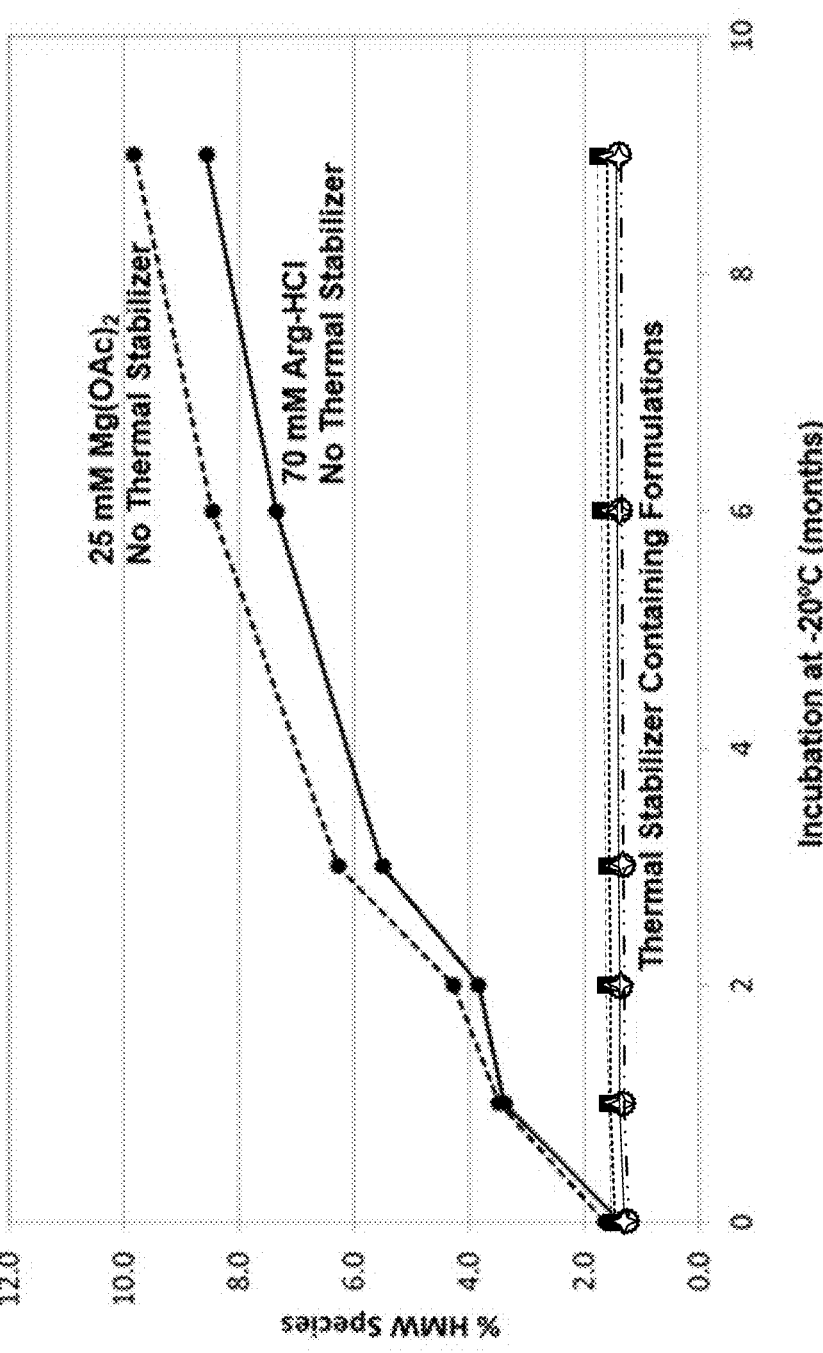

The stability of H4H1276S formulations containing viscosity-reducing excipients is summarized in FIGS. 15A and 15B. 150 mg/mL H4H1276S formulations containing either 70 mM L-Arg-HCl or 25 mM $Mg(OAc)_2$ were formulated with various concentrations of sucrose and/or L-proline. The concentrations were adjusted to target an osmolality of approximately 300 mM to maintain isotonicity. Formulations containing only L-Arg-HCl or $Mg(OAc)_2$ were prepared at 175 mg/mL H4H1276S. For FIG. 15A, depicting the degradation of H4H1276S following 21 days incubation at 45° C., samples were incubated at 45° C. and analyzed by SEC for aggregate content and CEX for acidic charge variant formation. The relative increase in HMW or acidic species from the t=0 sample is plotted as a function of formulation. For FIG. 15B, depicting the frozen storage stability of H4H1276S, samples were incubated at −20° C. for 9 months and analyzed by SEC for aggregate content. The percentage of HMW species is plotted as a function of time. Test formulations were also incubated at −80° C., −30° C. and 5° C. for 3 months (data not shown). No change in HMW species was observed at −80° C. for any of the formulations. At 5° C. or −30° C., the formulations without thermal stabilizer had increased HMW species content.

$Mg(OAc)_2$ formulations were slightly less stable at accelerated storage conditions than those containing L-Arg-HCl, with increased formation of both HMW species and acidic species. Replacement of sucrose with L-proline decreased the viscosity in a concentration-dependent manner. The addition of sucrose, L-proline, or a combination of both excipients sufficiently protected H4H1276S from HMW species formation at −20° C. Thus, 70 mM L-Arg-HCL was selected as the lead viscosity reducer for further development. The data presented support the use of $Mg(OAc)_2$ as a back-up excipient.

Figure 16B:
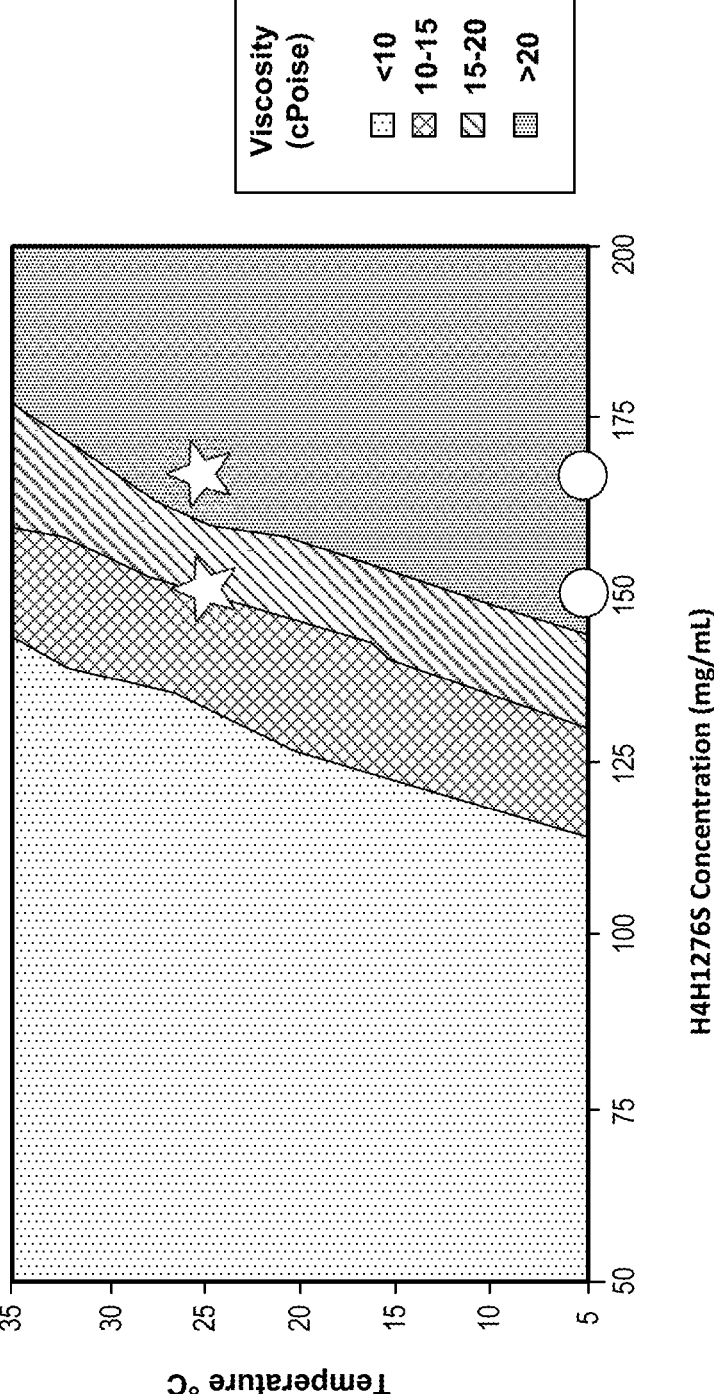

The relationship between the protein concentration, temperature, and viscosity is shown in FIGS. 16A and 16B. These figures show contour plots of viscosity versus protein concentration and temperature. The contour plots were generated in Minitab. The shapes at points corresponding to 150 mg/mL and 165 mg/mL (or 150 mg/mL+10%) H4H1276S are at the recommended storage temperature of 5° C. (circle) or recommended administration temperature of 25° C. (star).

Figure 17:
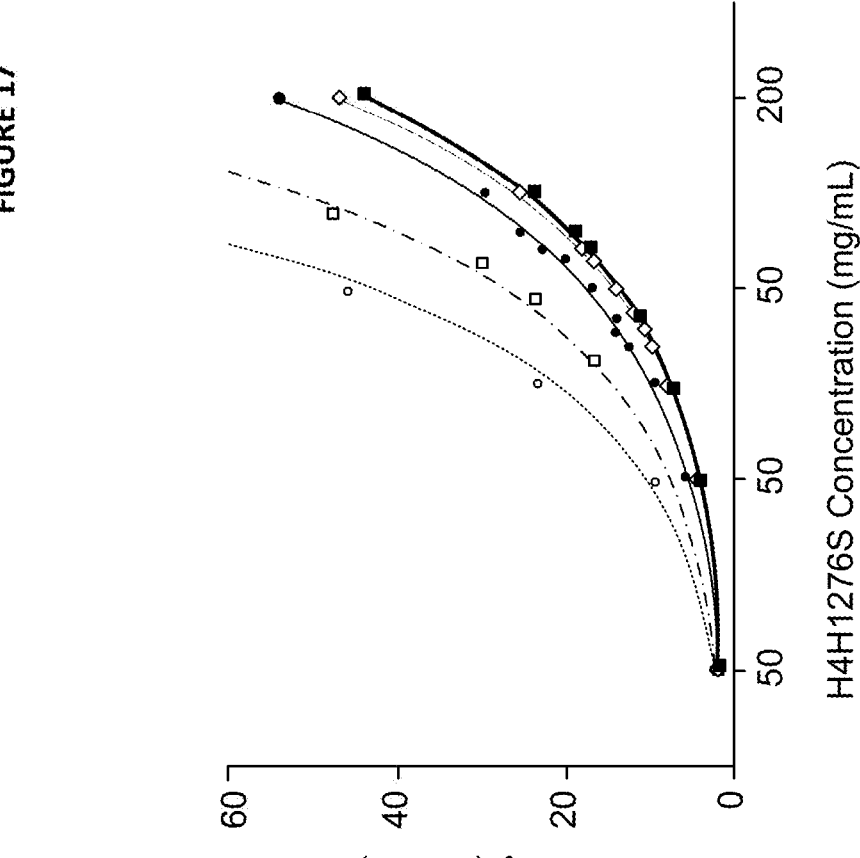
FIG. 17 graphically depicts viscosity vs. H4H1276S concentration at 20° C. Viscosity was plotted as a function of protein concentration. The data was fit to an exponential curve using GraphPad Prism. The equation(s) can be used to predict viscosity based on known concentration, which is useful for defining manufacturing specifications

The relationship between viscosity and protein concentration at 20° C. is shown in FIG. 17. Viscosity was plotted as a function of protein concentration, with the data fit to an exponential curve using GraphPad Prism. The equation(s) can be used to predict viscosity based on known concentration, which is useful for defining manufacturing specifications in the final product and informing process development. The equation for the formulation containing 3% L-proline and 70 mM L-Arg-HCl is: viscosity=0.444 $e^{0.023}$ [H4H1276S].

The above-mentioned contour plots and graph support the following observations: Compared with the sucrose-containing formulations, the L-proline-containing formulations had consistently lower viscosities at multiple H4H1276S concentrations (and temperatures; data not shown) with or without 70 mM L-Arg-HCl.

The viscosity versus protein concentration curve (at 20° C.) for the formulation containing a combination of 5% sucrose and 3% L-proline was very similar to the 3% proline formulation. Differentiation between these two formulations was, in fact, more apparent at lower temperatures and higher protein concentrations. The contour plots for these formulations had subtle, but distinct differences (data not shown)

When considering both temperature and manufacturing specifications, the L-proline formulation offered a wider operation space of viscosity values that are considered acceptable for SC administration (FIG. 16A).

The amino acid-based formulation containing 150 mg/mL H4H1276S, 10 mM Histidine, pH 6 with 70 mM L-Arg-HCl, and 3% proline was selected for H4H1276S DP development.

The formulation containing a combination of both sucrose and L-proline was eliminated for further development, because it offered no advantage in terms of frozen storage stability (see above).

Thus, a thorough understanding of the relationship between the viscosity, protein concentration, and temperature have been found herein to inform decision-making and facilitate selection of a formulation that is stable upon storage and deliverable in a pre-filled syringe or auto injector format. The viscosity should ideally be considered at a range of protein concentrations, and a target concentration selected located on the lower end of the viscosity versus protein concentration curve, in order to account for manufacturing specifications of the DP and process related manufacturing steps (i.e., bulk drug substance).

Example 11

Compatibility with Intravenous Delivery Device

For delivery in a clinical setting, 150 mg/mL H4H1276S DP can be diluted in an intravenous (IV) bag containing normal saline for IV administration, at clinical doses of 5 mg/kg and 15 mg/kg. The in-use stability of H4H1276S to support IV administration of the clinical doses was assessed. Two admixture concentrations, 0.5 mg/mL H4H1276S and 20 mg/mL H4H1276S, were examined in an effort to bracket the low and high concentrations of admixtures that could be administered in a clinical setting.

In order to evaluate delivery of the admixture from IV bags using an IV pump and infusion set containing an inline filter, normal saline-containing IV bags made of polyvinyl chloride (PVC) with Di-(2-ethylhexyl)phthalate (DEHP) and two types of commonly used infusion pumps (peristaltic and fluid displacement) were tested. Several infusion sets containing the basic materials (PVC with DEHP, PVC with TOTM and polyethylene) and a 0.2 µm polyethersulfone inline filter were also evaluated.

Assays

The compatibility of the H4H1276S admixture with materials used in IV dosing device was assessed using the following assays:

Color and appearance by visual inspection pH

Turbidity measured by increase in Optical Density (OD) at 405 nm

Subvisible particulate analysis on admixture by light obscuration (HIAC)

Protein concentration by reversed-phase high performance liquid chromatography (RP-UPLC)

Purity by SE-U PLC

Potency, by bioassay: the relative potency of each sample is determined using the bioassay and is defined as: (IC50 Reference Sample/IC50 Sample)×100%. The measured potency of storage stability samples must be within 50-150% of the measured potency of the reference standard.

Study Procedure 100 mL normal saline IV bags containing H4H1276S DP were subjected to various stress conditions to assess whether H4H1276S is stable in the admixture and when delivered intravenously. The IV bags containing the admixture were initially held for 24 hours at 5° C.; the bags were then incubated for at least 8 hours at 25° C. After these incubations were complete, each of the evaluated infusion sets was connected to an IV bag, primed with the admixture, and held for 1 hour at ambient room temperature. Each admixture was then pumped through the respective infusion set at rates of either 25 mL/hr or 500 mL/hr. In the clinic, the doses could be administrated using DP diluted in either 100 mL or 250 mL IV bags. For the compatibility study, 100 mL IV bags were used to test each dose.

Study Results 0.5 mg/mL and 20 mg/mL H4H1276S, diluted in saline, were physically and chemically stable under all conditions tested, including the following conditions: i) 5° C. for 24 hours in an IV bag, ii) 25° C. for 8 hours in an IV bag, and iii) ambient temperature for one hour in all infusion sets tested.

In addition, H4H1276S admixtures were stable when pumped through each of the evaluated infusion sets utilizing the various infusion pumps at rates of 25 mL/hr and 500 mL/hr. Precipitate was not detected by visual inspection or turbidity measurement. The pH of the solutions were stable, and no appreciable decreases in protein concentration were observed. No appreciable changes in the relative percentage of high or low molecular weight species were observed in this compatibility study, as determined by size exclusion ultra-performance liquid chromatography (SE-UPLC). No meaningful changes in levels of subvisible particulates, compared to t=0, were observed after samples were pumped through the infusion sets at 500 mL/hr, as determined by HIAC analysis. Finally, all samples tested maintained potency, as determined by Bioassay.

The data support the following dose preparation and administration in the clinic:

Normal saline IV bags made of PVC with DEHP are compatible with H4H1276S for IV administration.

H4H1276S can be diluted to concentrations as low as 0.5 mg/mL in PVC IV bags containing normal saline for IV administration;

H4H1276S can be diluted as high as 20.0 mg/mL in PVC IV bags containing normal saline for IV administration;

H4H1276S admixture in normal saline was stable after incubation in a PVC IV bag for up to 24 hours at 5° C. and 8 hours at 25° C. The diluted H4H1276S admixture will be administered within four hours of preparation;

The H4H1276S admixture in normal saline can be administered using a standard infusion pump;

The H4H1276S admixture can be administered with an infusion set composed of either PVC containing DEHP, PVC containing TOTM, or polyethylene;

The H4H1276S admixture is compatible with the use of an inline 0.2 µm polyethersulfone filter;

The H4H1276S admixture can be administered at a flow rate ranging from 25 to 500 mL/hr.

Example 12

Further Stability Studies for H4H1276S Drug Product

The H4H1276S formulation was subjected to extended storage at −20° C. and 5° C. over periods up to 36 months and analyzed for stability.

First, the formulation was 150 mg/mL H4H1276S, 10 mM histidine, pH 6.0, 70 mM arginine-HCl, 3% (w/v) proline, and 0.1% (w/v) polysorbate 80. 2.0 mL fill volume in a 5 mL Nalge-Nunc gamma-irradiated polycarbonate vial with silicone-lined closure.

TABLE 13

| Research Stability of H4H1276S Formulated Drug Substance Stored at −20° C. | | | | | | | | | |
|---|---|---|---|---|---|---|---|---|---|
| | Length of Storage at −20° C. (months) | | | | | | | | |
| Assay | 0 | 1 | 3 | 6 | 9 | 12 | 18 | 24 | 36 |
| Color and Appearance | Pass | Pass | Pass | Pass | Pass | Pass | Pass | Pass | Pass |
| Turbidity (Increase in OD at 405 nm) | 0.00 | 0.00 | 0.00 | 0.00 | 0.00 | 0.00 | 0.00 | 0.01 | 0.00 |
| pH | 6.0 | 6.0 | 6.0 | 6.0 | 6.1 | 6.0 | 6.0 | 6.1 | 6.0 |
| % Total Protein Recovered by RP-UPLC | 100 | 103 | 102 | 103 | 102 | 105 | 102 | 106 | 107 |
| Purity by MCE-SDS — Non-reduced; % main peak | 95.1 | NR | NR | 94.5 | NR | 94.9 | NR | NR | 96.5 |
| Purity by MCE-SDS — Reduced; % heavy + light chain | 97.8 | NR | NR | 91.8 | NR | 99.4 | NR | NR | 99.1 |
| Purity by SE-UPLC — % HMW | 1.2 | 1.2 | 1.3 | 1.3 | 1.3 | 1.3 | 1.3 | 1.3 | 1.4 |
| Purity by SE-UPLC — % Monomer | 98.8 | 98.8 | 98.7 | 98.7 | 98.6 | 98.7 | 98.6 | 98.6 | 98.6 |
| Purity by SE-UPLC — % LMW | 0.0 | 0.0 | 0.0 | 0.0 | 0.0 | 0.0 | 0.0 | 0.0 | 0.1 |
| Charge Variant Analysis by CEX-UPLC — % Acidic | 28.5 | 29.1 | 28.8 | 29.8 | 30.1 | 29.9 | 29.1 | 29.5 | 29.1 |
| Charge Variant Analysis by CEX-UPLC — % Main | 47.3 | 46.8 | 48.1 | 46.5 | 48.4 | 49.8 | 48.9 | 46.8 | 46.5 |
| Charge Variant Analysis by CEX-UPLC — % Basic | 24.2 | 24.2 | 23.1 | 23.7 | 21.6 | 20.3 | 22.1 | 23.7 | 24.5 |
| Charge Variant Analysis by iCIEF — % Acidic | 37.9 | NR | NR | 38.3 | NR | 38.4 | NR | 37.0 | 36.1 |
| Charge Variant Analysis by iCIEF — % Main | 50.2 | NR | NR | 49.8 | NR | 49.1 | NR | 50.0 | 52.0 |
| Charge Variant Analysis by iCIEF — % Basic | 11.9 | NR | NR | 11.9 | NR | 12.5 | NR | 13.0 | 11.9 |

Next, the formulation was 150 mg/mL H4H1276S drug product, 10 mM L-histidine, pH 6.0, 70 mM arginine-HCl, 3% (w/v) L-proline, and 0.1% (w/v) polysorbate 80. 5.0 mL fill volume in a 20 mL Type 1 clear glass vials with a 20 mm FluroTec® coated West S2-451 4432/50 GRY B2-40 stoppers.

TABLE 14

| Research Stability of H4H1276S Drug Product stored at 5° C. | | | | | | | | | |
|---|---|---|---|---|---|---|---|---|---|
| | | Length of Storage at 5° C. (months) | | | | | | | |
| Assay | | 0 | 1 | 3 | 6 | 9 | 12 | 18 | 24 |
| Color and Appearance | | Pass | Pass | Pass | Pass | Pass | Pass | Pass | Pass |
| Turbidity (Increase in OD at 405 nm) | | 0.00 | 0.01 | 0.00 | 0.00 | 0.00 | 0.00 | 0.00 | 0.00 |
| pH | | 6.0 | 6.0 | 6.1 | 6.1 | 6.1 | 6.0 | 6.0 | 6.0 |
| Particulate Analysis by MFI (particles/mL) | 2-10 μm | 131 | NR | NR | 1406 | NR | 1104 | NR | 888 |
| | ≥10 μm | 0 | NR | NR | 19 | NR | 15 | NR | 6 |
| | ≥25 μm | 0 | NR | NR | 0 | NR | 2 | NR | 0 |
| Total Protein Content by RP-UPLC (mg/mL) | | 158.2 | 159.1 | 157.5 | 158.3 | 152.3 | 161.9 | 152.2 | 159.1 |
| Purity by MCE-SDS | Non-reduced; % main peak | 92.2 | NR | NR | 95.2 | NR | 94.9 | NR | 95.0 |
| | Reduced; % heavy + light chain | 98.2 | NR | NR | 99.6 | NR | 97.6 | NR | 98.3 |
| Purity by SE-UPLC | % HMW | 1.4 | 1.3 | 1.4 | 1.5 | 1.5 | 1.6 | 1.6 | 1.7 |
| | % Main | 98.6 | 98.6 | 98.6 | 98.5 | 98.4 | 98.4 | 98.3 | 98.2 |
| | % LMW | 0.0 | 0.0 | 0.1 | 0.1 | 0.1 | 0.1 | 0.1 | 0.1 |
| Charge Variant Analysis by CEX-UPLC | % Region 1 | 29.1 | 28.2 | 29.2 | 29.8 | 30.5 | 30.5 | 30.3 | 29.6 |
| | % Region 2 | 47.1 | 46.6 | 46.7 | 48.0 | 50.5 | 48.5 | 46.4 | 45.8 |
| | % Region 3 | 23.8 | 25.2 | 24.0 | 22.3 | 19.0 | 21.0 | 23.3 | 24.6 |
| Charge Variant Analysis by iCIEF | % Region 1 | 36.4 | NR | NR | 38.5 | NR | 38.8 | NR | 37.0 |
| | % Region 2 | 50.4 | NR | NR | 49.0 | NR | 47.8 | NR | 50.5 |
| | % Region 3 | 13.2 | NR | NR | 12.5 | NR | 13.4 | NR | 12.5 |
| % Relative Potency (Bioassay) | | 90 | NR | NR | 97 | NR | 109 | NR | 106 |

Formulated drug substance was stored for extended periods of time (up to 36 months) at −20° C., and drug product was stored for extended periods of time (up to 24 months) at 5° C. As seen in Tables 13 and 14, formulated H4H1276S showed stability, e.g., values remained within acceptable ranges in all tests, over the entire range of storage lengths.

Example 13

Containers

The primary container for antibody drug product intended for clinical development and product commercialization is a pre-filled syringe, which is presented as either a stand-alone syringe for self-injection or incorporated into an auto injector device for self-administration. The antibody formulations can also be developed in glass vials (for delivery by intravenous infusion).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

What is claimed is:

1. A liquid pharmaceutical formulation comprising: (a) an antibody or antigen-binding fragment thereof that binds specifically to human angiopoietin-like protein 3 (ANGPTL3), wherein the antibody or antigen-binding fragment thereof comprises three heavy chain complementarity determining regions (HCDR1, HCDR2, HCDR3) contained within a heavy chain variable region (HCVR) having an amino acid sequence of SEQ ID NO:66, and three light chain complementarity determining region (LCDR1, LCDR2, LCDR3) contained within a light chain variable region (LCVR) having an amino acid sequence of SEQ ID NO:74, wherein the antibody concentration is from 50 mg/mL±0.75 mg/mL to 250 mg/mL±37.5 mg/mL; (b) a buffer, wherein the buffer is histidine, wherein the histidine concentration is from 5 mM±1 mM to 20 mM±4 mM; (c) an organic cosolvent, wherein the organic cosolvent is selected from the group consisting of polysorbate, poloxamer 188 and polyethylene glycol 3350, wherein the organic cosolvent concentration is from about 0.01% w/v±0.005% to about 1% w/v±0.5%; and (d) at least one viscosity modifier, wherein the at least one viscosity modifier is selected from the group consisting of arginine-HCl, sodium chloride, histidine-HCl, sodium acetate, calcium chloride, magnesium chloride, calcium acetate, and magnesium acetate, wherein the viscosity modifier concentration is from 25 mM to about 75 mM, wherein the formulation has a pH of 6.0±0.3, wherein the liquid pharmaceutical formulation further comprises at least one amino acid, wherein the amino acid is proline, wherein the proline concentration is from >0 to 5% w/v±1%.

2. The liquid pharmaceutical formulation of claim 1, wherein the antibody or antigen-binding fragment thereof comprises a heavy chain variable region (HCVR) having an amino acid sequence of SEQ ID NO: 66 and a light chain variable region (LCVR) having an amino acid sequence of SEQ ID NO: 74.

3. The liquid pharmaceutical formulation of claim 1, wherein the antibody or antigen-binding fragment thereof comprises a heavy chain complementarity determining region (HCDR1) having an amino acid sequence of SEQ ID NO: 68, a HCDR2 having an amino acid sequence of SEQ ID NO: 70, a HCDR3 having an amino acid sequence of SEQ ID NO: 72, a light chain complementarity determining region (LCDR1) having an amino acid sequence of SEQ ID NO: 76, a LCDR2 having an amino acid sequence of SEQ ID NO: 78, and a LCDR3 having an amino acid sequence of SEQ ID NO: 80.

4. The liquid pharmaceutical formulation of claim 1, wherein the antibody concentration is 150 mg/mL±22.5 mg/mL.

5. The liquid pharmaceutical formulation of claim 1, wherein the antibody concentration is 175 mg/mL±26.25 mg/mL.

6. The liquid pharmaceutical formulation of claim 1, wherein the histidine concentration is about 10 mM±2 mM.

7. The liquid pharmaceutical formulation of claim 1, wherein the organic cosolvent is polysorbate.

8. The liquid pharmaceutical formulation of claim 7, wherein the polysorbate concentration is from 0.01% w/v±0.005% to 0.5% w/v±0.25%.

9. The liquid pharmaceutical formulation of claim 8, wherein the polysorbate concentration is 0.1% w/v±0.05%.

10. The liquid pharmaceutical formulation of claim 7, wherein the organic cosolvent is polysorbate 80.

11. The liquid pharmaceutical formulation of claim 1, wherein the at least one viscosity modifier is arginine HCl.

12. The liquid pharmaceutical formulation of claim 11, wherein the arginine HCl concentration is from about 50 mM to about 75 mM.

13. The liquid pharmaceutical formulation of claim 12, wherein the arginine HCl concentration is about 70 mM.

14. The liquid pharmaceutical formulation of claim 1, wherein the proline concentration is 3% w/v±0.6%.

15. A liquid pharmaceutical formulation comprising: i) 150 mg/mL±22.25 mg/mL anti-ANGPTL3 antibody or antigen-binding fragment thereof, wherein the antibody or antigen-binding fragment thereof comprises three heavy chain complementarity determining regions (HCDR1, HCDR2, HCDR3) contained within a heavy chain variable region (HCVR) having an amino acid sequence of SEQ ID NO:66, and three light chain complementarity determining region (LCDR1, LCDR2, LCDR3) contained within a light chain variable region (LCVR) having an amino acid sequence of SEQ ID NO:74; ii) from 5 mM±1 mM to 20 mM±4 mM histidine; iii) from 0.1% w/v±0.05% to 0.5% w/v±0.25% polysorbate 80; iv) from 50 mM to 75 mM arginine-HCL; and v) from 1% w/v±0.2% to 5% w/v±1% proline, wherein the liquid pharmaceutical formulation is at pH 6.0±0.3.

16. The liquid pharmaceutical formulation of claim 15, wherein the histidine concentration is 10 mM±2 mM, wherein polysorbate concentration is 0.1% w/v±0.05%, wherein the arginine-HCl concentration is about 70 mM, and wherein the proline concentration is 3% w/v±0.6%.

17. The liquid pharmaceutical formulation of claim 1, wherein the liquid pharmaceutical formulation has viscosity less than about 20 cP.

18. The liquid pharmaceutical formulation of claim 1, wherein at least about 95% of the antibody or antigen-binding fragment thereof has native conformation after 21 days at 45° C.

19. The liquid pharmaceutical formulation of claim 1, wherein at least about 45% of the antibody or antigen-binding fragment thereof is the main charge variant of the antibody after 21 days at 45° C.

20. The liquid pharmaceutical formulation of claim 1, wherein at least about 98% of the antibody or antigen-binding fragment thereof has native conformation after 36 months at 5° C.

21. The liquid pharmaceutical formulation of claim 1, wherein at least about 55% of the antibody or antigen-binding fragment thereof is the main charge variant of the antibody after 36 months at 5° C.

22. The liquid pharmaceutical formulation of claim 1, wherein at least about 98% of the antibody or antigen-binding fragment thereof has native conformation after 36 months at –30° C.

23. The liquid pharmaceutical formulation of claim 1, wherein at least about 57% of the antibody or antigen-binding fragment thereof is the main charge variant of the antibody after 36 months at –30° C.

24. The liquid pharmaceutical formulation of claim 15, wherein the antibody or antigen-binding fragment thereof comprises a heavy chain variable region (HCVR) having an amino acid sequence of SEQ ID NO: 66 and a light chain variable region (LCVR) having an amino acid sequence of SEQ ID NO: 74.

25. The liquid pharmaceutical formulation of claim 15, wherein the antibody or antigen-binding fragment thereof comprises a heavy chain complementarity determining region (HCDR1) having an amino acid sequence of 68, a HCDR2 having an amino acid sequence of 70, a HCDR3 having an amino acid sequence of 72, a light chain complementarity determining region (LCDR1) having an amino acid sequence of 76, a LCDR2 having an amino acid sequence of 78, and a LCDR3 having an amino acid sequence of SEQ ID NO: 80.

26. The liquid pharmaceutical formulation of claim 1, wherein the liquid pharmaceutical formulation is in a pre-filled syringe or autoinjector.

27. The liquid pharmaceutical formulation of claim 1, wherein the liquid pharmaceutical formulation is in a glass vial.

28. A kit comprising the liquid pharmaceutical formulation of claim 1, a container, and instructions.

29. The kit of claim 28, wherein the container is a prefilled syringe or autoinjector.

* * * * *

SEQUENCE LISTING

```
<160> NUMBER OF SEQ ID NOS: 196

<210> SEQ ID NO 1
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1
caggtgcagc tggtggagtc tggggggaggc gtggtccagc ctgggaggtc cctgagactc      60
tcctgtgcag cctctggatt caccttcagt agttatggca tgcactgggt ccgccaggct     120
ccaggcaagg ggctggagtg ggtggcagtt atatcatatg atggaagtaa taaatactat     180
gcagactccg tgaagggccg attcaccatt tccagagaca attccaagaa cacgctgtat     240
ctgcaaatga acagcctgag agctgaggac acggctgtgt attactgtgc gaaagtggga     300
gctactactt tctactacta ctacggtatg gacgtctggg gccaagggac cacggtcacc     360
gtctcctca                                                            369

<210> SEQ ID NO 2
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Val Gly Ala Thr Thr Phe Tyr Tyr Tyr Gly Met Asp Val
            100                 105                 110

Trp Gly Gln Gly Thr Thr Val Thr Val Ser Ser
        115                 120

<210> SEQ ID NO 3
```

-continued

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggattcacct tcagtagtta tggc                                          24

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Phe Thr Phe Ser Ser Tyr Gly
1               5

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
atatcatatg atggaagtaa taaa                                          24

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Ser Tyr Asp Gly Ser Asn Lys
1               5

<210> SEQ ID NO 7
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gcgaaagtgg gagctactac tttctactac tactacggta tggacgtc                48

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Lys Val Gly Ala Thr Thr Phe Tyr Tyr Tyr Tyr Gly Met Asp Val
1               5                   10                  15
```

```
<210> SEQ ID NO 9
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
gacatccaga tgacccagtc tccatcttcc gtgtctgcat ttgtaggaga cagagtcacc        60
atcacttgtc gggcgagtca gggtattagc agctggttag cctggtatca gcagaaacca       120
gggaaagccc ctaagctcct gatctatgct gcatccagtt tgcaaagtgg ggtcccatca       180
aggttcagcg gcagtggatc tgggacagat ttcactctca ccatcagcag cctgcagcct       240
gaagattttg caacttacta ttgtcaaaag gctaacagtt tcccattcac tttcggccct       300
gggaccaaag tggatatcaa a                                                 321

<210> SEQ ID NO 10
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Asp Ile Gln Met Thr Gln Ser Pro Ser Ser Val Ser Ala Phe Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Lys Ala Asn Ser Phe Pro Phe
                85                  90                  95

Thr Phe Gly Pro Gly Thr Lys Val Glu Ile Lys
            100                 105

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
cagggtatta gcagctgg                                                      18

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12
```

-continued

Gln Gly Ile Ser Ser Trp
1               5

<210> SEQ ID NO 13
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 gctgcatcc                                                              9

<210> SEQ ID NO 14
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
caaaaggcta acagtttccc attcact                                         27

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Lys Ala Asn Ser Phe Pro Phe Thr
1               5

<210> SEQ ID NO 17
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17
caggtgcagc tggtggagtc tgggggaggc gtggtccagc ctgggaggtc cctgagactc      60
tcctgtgcag cctctggatt caccttcagt agctatggca tgcactgggt ccgccaggct     120
ccaggcaagg ggctggagtg ggtggcagtt atatcaaatg atggaagtaa taaatactat     180
gtagattccg tgaagggccg attcaccatg gcagagaca attccaagaa cacgctgtat     240
ctccaaatga acagcctgag agttgaggac acggctgtgt attactgtgc gaaaggggct     300
ggaactcttt actactacta ctacggtatg gacgtctggg gccaagggac cacggtcacc     360

-continued gtctcctca                                                                    369

<210> SEQ ID NO 18
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Ser Asn Asp Gly Ser Asn Lys Tyr Tyr Val Asp Ser Val
    50                  55                  60

Lys Gly Arg Phe Thr Met Gly Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Gly Ala Gly Thr Leu Tyr Tyr Tyr Tyr Gly Met Asp Val
            100                 105                 110

Trp Gly Gln Gly Thr Thr Val Thr Val Ser Ser
        115                 120

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
ggattcacct tcagtagcta tggc                                                   24

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Phe Thr Phe Ser Ser Tyr Gly
1               5

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
atatcaaatg atggaagtaa taaa                                                   24

```
<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ile Ser Asn Asp Gly Ser Asn Lys
1               5

<210> SEQ ID NO 23
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gcgaaagggg ctggaactct ttactactac tactacggta tggacgtc                48

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Lys Gly Ala Gly Thr Leu Tyr Tyr Tyr Tyr Tyr Gly Met Asp Val
1               5                   10                  15

<210> SEQ ID NO 25
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gacatccaga tgacccagtc tccttccacc ctgtctgcat ctgtaggaaa cagagtcacc      60
atcacttgcc gggccagtca aagtattagt agctggttgg cctggtatca acaaaaacca     120
gggaaagccc ctaagttcct gatctataag gcgtctagtt tagaaagtgg ggtcccatca     180
aggttcagcg gcagtggatc tgggacagaa ttcactctca ccatcaccag cctgcagcct     240
gatgattttg caacttatta ctgccaacag tacaatattt attcgtggac gttcggccaa     300
gggaccaagg tggaaatcaa a                                               321

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Pro Ser Thr Leu Ser Ala Ser Val Gly
1               5                   10                  15

Asn Arg Val Thr Ile Thr Cys Arg Ala Ser Gln Ser Ile Ser Ser Trp
            20                  25                  30
```

```
Leu Ala Trp Tyr Gln Gln Lys Pro Gly Lys Ala Pro Lys Phe Leu Ile
        35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Thr Ser Leu Gln Pro
65                  70                  75                  80

Asp Asp Phe Ala Thr Tyr Tyr Cys Gln Gln Tyr Asn Ile Tyr Ser Trp
                85                  90                  95

Thr Phe Gly Gln Gly Thr Lys Val Glu Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
caaagtatta gtagctgg                                                    18

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Ile Ser Ser Trp
1               5

<210> SEQ ID NO 29
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29 aaggcgtct                                                              9

<210> SEQ ID NO 30
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 31
caacagtaca atatttattc gtggacg                                              27

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln Tyr Asn Ile Tyr Ser Trp Thr
1               5

<210> SEQ ID NO 33
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
caggtgcagc tggtggagtc tggggggaggc gtggtccagc ctgggaggtc cctgagactc       60
tcctgtgcag cctctggatt caccttcagt acctatggca tgcactgggt ccgccaggct      120
ccaggcaagg ggctggagtg gatggcagtt atatcatttg atagaggtaa taaatactat      180
gcagactccg tgaagggccg attcaccatc tccagagaca attccaagaa cacgctgtat      240
ctgcaaatga acagcctgag agctgaggac acggctgtgt attactgtgc gaaaggggggg     300 ggttcgggga ctttctacta ctactacggt atggacgtct ggggccaagg gaccacggtc      360
accgtctcct ca                                                          372

<210> SEQ ID NO 34
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Thr Tyr
            20                  25                  30

Gly Met His Trp Val Arg Gln Ala Pro Gly Lys Gly Leu Glu Trp Met
        35                  40                  45

Ala Val Ile Ser Phe Asp Arg Gly Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Gly Ser Gly Thr Phe Tyr Tyr Tyr Tyr Gly Met Asp
            100                 105                 110

Val Trp Gly Gln Gly Thr Thr Val Thr Val Ser Ser
        115                 120
```

-continued

```
<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
ggattcacct tcagtaccta tggc                                            24

<210> SEQ ID NO 36
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Phe Thr Phe Ser Thr Tyr Gly
1               5

<210> SEQ ID NO 37
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
atatcatttg atagaggtaa taaa                                            24

<210> SEQ ID NO 38
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Ser Phe Asp Arg Gly Asn Lys
1               5

<210> SEQ ID NO 39
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39
gcgaaagggg ggggttcggg gactttctac tactactacg gtatggacgt c             51

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ala Lys Gly Gly Gly Ser Gly Thr Phe Tyr Tyr Tyr Tyr Gly Met Asp
1               5                  10                  15
```

-continued

Val

<210> SEQ ID NO 41
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gacatccaga tgacccagtc tccatcttcc gtgtctgcat ctgtaggaaa cagagtcacc      60
atcacttgtc gggcgagtca gggtattagc agctggttag cctggtatca ccagaaacca     120
gggaaagtcc ctaaggtcct gatctatgct gcatccagtt tgcaaagtgg ggtcccatca     180
aggttcagcg gcagtggatc tgggacagat ttcactctca ccatcagcag cctgcagcct     240
gaagattttg caacttacta ttgtcaacag gctaacagtt tcccattcac tttcggccct     300
gggaccaaag tggatatcaa acga                                            324

<210> SEQ ID NO 42
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Asp Ile Gln Met Thr Gln Ser Pro Ser Ser Val Ser Ala Ser Val Gly
1               5                   10                  15

Asn Arg Val Thr Ile Thr Cys Arg Ala Ser Gln Gly Ile Ser Ser Trp
            20                  25                  30

Leu Ala Trp Tyr His Gln Lys Pro Gly Lys Val Pro Lys Val Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Glu Ile Lys Arg
            100                 105

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
cagggtatta gcagctgg                                                    18

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gly Ile Ser Ser Trp
1               5

<210> SEQ ID NO 45
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 gctgcatcc                                                                          9

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ala Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
caacaggcta acagtttccc attcact                                          27

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Gln Ala Asn Ser Phe Pro Phe Thr
1               5

<210> SEQ ID NO 49
<211> LENGTH: 375
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 49
caggtacagc tgcagcagtc aggtccagga ctggtgaaac cctcgcagac cctctcactc       60
acctgtgcca tctccgggga cagtgtctct agcaacagtc ctgcttggaa ctggatcagg      120
cagtccccat cgagaggcct tgagtggctg ggaaggacat actacaggtc caagtggtat      180
aatgattatg cagtgtctgt gagaggtcga ataaccatca acccagacac atccaataac      240

-continued

```
cagttctccc tacatctgaa ctctgtgact cccgaggaca cggcgatgta ttactgtgca       300
agagacaagg gtctaacagc tcgtccgacc tactttgact actggggcca gggaaccctg       360
gtcaccgtct cctca                                                        375
```

```
<210> SEQ ID NO 50
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Pro Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Arg Gly Arg Ile Thr Ile Asn Pro Asp Thr Ser Asn Asn
65                  70                  75                  80

Gln Phe Ser Leu His Leu Asn Ser Val Thr Pro Glu Asp Thr Ala Met
                85                  90                  95

Tyr Tyr Cys Ala Arg Asp Lys Gly Leu Thr Ala Arg Pro Thr Tyr Phe
            100                 105                 110

Asp Tyr Trp Gly Gln Gly Thr Leu Val Thr Val Ser Ser
        115                 120                 125

<210> SEQ ID NO 51
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
ggggacagtg tctctagcaa cagtcctgct                                        30

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Asp Ser Val Ser Ser Asn Ser Pro Ala
1               5                   10

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
```

-continued

```
acatactaca ggtccaagtg gtataat                                    27

<210> SEQ ID NO 54
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Tyr Tyr Arg Ser Lys Trp Tyr Asn
1               5

<210> SEQ ID NO 55
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
gcaagagaca agggtctaac agctcgtccg acctactttg actac             45

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ala Arg Asp Lys Gly Leu Thr Ala Arg Pro Thr Tyr Phe Asp Tyr
1               5                   10                  15

<210> SEQ ID NO 57
<211> LENGTH: 326
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 57
gacatccaga tgacccagtc tccttccacc ctgtctgcat ctgtaggaga cagagtcacc     60
atcacttgcc gggccagtca gagtattaat tactggttgg cctggtatca gcagaaacca    120
gggaaagccc ctaagcccct tatctataag gcgtctagtt tagaaagtgg ggtcccatca    180
aggttcagcg gcagtggatc tgggacagag ttcactctca ccatcagcag cctgcagcct    240
gacgatttta caacttatta ctgccaacag tataatagtt attctccgac gttcggccaa    300
gggaccaagg tggaaatcaa acgaac                                        326

<210> SEQ ID NO 58
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Gln Met Thr Gln Ser Pro Ser Thr Leu Ser Ala Ser Val Gly
1               5                   10                  15
```

```
Asp Arg Val Thr Ile Thr Cys Arg Ala Ser Gln Ser Ile Asn Tyr Trp
            20                  25                  30

Leu Ala Trp Tyr Gln Gln Lys Pro Gly Lys Ala Pro Lys Pro Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Thr Thr Tyr Tyr Cys Gln Gln Tyr Asn Ser Tyr Ser Pro
                85                  90                  95

Thr Phe Gly Gln Gly Thr Lys Leu Glu Ile Lys Arg
            100                 105

<210> SEQ ID NO 59
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
cagagtatta attactgg                                                 18

<210> SEQ ID NO 60
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gln Ser Ile Asn Tyr Trp
1               5

<210> SEQ ID NO 61
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 61 aaggcgtct                                                           9

<210> SEQ ID NO 62
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Lys Ala Ser
1

<210> SEQ ID NO 63
<211> LENGTH: 27
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 63
caacagtata atagttattc tccgacg                                              27

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gln Gln Tyr Asn Ser Tyr Ser Pro Thr
1               5

<210> SEQ ID NO 65
<211> LENGTH: 378
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 65
gaggtgcagc tggtggagtc tggggggaggc gtgatacagc ctggggggtc cctgagactc      60
tcctgtgcag cctctggatt caccttcgat gattatgcca tgaactgggt ccgtcaaggt     120
ccagggaagg gtctggagtg ggtctctgcc ataagtggtg atggcggtag cacatactat     180
gcagactcgg tgaagggccg attcaccatc tccagagaca acagcaaaaa ctccctgtat     240
ctgcaaatga acagtctgag agctgaggac accgcctttt tttactgtgc aaaagatctc     300
cgtaatacga ttttttggagt ggttattccc gatgcttttg atatctgggg ccaagggaca     360
atggtcaccg tctcttca                                                     378

<210> SEQ ID NO 66
<211> LENGTH: 126
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Val Gln Leu Val Glu Ser Gly Gly Gly Val Ile Gln Pro Gly Gly
1               5                   10                  15

Ser Leu Arg Leu Ser Cys Ala Ala Ser Gly Phe Thr Phe Asp Asp Tyr
            20                  25                  30

Ala Met Asn Trp Val Arg Gln Gly Pro Gly Lys Gly Leu Glu Trp Val
        35                  40                  45

Ser Ala Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Phe Phe Tyr Cys
                85                  90                  95

Ala Lys Asp Leu Arg Asn Thr Ile Phe Gly Val Val Ile Pro Asp Ala
            100                 105                 110

Phe Asp Ile Trp Gly Gln Gly Thr Met Val Thr Val Ser Ser

-continued

```
          115              120              125

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
ggattcacct tcgatgatta tgcc                                        24

<210> SEQ ID NO 68
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Gly Phe Thr Phe Asp Asp Tyr Ala
1               5

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 69
ataagtggtg atggcggtag caca                                        24

<210> SEQ ID NO 70
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ile Ser Gly Asp Gly Gly Ser Thr
1               5

<210> SEQ ID NO 71
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
gcaaaagatc tccgtaatac gatttttgga gtggttattc ccgatgcttt tgatatc    57

<210> SEQ ID NO 72
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72
```

Ala Lys Asp Leu Arg Asn Thr Ile Phe Gly Val Val Ile Pro Asp Ala
1               5                   10                  15

Phe Asp Ile

<210> SEQ ID NO 73
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
gacatccaga tgacccagtc tccttccacc ctgtctgcat ctgtaggaga cagagtcacc        60
atcacttgcc gggccagtca gagcattagg agctggttgg cctggtatca gcagaaacca       120
gggaaagccc ctaaactcct gatctataag gcgtctagtt tagaaagtgg ggtcccatca       180
aggttcagcg gcagtggatc tgggacagaa ttcactctca ccatcagcag cctgcagcct       240
gatgattttg caacttatta ctgccaacaa tataatagtt attcgtacac ttttggccag       300
gggaccaagc tggagatcaa acga                                              324

<210> SEQ ID NO 74
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Arg Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Tyr
                85                  90                  95

Thr Phe Gly Gln Gly Thr Lys Leu Glu Ile Lys Arg
            100                 105

<210> SEQ ID NO 75
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
cagagcatta ggagctgg                                                      18

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gln Ser Ile Arg Ser Trp
1               5

<210> SEQ ID NO 77
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77 aaggcgtct                                                                                          9

<210> SEQ ID NO 78
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Lys Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
caacaatata atagttattc gtacact                                                                      27

<210> SEQ ID NO 80
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Gln Gln Tyr Asn Ser Tyr Ser Tyr Thr
1               5

<210> SEQ ID NO 81
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81
caggtgcagc tggtggagtc ggggggaggc ttggtcaagc ctggagggtc cctgagactc        60
tcctgtgcag cctctggatt cactttcagt gactactaca tgagctggat ccgtcaggct       120
ccagggaagg ggctggagtg ggtttcatac attggtagta gtggtgtcaa catgtactac       180

-continued gcagactctg tgaagggccg attcaccatc tccagggaca acgccaagaa ttcattatat    240
ctggaaatga acagcctgag agccgaggac acggctgttt attactgtgc gagagactct    300
tcccaactgg tttttgacta ctggggccag ggaaccctgg tcaccgtctc ctca    354

<210> SEQ ID NO 82
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 82

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Gly Ser Ser Gly Val Asn Met Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Glu Met Asn Ser Leu Arg Ala Glu Asp Thr Ala Val Tyr Tyr Cys
                85                  90                  95

Ala Arg Asp Ser Ser Gln Leu Gly Phe Asp Tyr Trp Gly Gln Gly Thr
            100                 105                 110

Leu Val Thr Val Ser Ser
        115

<210> SEQ ID NO 83
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
ggattcactt tcagtgacta ctac                                          24

<210> SEQ ID NO 84
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Phe Thr Phe Ser Asp Tyr Tyr
1               5

<210> SEQ ID NO 85
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
attggtagta gtggtgtcaa catg                                           24

<210> SEQ ID NO 86
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ile Gly Ser Ser Gly Val Asn Met
1               5

<210> SEQ ID NO 87
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gcgagagact cttcccaact gggttttgac tac                                 33

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ala Arg Asp Ser Ser Gln Leu Gly Phe Asp Tyr
1               5                   10

<210> SEQ ID NO 89
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 89
gacatccaga tgacccagtc tccatcctcc ctgtctgcat ctgtaggaga cagagtcacc        60
atcacttgcc ggacaagtca gaatattatc aacttttaa attggtatca acagaaacct       120
gggaaggccc ctaaactcct gatctatact acttccactt tacaaagtgg ggtcccatca       180
aggttcagtg gcagtggatc tgggacagat ttcactctct ccatcaatag tctacaacct       240
gaagattttg caacttactt ctgtcaacag acttacagta atccactcac tttcggcgga       300
gggaccaagg tggagatcaa acga                                            324

<210> SEQ ID NO 90
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 90

Asp Ile Gln Met Thr Gln Ser Pro Ser Ser Leu Ser Ala Ser Val Gly

-continued

```
1               5               10              15

Asp Arg Val Thr Ile Thr Cys Arg Thr Ser Gln Asn Ile Ile Asn Phe
            20              25              30

Leu Asn Trp Tyr Gln Gln Lys Pro Gly Lys Ala Pro Lys Leu Leu Ile
        35              40              45

Tyr Thr Thr Ser Thr Leu Gln Ser Gly Val Pro Ser Arg Phe Ser Gly
    50              55              60

Ser Gly Ser Gly Thr Asp Phe Thr Leu Ser Ile Asn Ser Leu Gln Pro
65              70              75              80

Glu Asp Phe Ala Thr Tyr Phe Cys Gln Gln Thr Tyr Ser Asn Pro Leu
                85              90              95

Thr Phe Gly Gly Gly Thr Lys Leu Glu Ile Lys Arg
            100             105
```

```
<210> SEQ ID NO 91
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
cagaatatta tcaacttt                                                          18

<210> SEQ ID NO 92
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Asn Ile Ile Asn Phe
1               5

<210> SEQ ID NO 93
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 93 actacttcc                                                                     9

<210> SEQ ID NO 94
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Thr Thr Ser
1

<210> SEQ ID NO 95
<211> LENGTH: 27
<212> TYPE: DNA
<213> ORGANISM: Artificial Sequence
```

-continued

<220> FEATURE:
<223> OTHER INFORMATION: Description of Artificial Sequence: Synthetic
      oligonucleotide

<400> SEQUENCE: 95
caacagactt acagtaatcc actcact                                                        27

<210> SEQ ID NO 96
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gln Gln Thr Tyr Ser Asn Pro Leu Thr
1               5

<210> SEQ ID NO 97
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
gaggtgcagc tggtgcagtc tggggggaggc gtggtccagc ctgggaggtc cctgagactc      60
tcctgtgcag cgtctggatt caccttcagt aattatggca tgcactgggt ccgccaggct     120
ccaggcaagg ggctggagtg ggtggcagtt gtttggtatg atggagataa taaatactat     180
gcagactccg tgaagggccg attcaccatc tccagagaca attccaagaa cacgctgtat     240
ctgcaaatga acagcctgag agccgaggac acggctgtgt attactgtgc gagagatatt     300
atcacatctc gcccgacttt ggactactgg ggccagggaa ccctggtcac tgtctcctca     360

<210> SEQ ID NO 98
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Val Trp Tyr Asp Gly Asp Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Ile Ile Thr Ser Arg Pro Thr Leu Asp Tyr Trp Gly Gln
            100                 105                 110

Gly Thr Leu Val Thr Val Ser Ser
        115                 120

```
<210> SEQ ID NO 99
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
ggattcacct tcagtaatta tggc                                            24

<210> SEQ ID NO 100
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Phe Thr Phe Ser Asn Tyr Gly
1               5

<210> SEQ ID NO 101
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
gtttggtatg atggagataa taaa                                            24

<210> SEQ ID NO 102
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Val Trp Tyr Asp Gly Asp Asn Lys
1               5

<210> SEQ ID NO 103
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
gcgagagata ttatcacatc tcgcccgact ttggactac                            39

<210> SEQ ID NO 104
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104
```

```
Ala Arg Asp Ile Ile Thr Ser Arg Pro Thr Leu Asp Tyr
1               5                   10
```

<210> SEQ ID NO 105
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 105

```
gacatccagt tgacccagtc tccatccttc ctgtctgcat ctgtaggaga cagagtcacc        60
atcacttgct gggccagtca gggcattaac agttatttag cctggtatca gcaaaaacca       120
gggaaagccc ctaagctcct gatctatcct gcatccactt tgcaaagtgg ggtcccatca       180
aggttcagcg gcagtggatc tgggacagaa ttcactctca caatcagcag cctgcagcct       240
gtagattttg caacttatta ctgtcaacag cttaatagtt acccgctcac tttcggcgga       300
gggaccaagg tggagatcaa acga                                              324
```

<210> SEQ ID NO 106
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

```
Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Asn Ser Tyr
            20                  25                  30

Leu Ala Trp Tyr Gln Gln Lys Pro Gly Lys Ala Pro Lys Leu Leu Ile
        35                  40                  45

Tyr Pro Ala Ser Thr Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Val Asp Phe Ala Thr Tyr Tyr Cys Gln Gln Leu Asn Ser Tyr Pro Leu
                85                  90                  95

Thr Phe Gly Gly Gly Thr Lys Val Glu Ile Lys Arg
            100                 105
```

<210> SEQ ID NO 107
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107

```
cagggcatta acagttat                                                      18
```

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Gln Gly Ile Asn Ser Tyr
1               5

<210> SEQ ID NO 109
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109 cctgcatcc                                                                                    9

<210> SEQ ID NO 110
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Pro Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
caacagctta atagttaccc gctcact                                                                27

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Gln Gln Leu Asn Ser Tyr Pro Leu Thr
1               5

<210> SEQ ID NO 113
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 113
caggtgcagc tggtggagtc ggggggaggc ttggtcaagc ctggagggtc cctgagactc      60
tcctgtgcag cctctggatt caccttcagt gactactaca tgagctggat ccgccaggct     120
ccagggaagg ggctggagtg ggtttcatac attagtagta gtggtagtac catatactac     180
gcagactctg tgaagggccg attcaccata tccagggaca acgccaagaa ctcactgtat     240

-continued

```
ctgcaaatga acagcctgag agccgaggac acggccgtgt attactgtgc gagagattct       300
tcccaactgg gttttgacta ctggggccag ggaaccctgg tcaccgtctc ctca              354
```

```
<210> SEQ ID NO 114
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ile Tyr Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ser Ser Gln Leu Gly Phe Asp Tyr Trp Gly Gln Gly Thr
            100                 105                 110

Leu Val Thr Val Ser Ser
        115
```

```
<210> SEQ ID NO 115
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ggattcacct tcagtgacta ctac                                               24
```

```
<210> SEQ ID NO 116
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Phe Thr Phe Ser Asp Tyr Tyr
1               5
```

```
<210> SEQ ID NO 117
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
attagtagta gtggtagtac cata                                               24
```

```
<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ile Ser Ser Ser Gly Ser Thr Ile
1               5

<210> SEQ ID NO 119
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
gcgagagatt cttcccaact gggttttgac tac                                   33

<210> SEQ ID NO 120
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Ala Arg Asp Ser Ser Gln Leu Gly Phe Asp Tyr
1               5                   10

<210> SEQ ID NO 121
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 121
gacatccaga tgacccagtc tccatcctcc ctgtctgcat ctgtaggaga cagagtcacc      60
atcacttgcc gggcaagtca gagcattatc agctttttaa attggtatca gcagaaacca     120
gggaaggccc ctaagctcct gatctatact gcatccagtt tgcaaagtgg ggtcccatca     180
aggttcagtg gcagtggatc tgggacagat ttcactctca ccatcagcag tctacaacct     240
gaagattttg caacttacta ctgtcaacag acttacagta atccgctcac tttcggcgga     300
gggaccaagg tggaaatcaa acga                                            324

<210> SEQ ID NO 122
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ile Ser Phe
```

```
             20              25              30

Leu Asn Trp Tyr Gln Gln Lys Pro Gly Lys Ala Pro Lys Leu Leu Ile
         35              40              45

Tyr Thr Ala Ser Ser Leu Gln Ser Gly Val Pro Ser Arg Phe Ser Gly
     50              55              60

Ser Gly Ser Gly Thr Asp Phe Thr Leu Thr Ile Ser Ser Leu Gln Pro
65              70              75              80

Glu Asp Phe Ala Thr Tyr Tyr Cys Gln Gln Thr Tyr Ser Asn Pro Leu
                85              90              95

Thr Phe Gly Gly Gly Thr Lys Val Glu Ile Lys Arg
            100             105
```

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123
cagagcatta tcagcttt                                                18

<210> SEQ ID NO 124
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gln Ser Ile Ile Ser Phe
1               5

<210> SEQ ID NO 125
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125 actgcatcc                                                           9

<210> SEQ ID NO 126
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Thr Ala Ser
1

<210> SEQ ID NO 127
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 127
caacagactt acagtaatcc gctcact                                                          27

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Gln Gln Thr Tyr Ser Asn Pro Leu Thr
1               5

<210> SEQ ID NO 129
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 129
caggtgcagc tggtacagtc tggacctgag gtgaagaagc ctggggcctc agtgagggtc        60
tcctgtaagg cttctggtta ccttagtgac tttattatca cctgggtgcg acaggcccct       120
ggacaagggc ttgagtggat gggatggatc agcacttaca gtggtgacac agactctgca       180
ccgaagttcc agggcagagt caccatgacc acagacacat ccacgactac agtcttcttg       240
gaactgagga gcctgagatc tgacgacacg gccgtgtatt attgtgcgag agggcggctg       300
tttgactact ggggccaggg aaccctggtc accgtctcct ca                          342

<210> SEQ ID NO 130
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Gln Val Gln Leu Val Gln Ser Gly Pro Glu Val Lys Lys Pro Gly Ala
1               5                   10                  15

Ser Val Arg Val Ser Cys Lys Ala Ser Gly Tyr Leu Ser Asp Phe Ile
            20                  25                  30

Ile Thr Trp Val Arg Gln Ala Pro Gly Gln Gly Leu Glu Trp Met Gly
        35                  40                  45

Trp Ile Ser Thr Tyr Ser Gly Asp Thr Asp Ser Ala Pro Lys Phe Gln
    50                  55                  60

Gly Arg Val Thr Met Thr Thr Asp Thr Ser Thr Thr Thr Val Phe Leu
65                  70                  75                  80

Glu Leu Arg Ser Leu Arg Ser Asp Asp Thr Ala Val Tyr Tyr Cys Ala
                85                  90                  95

Arg Gly Arg Leu Phe Asp Tyr Trp Gly Gln Gly Thr Leu Val Thr Val
            100                 105                 110

Ser Ser

<210> SEQ ID NO 131
<211> LENGTH: 21

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ggttacctta gtgactttat t                                                       21

<210> SEQ ID NO 132
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Tyr Leu Ser Asp Phe Ile
1               5

<210> SEQ ID NO 133
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
atcagcactt acagtggtga caca                                                    24

<210> SEQ ID NO 134
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Ile Ser Thr Tyr Ser Gly Asp Thr
1               5

<210> SEQ ID NO 135
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
gcgagagggc ggctgtttga ctac                                                    24

<210> SEQ ID NO 136
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ala Arg Gly Arg Leu Phe Asp Tyr
1               5
```

<210> SEQ ID NO 137
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 137
gatgttgtga tgactcagtc tccactctcc ctgcccgtca cccttggaca gccggcctcc        60
atctcctgca ggtctagtca aagcctcgta tacagtgatg gaaacaccta cttgaattgg       120
tttcaacaga ggccaggcca atctccaagg cgcctaattt ataaggtttc taaccgggac       180
tctggggtcc cagacagatt cagcggcagt gggtcaggca ctgatttcac actgaaaatc       240
agcagggtgg aggctgagga tgttggggtt tattactgca tgcaaggtac acactggccg       300
tacacttttg gccaggggac caagctggag atcaaacga                              339

<210> SEQ ID NO 138
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 138

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Tyr Thr Phe Gly Gln Gly Thr Lys Leu Glu Ile Lys
            100                 105                 110

Arg

<210> SEQ ID NO 139
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 139
caaagcctcg tatacagtga tggaaacacc tac                                     33

<210> SEQ ID NO 140
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

Gln Ser Leu Val Tyr Ser Asp Gly Asn Thr Tyr
1               5                   10

<210> SEQ ID NO 141
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 141 aaggtttct                                                                                              9

<210> SEQ ID NO 142
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Lys Val Ser
1

<210> SEQ ID NO 143
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 143
atgcaaggta cacactggcc gtacact                                                                         27

<210> SEQ ID NO 144
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Met Gln Gly Thr His Trp Pro Tyr Thr
1               5

<210> SEQ ID NO 145
<211> LENGTH: 354
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 145
caggtgcagc tggtggagtc tgggggagtc tcggtcaagc ctggagggtc cctgcgactc      60
tcctgtgcag cctctggatt caccttcagt gactactaca tgagctggat ccgccaggcg     120
ccagggaagg gactggagtg ggtttcgtac attggtagta gtggtactaa tgactactac     180
gcagactctg tgaagggccg attcaccatc tccagggaca cgccaagaa ctcactgtat      240 cttcaaatgg acagcctgag agccgaggac acggccgtct attactgtgc gagagattct     300

-continued

```
tcccaaatgg gtttttgacta ctggggccag ggaaccctgg tcactgtctc ctca           354
```

```
<210> SEQ ID NO 146
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Gln Val Gln Leu Val Glu Ser Gly Gly Val Ser Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Gly Ser Ser Gly Thr Asn Asp Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Val Tyr Tyr Cys
                85                  90                  95

Ala Arg Asp Ser Ser Gln Met Gly Phe Asp Tyr Trp Gly Gln Gly Thr
            100                 105                 110

Leu Val Thr Val Ser Ser
        115

<210> SEQ ID NO 147
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 147
ggattcacct tcagtgacta ctac                                             24

<210> SEQ ID NO 148
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Phe Thr Phe Ser Asp Tyr Tyr
1               5

<210> SEQ ID NO 149
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 149
attggtagta gtggtactaa tgac                                             24

<210> SEQ ID NO 150
```

```
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ile Gly Ser Ser Gly Thr Asn Asp
1               5

<210> SEQ ID NO 151
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 151
gcgagagatt cttcccaaat gggttttgac tac                                33

<210> SEQ ID NO 152
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ala Arg Asp Ser Ser Gln Met Gly Phe Asp Tyr
1               5                   10

<210> SEQ ID NO 153
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 153
gacatccaga tgacccagtc tccatcctcc ctgtctgctt ctgtgggaga cagagtcacc     60
atcacttgcc gggcaagtca gaacattatc aactttttaa attggtatca gcagagacca    120
gggaaagccc ctcagctcct gatctatgtt gcagccagct tgcagagtgg ggtcccatca    180
aggttcactg gcagtggata tgggacagat ttcactctca ccatcagcag tctgcaacct    240
gaggatttcg caacttacta ctgtcaacag acttacacta acccgctcac tttcggcgga    300
gggaccaagg tggagatcaa acga                                          324

<210> SEQ ID NO 154
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 154

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ile Asn Phe
            20                  25                  30
```

```
Leu Asn Trp Tyr Gln Gln Arg Pro Gly Lys Ala Pro Gln Leu Leu Ile
        35                  40                  45

Tyr Val Ala Ala Ser Leu Gln Ser Gly Val Pro Ser Arg Phe Thr Gly
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Thr Asn Pro Leu
                85                  90                  95

Thr Phe Gly Gly Gly Thr Lys Val Glu Ile Lys Arg
            100                 105
```

```
<210> SEQ ID NO 155
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 155
cagaacatta tcaacttt                                                      18
```

```
<210> SEQ ID NO 156
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Gln Asn Ile Ile Asn Phe
1               5
```

```
<210> SEQ ID NO 157
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157 gttgcagcc                                                                 9
```

```
<210> SEQ ID NO 158
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Val Ala Ala
1
```

```
<210> SEQ ID NO 159
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
```

-continued

```
caacagactt acactaaccc gctcact                                        27
```

<210> SEQ ID NO 160
<211> LENGTH: 9
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 160

Gln Gln Thr Tyr Thr Asn Pro Leu Thr
1               5

<210> SEQ ID NO 161
<211> LENGTH: 460
<212> TYPE: PRT
<213> ORGANISM: Homo sapiens

<400> SEQUENCE: 161

Met Phe Thr Ile Lys Leu Leu Leu Phe Ile Val Pro Leu Val Ile Ser
1               5                   10                  15

Ser Arg Ile Asp Gln Asp Asn Ser Ser Phe Asp Ser Leu Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Ile Leu Leu Gln Gln Lys Val Lys Tyr Leu Glu Glu Gln
    130                 135                 140

Leu Thr Asn Leu Ile Gln Asn Gln Pro Glu Thr Pro Glu His Pro Glu
145                 150                 155                 160

Val Thr Ser Leu Lys Thr Phe Val Glu Lys Gln Asp Asn Ser Ile Lys
                165                 170                 175

Asp Leu Leu Gln Thr Val Glu Asp Gln Tyr Lys Gln Leu Asn Gln Gln
                180                 185                 190

His Ser Gln Ile Lys Glu Ile Glu Asn Gln Leu Arg Arg Thr Ser Ile
            195                 200                 205

Gln Glu Pro Thr Glu Ile Ser Leu Ser Ser Lys Pro Arg Ala Pro Arg
    210                 215                 220

Thr Thr Pro Phe Leu Gln Leu Asn Glu Ile Arg Asn Val Lys His Asp
225                 230                 235                 240

Gly Ile Pro Ala Glu Cys Thr Thr Ile Tyr Asn Arg Gly Glu His Thr
                245                 250                 255

Ser Gly Met Tyr Ala Ile Arg Pro Ser Asn Ser Gln Val Phe His Val
            260                 265                 270

Tyr Cys Asp Val Ile Ser Gly Ser Pro Trp Thr Leu Ile Gln His Arg
            275                 280                 285
```

-continued

```
Ile Asp Gly Ser Gln Asn Phe Asn Glu Thr Trp Glu Asn Tyr Lys Tyr
    290                 295                 300

Gly Phe Gly Arg Leu Asp Gly Glu Phe Trp Leu Gly Leu Glu Lys Ile
305                 310                 315                 320

Tyr Ser Ile Val Lys Gln Ser Asn Tyr Val Leu Arg Ile Glu Leu Glu
                325                 330                 335

Asp Trp Lys Asp Asn Lys His Tyr Ile Glu Tyr Ser Phe Tyr Leu Gly
            340                 345                 350

Asn His Glu Thr Asn Tyr Thr Leu His Leu Val Ala Ile Thr Gly Asn
        355                 360                 365

Val Pro Asn Ala Ile Pro Glu Asn Lys Asp Leu Val Phe Ser Thr Trp
    370                 375                 380

Asp His Lys Ala Lys Gly His Phe Asn Cys Pro Glu Gly Tyr Ser Gly
385                 390                 395                 400

Gly Trp Trp Trp His Asp Glu Cys Gly Glu Asn Asn Leu Asn Gly Lys
                405                 410                 415

Tyr Asn Lys Pro Arg Ala Lys Ser Lys Pro Glu Arg Arg Arg Gly Leu
            420                 425                 430

Ser Trp Lys Ser Gln Asn Gly Arg Leu Tyr Ser Ile Lys Ser Thr Lys
        435                 440                 445

Met Leu Ile His Pro Thr Asp Ser Glu Ser Phe Glu
    450                 455                 460

<210> SEQ ID NO 162
<211> LENGTH: 1383
<212> TYPE: DNA
<213> ORGANISM: Homo sapiens

<400> SEQUENCE: 162
atgttcacaa ttaagctcct tctttttatt gttcctctag ttatttcctc cagaattgat      60
caagacaatt catcatttga ttctctatct ccagagccaa aatcaagatt tgctatgtta     120
gacgatgtaa aaattttagc caatggcctc cttcagttgg acatggtct  taaagacttt     180 gtccataaga cgaagggcca aattaatgac atatttcaaa aactcaacat atttgatcag     240 tcttttttatg atctatcgct gcaaaccagt gaaatcaaag aagaagaaaa ggaactgaga     300
agaactacat ataaactaca agtcaaaaat gaagaggtaa agaatatgtc acttgaactc     360
aactcaaaac ttgaaagcct cctagaagaa aaaattctac ttcaacaaaa agtgaaatat     420
ttagaagagc aactaactaa cttaattcaa aatcaacctg aaactccaga cacccagaa      480 gtaacttcac ttaaaacttt tgtagaaaaa caagataata gcatcaaaga ccttctccag     540
accgtggaag accaatataa acaattaaac caacagcata gtcaaataaa agaaatagaa     600
aatcagctca gaaggactag tattcaagaa cccacagaaa tttctctatc ttccaagcca     660
agagcaccaa gaactactcc ctttcttcag ttgaatgaaa taagaaatgt aaaacatgat     720
ggcattcctg ctgaatgtac caccatttat aacagaggtg aacatacaag tggcatgtat     780
gccatcagac ccagcaactc tcaagttttt catgtctact gtgatgttat atcaggtagt     840
ccatggacat taattcaaca tcgaatagat ggatcacaaa acttcaatga aacgtgggag     900
aactacaaat atggttttgg gaggcttgat ggagaatttt ggttgggcct agagaagata     960
tactccatag tgaagcaatc taattatgtt ttacgaattg agttggaaga ctggaaagac    1020
aacaaacatt atattgaata ttcttttttac ttgggaaatc acgaaaccaa ctatacgcta    1080
catctagttg cgattactgg caatgtcccc aatgcaatcc cggaaaacaa agatttggtg    1140
```

-continued

```
ttttctactt gggatcacaa agcaaaagga cacttcaact gtccagaggg ttattcagga      1200
ggctggtggt ggcatgatga gtgtggagaa acaacctaa atggtaaata taacaaacca      1260
agagcaaaat ctaagccaga gaggagaaga ggattatctt ggaagtctca aaatggaagg     1320
ttatactcta taaatcaac caaaatgttg atccatccaa cagattcaga aagctttgaa     1380
tga                                                                  1383
```

```
<210> SEQ ID NO 163
<211> LENGTH: 455
<212> TYPE: PRT
<213> ORGANISM: Mus musculus

<400> SEQUENCE: 163

Met His Thr Ile Lys Leu Phe Leu Phe Val Val Pro Leu Val Ile Ala
1               5                   10                  15

Ser Arg Val Asp Pro Asp Leu Ser Ser Phe Asp Ser Ala Pro Ser Glu
                20                  25                  30

Pro Lys Ser Arg Phe Ala Met Leu Asp Asp Val Lys Ile Leu Ala Asn
            35                  40                  45

Gly Leu Leu Gln Leu Gly His Gly Leu Lys Asp Phe Val His Lys Thr
        50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Arg Thr Asn Glu Ile Lys Glu Glu Glu
                85                  90                  95

Lys Glu Leu Arg Arg Thr Thr Ser Thr Leu Gln Val Lys Asn Glu Glu
            100                 105                 110

Val Lys Asn Met Ser Val Glu Leu Asn Ser Lys Leu Glu Ser Leu Leu
        115                 120                 125

Glu Glu Lys Thr Ala Leu Gln His Lys Val Arg Ala Leu Glu Glu Gln
        130                 135                 140

Leu Thr Asn Leu Ile Leu Ser Pro Ala Gly Ala Gln Glu His Pro Glu
145                 150                 155                 160

Val Thr Ser Leu Lys Ser Phe Val Glu Gln Gln Asp Asn Ser Ile Arg
                165                 170                 175

Glu Leu Leu Gln Ser Val Glu Glu Gln Tyr Lys Gln Leu Ser Gln Gln
            180                 185                 190

His Met Gln Ile Lys Glu Ile Glu Lys Gln Leu Arg Lys Thr Gly Ile
        195                 200                 205

Gln Glu Pro Ser Glu Asn Ser Leu Ser Ser Lys Ser Arg Ala Pro Arg
    210                 215                 220

Thr Thr Pro Pro Leu Gln Leu Asn Glu Thr Glu Asn Thr Glu Gln Asp
225                 230                 235                 240

Asp Leu Pro Ala Asp Cys Ser Ala Val Tyr Asn Arg Gly Glu His Thr
                245                 250                 255

Ser Gly Val Tyr Thr Ile Lys Pro Arg Asn Ser Gln Gly Phe Asn Val
            260                 265                 270

Tyr Cys Asp Thr Gln Ser Gly Ser Pro Trp Thr Leu Ile Gln His Arg
        275                 280                 285

Lys Asp Gly Ser Gln Asp Phe Asn Glu Thr Trp Glu Asn Tyr Glu Lys
    290                 295                 300

Gly Phe Gly Arg Leu Asp Gly Glu Phe Trp Leu Gly Leu Glu Lys Ile
305                 310                 315                 320

Tyr Ala Ile Val Gln Gln Ser Asn Tyr Ile Leu Arg Leu Glu Leu Gln
```

-continued

```
                    325                 330                 335

Asp Trp Lys Asp Ser Lys His Tyr Val Glu Tyr Ser Phe His Leu Gly
            340                 345                 350

Ser His Glu Thr Asn Tyr Thr Leu His Val Ala Glu Ile Ala Gly Asn
            355                 360                 365

Ile Pro Gly Ala Leu Pro Glu His Thr Asp Leu Met Phe Ser Thr Trp
            370                 375                 380

Asn His Arg Ala Lys Gly Gln Leu Tyr Cys Pro Glu Ser Tyr Ser Gly
385                 390                 395                 400

Gly Trp Trp Trp Asn Asp Ile Cys Gly Glu Asn Asn Leu Asn Gly Lys
                405                 410                 415

Tyr Asn Lys Pro Arg Thr Lys Ser Arg Pro Glu Arg Arg Gly Ile
            420                 425                 430

Tyr Trp Arg Pro Gln Ser Arg Lys Leu Tyr Ala Ile Lys Ser Ser Lys
            435                 440                 445

Met Met Leu Gln Pro Thr Thr
    450                 455

<210> SEQ ID NO 164
<211> LENGTH: 406
<212> TYPE: PRT
<213> ORGANISM: Homo sapiens

<400> SEQUENCE: 164

Met Ser Gly Ala Pro Thr Ala Gly Ala Ala Leu Met Leu Cys Ala Ala
1               5                   10                  15

Thr Ala Val Leu Leu Ser Ala Gln Gly Gly Pro Val Gln Ser Lys Ser
            20                  25                  30

Pro Arg Phe Ala Ser Trp Asp Glu Met Asn Val Leu Ala His Gly Leu
            35                  40                  45

Leu Gln Leu Gly Gln Gly Leu Arg Glu His Ala Glu Arg Thr Arg Ser
    50                  55                  60

Gln Leu Ser Ala Leu Glu Arg Arg Leu Ser Ala Cys Gly Ser Ala Cys
65                  70                  75                  80

Gln Gly Thr Glu Gly Ser Thr Asp Leu Pro Leu Ala Pro Glu Ser Arg
                85                  90                  95

Val Asp Pro Glu Val Leu His Ser Leu Gln Thr Gln Leu Lys Ala Gln
            100                 105                 110

Asn Ser Arg Ile Gln Gln Leu Phe His Lys Val Ala Gln Gln Gln Arg
            115                 120                 125

His Leu Glu Lys Gln His Leu Arg Ile Gln His Leu Gln Ser Gln Phe
    130                 135                 140

Gly Leu Leu Asp His Lys His Leu Asp His Glu Val Ala Lys Pro Ala
145                 150                 155                 160

Arg Arg Lys Arg Leu Pro Glu Met Ala Gln Pro Val Asp Pro Ala His
                165                 170                 175

Asn Val Ser Arg Leu His Arg Leu Pro Arg Asp Cys Gln Glu Leu Phe
            180                 185                 190

Gln Val Gly Glu Arg Gln Ser Gly Leu Phe Glu Ile Gln Pro Gln Gly
            195                 200                 205

Ser Pro Pro Phe Leu Val Asn Cys Lys Met Thr Ser Asp Gly Gly Trp
    210                 215                 220

Thr Val Ile Gln Arg Arg His Asp Gly Ser Val Asp Phe Asn Arg Pro
225                 230                 235                 240
```

```
Trp Glu Ala Tyr Lys Ala Gly Phe Gly Asp Pro His Gly Glu Phe Trp
            245                 250                 255

Leu Gly Leu Glu Lys Val His Ser Ile Thr Gly Asp Arg Asn Ser Arg
            260                 265                 270

Leu Ala Val Gln Leu Arg Asp Trp Asp Gly Asn Ala Glu Leu Leu Gln
            275                 280                 285

Phe Ser Val His Leu Gly Gly Glu Asp Thr Ala Tyr Ser Leu Gln Leu
            290                 295                 300

Thr Ala Pro Val Ala Gly Gln Leu Gly Ala Thr Thr Val Pro Pro Ser
305                 310                 315                 320

Gly Leu Ser Val Pro Phe Ser Thr Trp Asp Gln Asp His Asp Leu Arg
            325                 330                 335

Arg Asp Lys Asn Cys Ala Lys Ser Leu Ser Gly Gly Trp Trp Phe Gly
            340                 345                 350

Thr Cys Ser His Ser Asn Leu Asn Gly Gln Tyr Phe Arg Ser Ile Pro
            355                 360                 365

Gln Gln Arg Gln Lys Leu Lys Lys Gly Ile Phe Trp Lys Thr Trp Arg
            370                 375                 380

Gly Arg Tyr Tyr Pro Leu Gln Ala Thr Thr Met Leu Ile Gln Pro Met
385                 390                 395                 400

Ala Ala Glu Ala Ala Ser
            405

<210> SEQ ID NO 165
<211> LENGTH: 386
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Ser Arg Ile Asp Gln Asp Asn Ser Ser Phe Asp Ser Leu Ser Pro Glu
1               5                   10                  15

Pro Lys Ser Arg Phe Ala Met Leu Asp Asp Val Lys Ile Leu Ala Asn
            20                  25                  30

Gly Leu Leu Gln Leu Gly His Gly Leu Lys Asp Phe Val His Lys Thr
            35                  40                  45

Lys Gly Gln Ile Asn Asp Ile Phe Gln Lys Leu Asn Ile Phe Asp Gln
            50                  55                  60

Ser Phe Tyr Asp Leu Ser Leu Gln Thr Ser Glu Ile Lys Glu Glu Glu
65                  70                  75                  80

Lys Glu Leu Arg Arg Thr Thr Tyr Lys Leu Gln Val Lys Asn Glu Glu
            85                  90                  95

Val Lys Asn Met Ser Leu Glu Leu Asn Ser Lys Leu Glu Ser Leu Leu
            100                 105                 110

Glu Glu Lys Ile Leu Leu Gln Gln Lys Val Lys Tyr Leu Glu Glu Gln
            115                 120                 125

Leu Thr Asn Leu Ile Gln Asn Gln Pro Glu Thr Pro Glu His Pro Glu
            130                 135                 140

Val Thr Ser Leu Lys Thr Phe Val Glu Glu Pro Arg Gly Pro Thr Ile
145                 150                 155                 160

Lys Pro Cys Pro Pro Cys Lys Cys Pro Ala Pro Asn Leu Leu Gly Gly
            165                 170                 175

Pro Ser Val Phe Ile Phe Pro Pro Lys Ile Lys Asp Val Leu Met Ile
            180                 185                 190
```

-continued

```
Ser Leu Ser Pro Ile Val Thr Cys Val Val Val Asp Val Ser Glu Asp
        195                 200                 205

Asp Pro Asp Val Gln Ile Ser Trp Phe Val Asn Asn Val Glu Val His
    210                 215                 220

Thr Ala Gln Thr Gln Thr His Arg Glu Asp Tyr Asn Ser Thr Leu Arg
225                 230                 235                 240

Val Val Ser Ala Leu Pro Ile Gln His Gln Asp Trp Met Ser Gly Lys
                245                 250                 255

Glu Phe Lys Cys Lys Val Asn Asn Lys Asp Leu Pro Ala Pro Ile Glu
                260                 265                 270

Arg Thr Ile Ser Lys Pro Lys Gly Ser Val Arg Ala Pro Gln Val Tyr
                275                 280                 285

Val Leu Pro Pro Pro Glu Glu Glu Met Thr Lys Lys Gln Val Thr Leu
    290                 295                 300

Thr Cys Met Val Thr Asp Phe Met Pro Glu Asp Ile Tyr Val Glu Trp
305                 310                 315                 320

Thr Asn Asn Gly Lys Thr Glu Leu Asn Tyr Lys Asn Thr Glu Pro Val
                325                 330                 335

Leu Asp Ser Asp Gly Ser Tyr Phe Met Tyr Ser Lys Leu Arg Val Glu
                340                 345                 350

Lys Lys Asn Trp Val Glu Arg Asn Ser Tyr Ser Cys Ser Val Val His
                355                 360                 365

Glu Gly Leu His Asn His His Thr Thr Lys Ser Phe Ser Arg Thr Pro
    370                 375                 380

Gly Lys
385
```

```
<210> SEQ ID NO 166
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166
```

```
Gly Ala Pro Ser Arg Val Asp Pro Asp Leu Ser Ser Phe Asp Ser Ala
1               5                   10                  15

Pro Ser Glu Pro Lys Ser Arg Phe Ala Met Leu Asp Asp Val Lys Ile
                20                  25                  30

Leu Ala Asn Gly Leu Leu Gln Leu Gly His Gly Leu Lys Asp Phe Val
        35                  40                  45

His Lys Thr Lys Gly Gln Ile Asn Asp Ile Phe Gln Lys Leu Asn Ile
    50                  55                  60

Phe Asp Gln Ser Phe Tyr Asp Leu Ser Leu Arg Thr Asn Glu Ile Lys
65                  70                  75                  80

Glu Glu Glu Lys Glu Leu Arg Arg Thr Thr Ser Thr Leu Gln Val Lys
                85                  90                  95

Asn Glu Glu Val Lys Asn Met Ser Val Glu Leu Asn Ser Lys Leu Glu
                100                 105                 110

Ser Leu Leu Glu Glu Lys Thr Ala Leu Gln His Lys Val Arg Ala Leu
        115                 120                 125

Glu Glu Gln Leu Thr Asn Leu Ile Leu Ser Pro Ala Gly Ala Gln Glu
    130                 135                 140

His Pro Glu Val Thr Ser Leu Lys Ser Phe Val Glu Gln Gln Asp Asn
```

```
145                150                155                160

Ser Ile Arg Glu Leu Leu Gln Ser Val Glu Glu Gln Tyr Lys Gln Leu
               165                170                175

Ser Gln Gln His Met Gln Ile Lys Glu Ile Glu Lys Gln Leu Arg Lys
              180                185                190

Thr Gly Ile Gln Glu Pro Ser Glu Asn Ser Leu Ser Ser Lys Ser Arg
             195                200                205

Ala Pro Arg Thr Thr Pro Pro Leu Gln Leu Asn Glu Thr Glu Asn Thr
    210                215                220

Glu Gln Asp Ala Ser His His His His His His
225                230                235

<210> SEQ ID NO 167
<211> LENGTH: 182
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 167

Ser Arg Ile Asp Gln Asp Asn Ser Ser Phe Asp Ser Val Ser Pro Glu
1                5                10                15

Pro Lys Ser Arg Phe Ala Met Leu Asp Asp Val Lys Ile Leu Ala Asn
              20                25                30

Gly Leu Leu Gln Leu Gly His Gly Leu Lys Asp Phe Val His Lys Thr
         35                40                45

Lys Gly Gln Ile Asn Asp Ile Phe Gln Lys Leu Asn Ile Phe Asp Gln
    50                55                60

Ser Phe Tyr Asp Leu Ser Leu Gln Thr Ser Glu Ile Lys Glu Glu Glu
65                70                75                80

Lys Glu Leu Arg Arg Thr Thr Tyr Lys Leu Gln Val Lys Asn Glu Glu
              85                90                95

Val Lys Asn Met Ser Leu Glu Leu Asn Ser Lys Leu Glu Ser Leu Leu
              100                105                110

Glu Glu Lys Ile Leu Leu Gln Gln Lys Val Lys Tyr Leu Glu Glu Gln
         115                120                125

Leu Thr Asn Leu Ile Gln Asn Gln Pro Ala Thr Pro Glu His Pro Glu
    130                135                140

Val Thr Ser Leu Lys Ser Phe Val Glu Lys Glu Gln Lys Leu Ile Ser
145                150                155                160

Glu Glu Asp Leu Gly Gly Glu Gln Lys Leu Ile Ser Glu Glu Asp Leu
              165                170                175

His His His His His His
         180

<210> SEQ ID NO 168
<211> LENGTH: 33
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 168

Arg Phe Ala Ser Trp Asp Glu Met Asn Val Leu Ala His Gly Leu Leu
1                5                10                15

Gln Leu Gly Gln Gly Leu Arg Glu His Ala Glu Arg Thr Arg Ser Gln
```

-continued

```
                20              25              30

Leu

<210> SEQ ID NO 169
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Arg Phe Ala Met Leu Asp Asp Val Lys Ile Leu Ala Asn Gly Leu Leu
1               5                   10                  15

Gln Leu Gly His Gly Leu Lys Asp Phe Val His Lys Thr Lys Gly Gln
            20                  25                  30

Ile

<210> SEQ ID NO 170
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Glu Pro Lys Ser Arg Phe Ala Met Leu Asp Asp Val Lys Ile Leu Ala
1               5                   10                  15

Asn Gly Leu Leu Gln Leu Gly His Gly Leu
            20                  25

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ala Gly Ser Ser Pro Gly Gly
1               5

<210> SEQ ID NO 172
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Gly Gly Gly Gly Ser
1               5

<210> SEQ ID NO 173
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173
```

```
Gly Pro Ser Ser Gly Ala Pro Pro Pro Lys
1               5                   10

<210> SEQ ID NO 174
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Gly Gly Gly Ser Lys
1               5

<210> SEQ ID NO 175
<211> LENGTH: 455
<212> TYPE: PRT
<213> ORGANISM: Rattus norvegicus

<400> SEQUENCE: 175

Met His Thr Ile Lys Leu Leu Leu Phe Val Val Pro Leu Val Ile Ser
1               5                   10                  15

Ser Arg Val Asp Pro Asp Leu Ser Pro Phe Asp Ser Val Pro Ser Glu
                20                  25                  30

Pro Lys Ser Arg Phe Ala Met Leu Asp Asp Val Lys Ile Leu Ala Asn
            35                  40                  45

Gly Leu Leu Gln Leu Gly His Gly Leu Lys Asp Phe Val His Lys Thr
        50                  55                  60

Lys Gly Gln Ile Asn Asp Ile Phe Gln Lys Leu Asn Ile Phe Asp Gln
65                  70                  75                  80

Cys Phe Tyr Asp Leu Ser Leu Gln Thr Asn Glu Ile Lys Glu Glu Glu
                85                  90                  95

Lys Glu Leu Arg Arg Thr Thr Ser Lys Leu Gln Val Lys Asn Glu Glu
            100                 105                 110

Val Lys Asn Met Ser Leu Glu Leu Asn Ser Lys Leu Glu Ser Leu Leu
        115                 120                 125

Glu Glu Lys Met Ala Leu Gln His Arg Val Arg Ala Leu Glu Glu Gln
    130                 135                 140

Leu Thr Ser Leu Val Gln Asn Pro Pro Gly Ala Arg Glu His Pro Glu
145                 150                 155                 160

Val Thr Ser Leu Lys Ser Phe Val Glu Gln Gln Asp Asn Ser Ile Arg
                165                 170                 175

Glu Leu Leu Gln Ser Val Glu Glu Gln Tyr Lys Gln Leu Ser Gln Gln
            180                 185                 190

His Ile Gln Ile Lys Glu Ile Glu Asn Gln Leu Arg Lys Thr Gly Ile
        195                 200                 205

Gln Glu Pro Thr Glu Asn Ser Leu Tyr Ser Lys Pro Arg Ala Pro Arg
    210                 215                 220

Thr Thr Pro Pro Leu His Leu Lys Glu Ala Lys Asn Ile Glu Gln Asp
225                 230                 235                 240

Asp Leu Pro Ala Asp Cys Ser Ala Ile Tyr Asn Arg Gly Glu His Thr
                245                 250                 255

Ser Gly Val Tyr Thr Ile Arg Pro Ser Ser Ser Gln Val Phe Asn Val
            260                 265                 270

Tyr Cys Asp Thr Gln Ser Gly Thr Pro Arg Thr Leu Ile Gln His Arg
        275                 280                 285
```

```
Lys Asp Gly Ser Gln Asn Phe Asn Gln Thr Trp Glu Asn Tyr Glu Lys
    290                 295                 300

Gly Phe Gly Arg Leu Asp Gly Glu Phe Trp Leu Gly Leu Glu Lys Ile
305                 310                 315                 320

Tyr Ala Ile Val Lys Gln Ser Asn Tyr Ile Leu Arg Leu Glu Leu Gln
                325                 330                 335

Asp Trp Lys Asp Ser Lys His Tyr Ala Glu Tyr Ser Phe His Leu Gly
                340                 345                 350

Asn His Glu Thr Asn Tyr Thr Leu His Val Ala Glu Ile Ala Ala Asn
        355                 360                 365

Ile Pro Glu Ala Leu Pro Glu His Arg Asp Leu Met Phe Ser Thr Trp
    370                 375                 380

Asp His Arg Ala Lys Gly Gln Leu Tyr Cys Pro Glu Ser Tyr Ser Gly
385                 390                 395                 400

Gly Trp Trp Phe Ser Asp Met Cys Gly Glu Asn Asn Leu Asn Gly Lys
                405                 410                 415

Tyr Asn Lys Pro Arg Ala Lys Ser Lys Pro Glu Arg Arg Arg Gly Ile
                420                 425                 430

Ser Trp Arg Pro Arg Gly Gly Lys Leu Tyr Ser Ile Lys Ser Ser Lys
        435                 440                 445

Met Met Leu Gln Pro Thr Thr
    450                 455

<210> SEQ ID NO 176
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 176

Ser Arg Val Asp Pro Asp Leu Ser Pro Phe Asp Ser Val Pro Ser Glu
1                   5                   10                  15

Pro Lys Ser Arg Phe Ala Met Leu Asp Asp Val Lys Ile Leu Ala Asn
                20                  25                  30

Gly Leu Leu Gln Leu Gly His Gly Leu Lys Asp Phe Val His Lys Thr
        35                  40                  45

Lys Gly Gln Ile Asn Asp Ile Phe Gln Lys Leu Asn Ile Phe Asp Gln
    50                  55                  60

Cys Phe Tyr Asp Leu Ser Leu Gln Thr Asn Glu Ile Lys Glu Glu Glu
65                  70                  75                  80

Lys Glu Leu Arg Arg Thr Thr Ser Lys Leu Gln Val Lys Asn Glu Glu
                85                  90                  95

Val Lys Asn Met Ser Leu Glu Leu Asn Ser Lys Leu Glu Ser Leu Leu
                100                 105                 110

Glu Glu Lys Met Ala Leu Gln His Arg Val Arg Ala Leu Glu Glu Gln
        115                 120                 125

Leu Thr Ser Leu Val Gln Asn Pro Pro Gly Ala Arg Glu His Pro Glu
    130                 135                 140

Val Thr Ser Leu Lys Ser Phe Val Glu Gln Gln Asp Asn Ser Ile Arg
145                 150                 155                 160

Glu Leu Leu Gln Ser Val Glu Glu Gln Tyr Lys Gln Leu Ser Gln Gln
                165                 170                 175

His Ile Gln Ile Lys Glu Ile Glu Asn Gln Leu Arg Lys Thr Gly Ile
                180                 185                 190
```

```
Gln Glu Pro Thr Glu Asn Ser Leu Tyr Ser Lys Pro Arg Ala Pro Arg
        195                 200                 205

Thr Thr Pro Pro Leu His Leu Lys Glu Ala Lys Asn Ile Glu Gln Asp
    210                 215                 220

Glu Gln Lys Leu Ile Ser Glu Glu Asp Leu Gly Gly Glu Gln Lys Leu
225                 230                 235                 240

Ile Ser Glu Glu Asp Leu His His His His His
                245                 250

<210> SEQ ID NO 177
<211> LENGTH: 210
<212> TYPE: PRT
<213> ORGANISM: Macaca fascicularis

<400> SEQUENCE: 177

Met Phe Thr Ile Lys Leu Leu Leu Phe Ile Val Pro Leu Val Ile Ser
1               5                   10                  15

Ser Arg Ile Asp Gln Asp Asn Ser Ser Phe Asp Ser Val Ser Pro Glu
            20                  25                  30

Pro Lys Ser Arg Phe Ala Met Leu Asp Asp Val Lys Ile Leu Ala Asn
        35                  40                  45

Gly Leu Leu Gln Leu Gly His Gly Leu Lys Asp Phe Val His Lys Thr
    50                  55                  60

Lys Gly Gln Ile Asn Asp Ile Phe Gln Lys Leu Asn Ile Phe Asp Gln
65                  70                  75                  80

Ser Phe Tyr Asp Leu Ser Leu Gln Thr Ser Glu Ile Lys Glu Glu Glu
                85                  90                  95

Lys Glu Leu Arg Arg Thr Thr Tyr Lys Leu Gln Val Lys Asn Glu Glu
            100                 105                 110

Val Lys Asn Met Ser Leu Glu Leu Asn Ser Lys Leu Glu Ser Leu Leu
            115                 120                 125

Glu Glu Lys Ile Leu Leu Gln Gln Lys Val Lys Tyr Leu Glu Glu Gln
        130                 135                 140

Leu Thr Asn Leu Ile Gln Asn Gln Pro Ala Thr Pro Glu His Pro Glu
145                 150                 155                 160

Val Thr Ser Leu Lys Ser Phe Val Glu Lys Gln Asp Asn Ser Ile Lys
                165                 170                 175

Asp Leu Leu Gln Thr Val Glu Glu Gln Tyr Lys Gln Leu Asn Gln Gln
            180                 185                 190

His Ser Gln Ile Lys Glu Ile Glu Asn Gln Leu Arg Met Thr Asn Ile
        195                 200                 205

Gln Glu
    210

<210> SEQ ID NO 178
<211> LENGTH: 356
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 178

Gly Pro Val Gln Ser Lys Ser Pro Arg Phe Ala Ser Trp Asp Glu Met
1               5                   10                  15

Asn Val Leu Ala His Gly Leu Leu Gln Leu Gly Gln Gly Leu Arg Glu
            20                  25                  30
```

```
His Ala Glu Arg Thr Arg Ser Gln Leu Ser Ala Leu Glu Arg Arg Leu
        35                  40                  45

Ser Ala Cys Gly Ser Ala Cys Gln Gly Thr Glu Gly Ser Thr Asp Leu
        50                  55                  60

Pro Leu Ala Pro Glu Ser Arg Val Asp Pro Glu Val Leu His Ser Leu
65                  70                  75                  80

Gln Thr Gln Leu Lys Ala Gln Asn Ser Arg Ile Gln Gln Leu Phe His
                85                  90                  95

Lys Val Ala Gln Gln Gln Arg His Leu Glu Lys Gln His Leu Arg Ile
                100                 105                 110

Gln His Leu Gln Ser Gln Phe Gly Leu Leu Asp Glu Pro Arg Gly Pro
        115                 120                 125

Thr Ile Lys Pro Cys Pro Pro Cys Lys Cys Pro Ala Pro Asn Leu Leu
        130                 135                 140

Gly Gly Pro Ser Val Phe Ile Phe Pro Pro Lys Ile Lys Asp Val Leu
145                 150                 155                 160

Met Ile Ser Leu Ser Pro Ile Val Thr Cys Val Val Val Asp Val Ser
                165                 170                 175

Glu Asp Asp Pro Asp Val Gln Ile Ser Trp Phe Val Asn Asn Val Glu
                180                 185                 190

Val His Thr Ala Gln Thr Gln Thr His Arg Glu Asp Tyr Asn Ser Thr
                195                 200                 205

Leu Arg Val Val Ser Ala Leu Pro Ile Gln His Gln Asp Trp Met Ser
        210                 215                 220

Gly Lys Glu Phe Lys Cys Lys Val Asn Asn Lys Asp Leu Pro Ala Pro
225                 230                 235                 240

Ile Glu Arg Thr Ile Ser Lys Pro Lys Gly Ser Val Arg Ala Pro Gln
                245                 250                 255

Val Tyr Val Leu Pro Pro Pro Glu Glu Glu Met Thr Lys Lys Gln Val
                260                 265                 270

Thr Leu Thr Cys Met Val Thr Asp Phe Met Pro Glu Asp Ile Tyr Val
        275                 280                 285

Glu Trp Thr Asn Asn Gly Lys Thr Glu Leu Asn Tyr Lys Asn Thr Glu
        290                 295                 300

Pro Val Leu Asp Ser Asp Gly Ser Tyr Phe Met Tyr Ser Lys Leu Arg
305                 310                 315                 320

Val Glu Lys Lys Asn Trp Val Glu Arg Asn Ser Tyr Ser Cys Ser Val
                325                 330                 335

Val His Glu Gly Leu His Asn His His Thr Thr Lys Ser Phe Ser Arg
                340                 345                 350

Thr Pro Gly Lys
        355
```

<210> SEQ ID NO 179
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 179
gaggtgcagc tttttggagtc tggggggaggc ttggtacagc ctggggggtc cctgagactc        60
tcctgtgcag cctctggatt caccttttagc acctatgcca tgagctgggt ccgccaggct       120

-continued

```
ccagggaagg ggctggaggg ggtctcaggt attagtggta ctggttatag aacatactac      180
gcagactccg tgaagggccg attcaccatc tccagagaca attccaagaa ctcgctgtat      240
ctgcaaatga acagcctgag agccgaggac acggccgtat attactgtgc gaaagatcgg      300
ggcttactat ggttcgggga attaacctac tggggccagg gaaccctggt caccgtctcc      360
tca                                                                    363
```

```
<210> SEQ ID NO 180
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 180

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Gly Val
        35                  40                  45

Ser Gly Ile Ser Gly Thr Gly Tyr Arg Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Leu Leu Trp Phe Gly Glu Leu Thr Tyr Trp Gly
            100                 105                 110

Gln Gly Thr Leu Val Thr Val Ser Ser
        115                 120
```

```
<210> SEQ ID NO 181
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 181
ggattcacct ttagcaccta tgcc                                             24
```

```
<210> SEQ ID NO 182
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Phe Thr Phe Ser Thr Tyr Ala
1               5
```

```
<210> SEQ ID NO 183
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 183
attagtggta ctggttatag aaca                                                    24

<210> SEQ ID NO 184
<211> LENGTH: 8
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 184

Ile Ser Gly Thr Gly Tyr Arg Thr
1               5

<210> SEQ ID NO 185
<211> LENGTH: 42
<212> TYPE: DNA
<213> ORGANISM: Artificial Sequence
<220> FEATURE:
<223> OTHER INFORMATION: Description of Artificial Sequence: Synthetic
     oligonucleotide

<400> SEQUENCE: 185
gcgaaagatc ggggcttact atggttcggg gaattaacct ac                               42

<210> SEQ ID NO 186
<211> LENGTH: 14
<212> TYPE: PRT
<213> ORGANISM: Artificial Sequence
<220> FEATURE:
<223> OTHER INFORMATION: Description of Artificial Sequence: Synthetic
     peptide

<400> SEQUENCE: 186

Ala Lys Asp Arg Gly Leu Leu Trp Phe Gly Glu Leu Thr Tyr
1               5                   10

<210> SEQ ID NO 187
<211> LENGTH: 318
<212> TYPE: DNA
<213> ORGANISM: Artificial Sequence
<220> FEATURE:
<223> OTHER INFORMATION: Description of Artificial Sequence: Synthetic
     polynucleotide

<400> SEQUENCE: 187
gacatccaga tgacccagtc tccttccacc ctgtctgcat ctgtaggaga cagagtcacc      60
atcacttgcc gggccagtca gagtattaat aactggttgg cctggtatca acagaaacca     120
gggaaggccc ctaacctcct gatctataag gcgtctagtt tagaaagtgg ggtcccatca     180
aggttcagcg gcagtggatc tgggacagaa ttcactctca ccatcagcag cctgcagcct     240
gatgattttg caacttatta ctgccaacaa tataatgatt attggacgtt cggccaaggg     300
accaaggtgg aaatcaaa                                                   318

<210> SEQ ID NO 188
<211> LENGTH: 106
<212> TYPE: PRT
<213> ORGANISM: Artificial Sequence
<220> FEATURE:
<223> OTHER INFORMATION: Description of Artificial Sequence: Synthetic
     polypeptide -continued

<400> SEQUENCE: 188

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Asn Trp
            20                  25                  30

Leu Ala Trp Tyr Gln Gln Lys Pro Gly Lys Ala Pro Asn Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Asp Tyr Trp Thr
                85                  90                  95

Phe Gly Gln Gly Thr Lys Val Glu Ile Lys
            100                 105

<210> SEQ ID NO 189
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189
cagagtatta ataactgg                                                          18

<210> SEQ ID NO 190
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gln Ser Ile Asn Asn Trp
1               5

<210> SEQ ID NO 191
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191 aaggcgtct                                                                    9

<210> SEQ ID NO 192
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Lys Ala Ser
1

<210> SEQ ID NO 193

-continued

```
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 193
caacaatata atgattattg gacg                                              24

<210> SEQ ID NO 194
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Gln Gln Tyr Asn Asp Tyr Trp Thr
1               5

<210> SEQ ID NO 195
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Glu Val Gln Leu Val Glu Ser Gly Gly Gly Val Ile Gln Pro Gly Gly
1               5                   10                  15

Ser Leu Arg Leu Ser Cys Ala Ala Ser Gly Phe Thr Phe Asp Asp Tyr
            20                  25                  30

Ala Met Asn Trp Val Arg Gln Gly Pro Gly Lys Gly Leu Glu Trp Val
        35                  40                  45

Ser Ala Ile Ser Gly Asp Gly Gly Ser Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Phe Phe Tyr Cys
                85                  90                  95

Ala Lys Asp Leu Arg Asn Thr Ile Phe Gly Val Val Ile Pro Asp Ala
            100                 105                 110

Phe Asp Ile Trp Gly Gln Gly Thr Met Val Thr Val Ser Ser Ala Ser
            115                 120                 125

Thr Lys Gly Pro Ser Val Phe Pro Leu Ala Pro Cys Ser Arg Ser Thr
    130                 135                 140

Ser Glu Ser Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Lys Thr Tyr Thr
            195                 200                 205

Cys Asn Val Asp His Lys Pro Ser Asn Thr Lys Val Asp Lys Arg Val
    210                 215                 220

Glu Ser Lys Tyr Gly Pro Pro Cys Pro Pro Cys Pro Ala Pro Glu Phe
```

```
225             230             235             240

Leu Gly Gly Pro Ser Val Phe Leu Phe Pro Pro Lys Pro Lys Asp Thr
            245             250             255

Leu Met Ile Ser Arg Thr Pro Glu Val Thr Cys Val Val Val Asp Val
            260             265             270

Ser Gln Glu Asp Pro Glu Val Gln Phe Asn Trp Tyr Val Asp Gly Val
            275             280             285

Glu Val His Asn Ala Lys Thr Lys Pro Arg Glu Glu Gln Phe Asn Ser
        290             295             300

Thr Tyr Arg Val Val Ser Val Leu Thr Val Leu His Gln Asp Trp Leu
305             310             315             320

Asn Gly Lys Glu Tyr Lys Cys Lys Val Ser Asn Lys Gly Leu Pro Ser
            325             330             335

Ser Ile Glu Lys Thr Ile Ser Lys Ala Lys Gly Gln Pro Arg Glu Pro
            340             345             350

Gln Val Tyr Thr Leu Pro Pro Ser Gln Glu Glu Met Thr Lys Asn Gln
            355             360             365

Val Ser Leu Thr Cys Leu Val Lys Gly Phe Tyr Pro Ser Asp Ile Ala
        370             375             380

Val Glu Trp Glu Ser Asn Gly Gln Pro Glu Asn Asn Tyr Lys Thr Thr
385             390             395             400

Pro Pro Val Leu Asp Ser Asp Gly Ser Phe Phe Leu Tyr Ser Arg Leu
            405             410             415

Thr Val Asp Lys Ser Arg Trp Gln Glu Gly Asn Val Phe Ser Cys Ser
            420             425             430

Val Met His Glu Ala Leu His Asn His Tyr Thr Gln Lys Ser Leu Ser
        435             440             445

Leu Ser Leu Gly Lys
    450
```

```
<210> SEQ ID NO 196
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Asp Ile Gln Met Thr Gln Ser Pro Ser Thr Leu Ser Ala Ser Val Gly
1               5               10              15

Asp Arg Val Thr Ile Thr Cys Arg Ala Ser Gln Ser Ile Arg Ser Trp
            20              25              30

Leu Ala Trp Tyr Gln Gln Lys Pro Gly Lys Ala Pro Lys Leu Leu Ile
            35              40              45

Tyr Lys Ala Ser Ser Leu Glu Ser Gly Val Pro Ser Arg Phe Ser Gly
        50              55              60

Ser Gly Ser Gly Thr Glu Phe Thr Leu Thr Ile Ser Ser Leu Gln Pro
65              70              75              80

Asp Asp Phe Ala Thr Tyr Tyr Cys Gln Gln Tyr Asn Ser Tyr Ser Tyr
            85              90              95

Thr Phe Gly Gln Gly Thr Lys Leu Glu Ile Lys Arg Thr Val Ala Ala
            100             105             110

Pro Ser Val Phe Ile Phe Pro Pro Ser Asp Glu Gln Leu Lys Ser Gly
            115             120             125
```

-continued

```
Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
    210
```